US010858354B2

(12) United States Patent
Janusz et al.

(10) Patent No.: US 10,858,354 B2
(45) Date of Patent: Dec. 8, 2020

(54) HPTP-BETA INHIBITORS

(71) Applicant: Aerpio Pharmaceuticals, Inc., Cincinnati, OH (US)

(72) Inventors: John Janusz, West Chester, OH (US); James Copp, Silverthrone, CO (US); Kevin Peters, Cincinnati, OH (US)

(73) Assignee: Aerpio Pharmaceuticals, Inc., Cincinnati, OH (US)

( * ) Notice: Subject to any disclaimer, the term of this patent is extended or adjusted under 35 U.S.C. 154(b) by 0 days.

(21) Appl. No.: 15/972,863

(22) Filed: May 7, 2018

(65) Prior Publication Data

US 2018/0354937 A1    Dec. 13, 2018

Related U.S. Application Data

(63) Continuation of application No. 14/657,276, filed on Mar. 13, 2015, now Pat. No. 9,994,560.

(60) Provisional application No. 61/953,680, filed on Mar. 14, 2014.

(51) Int. Cl.
C07D 417/04    (2006.01)

(52) U.S. Cl.
CPC .................. C07D 417/04 (2013.01)

(58) Field of Classification Search
None
See application file for complete search history.

(56) References Cited

U.S. PATENT DOCUMENTS

| | | | |
|---|---|---|---|
| 4,221,584 A | 9/1980 | Ziman |
| 4,735,961 A | 4/1988 | Baldwin et al. |
| 5,919,813 A | 7/1999 | de Juan, Jr. |
| 5,980,929 A | 11/1999 | de Juan, Jr. |
| 6,455,035 B1 | 9/2002 | Suri et al. |
| 7,052,695 B2 | 5/2006 | Kalish |
| 7,226,755 B1 | 6/2007 | Peters et al. |
| 7,309,483 B2 | 12/2007 | Wiegand et al. |
| 7,354,579 B2 | 4/2008 | Holash et al. |
| 7,507,568 B2 | 3/2009 | Evdokimov et al. |
| 7,589,212 B2 | 9/2009 | Gray et al. |
| 7,622,593 B2 | 11/2009 | Gray et al. |
| 7,632,862 B2 | 12/2009 | Peters et al. |
| 7,740,846 B2 | 6/2010 | Gerber et al. |
| 7,769,575 B2 | 8/2010 | Evdokimov et al. |
| 7,795,444 B2 | 9/2010 | Gray et al. |
| 7,973,142 B2 | 7/2011 | Rotello et al. |
| 8,106,078 B2 | 1/2012 | Gray et al. |
| 8,188,125 B2 | 5/2012 | Gray et al. |
| 8,258,311 B2 | 9/2012 | Gray et al. |
| 8,309,537 B2 | 11/2012 | Gardner et al. |
| 8,329,916 B2 | 12/2012 | Gray, et al. |
| 8,338,615 B2 | 12/2012 | Gray et al. |
| 8,524,235 B2 | 9/2013 | Rotello et al. |
| 8,536,181 B2 | 9/2013 | Gardner et al. |
| 8,569,348 B2 | 10/2013 | Shalwitz et al. |
| 8,778,412 B2 | 7/2014 | Shalwitz et al. |
| 8,846,685 B2 | 9/2014 | Gray et al. |
| 8,883,774 B2 | 11/2014 | Shalwitz et al. |
| 8,883,832 B2 | 11/2014 | Shalwitz et al. |
| 8,895,563 B2 | 11/2014 | Gray et al. |
| 8,946,232 B2 | 2/2015 | Gray et al. |
| 8,968,766 B2 | 3/2015 | Hughes et al. |
| 8,999,325 B2 | 4/2015 | Peters et al. |
| 8,999,953 B2 | 4/2015 | Loftsson et al. |
| 8,999,971 B2 | 4/2015 | Shalwitz et al. |
| 9,045,495 B2 | 6/2015 | Gardner et al. |
| 9,096,555 B2 | 8/2015 | Shalwitz et al. |
| 9,126,958 B2 | 9/2015 | Gray et al. |
| 9,174,950 B2 | 11/2015 | Shalwitz et al. |
| 9,248,172 B2 | 2/2016 | Srivastava et al. |
| 9,278,930 B2 | 3/2016 | Shalwitz et al. |
| 9,284,285 B2 | 3/2016 | Gray et al. |
| 9,403,789 B2 | 8/2016 | Eissenstat et al. |
| 9,440,963 B2 | 9/2016 | Peters et al. |
| 9,539,245 B2 | 1/2017 | Peters et al. |
| RE46,592 E | 10/2017 | Gray et al. |
| 9,795,594 B2 | 10/2017 | Gray et al. |
| 9,926,367 B2 | 3/2018 | Rotello et al. |
| 9,949,956 B2 | 4/2018 | Shalwitz et al. |
| 9,994,560 B2 | 6/2018 | Janusz et al. |
| 2003/0040463 A1 | 2/2003 | Wiegand et al. |
| 2003/0055006 A1 | 3/2003 | Siemeister et al. |
| 2004/0077065 A1 | 4/2004 | Evdokimov et al. |
| 2007/0299116 A1 | 12/2007 | Gray et al. |
| 2008/0004267 A1 | 1/2008 | Gray et al. |

(Continued)

FOREIGN PATENT DOCUMENTS

| | | | |
|---|---|---|---|
| CN | 101506183 A | 8/2009 |
| CN | 103347565 A | 10/2013 |

(Continued)

OTHER PUBLICATIONS

STN Registry database entry for CAS RN 1008510-37-9 (Entered STN database Mar. 18, 2008), Accessed Sep. 4, 2017.*
Co-pending U.S. Appl. No. 15/705,639, filed Sep. 15, 2017.
Co-pending U.S. Appl. No. 15/894,442, filed Feb. 12, 2018.
Co-pending U.S. Appl. No. 15/913,392, filed Mar. 6, 2018.
Co-pending U.S. Appl. No. 15/958,346, filed Apr. 20, 2018.
Co-pending U.S. Appl. No. 15/958,355, filed Apr. 20, 2018.
Co-pending U.S. Appl. No. 15/958,358, filed Apr. 20, 2018.
Co-pending U.S. Appl. No. 15/969,109, filed May 2, 2018.
Lip, et al. Plasma vascular endothelial growth factor, angiopoietin-2, and soluble angiopoietin receptor tie-2 in diabetic retinopathy: effects of laser photocoagulation and angiotensin receptor blockade. Br J Ophthalmol. Dec. 2004;88(12):1543-6.

(Continued)

Primary Examiner — Alicia L Otton

(74) Attorney, Agent, or Firm — Wilson Sonsini Goodrich & Rosati

(57) ABSTRACT

Disclosed herein are compounds effective for activation of Tie-2 and inhibition of HPTP-beta. The compounds can provide effective therapy for conditions associated with angiogenesis, for example, ocular conditions. Formulations for increased solubility are disclosed.

3 Claims, 53 Drawing Sheets

Specification includes a Sequence Listing.

(56) References Cited

U.S. PATENT DOCUMENTS

| | | |
|---|---|---|
| 2008/0076764 A1 | 3/2008 | Peters et al. |
| 2008/0108631 A1 | 5/2008 | Gray et al. |
| 2008/0268051 A1 | 10/2008 | Hughes et al. |
| 2009/0022715 A1 | 1/2009 | Rotello et al. |
| 2009/0227639 A1 | 9/2009 | Gray et al. |
| 2010/0016336 A1 | 1/2010 | Gray et al. |
| 2010/0030487 A1 | 2/2010 | Evdokimov et al. |
| 2010/0056610 A1 | 3/2010 | Peters et al. |
| 2010/0069448 A1 | 3/2010 | Gray et al. |
| 2010/0226992 A1 | 9/2010 | Kabra |
| 2011/0110961 A1 | 5/2011 | Gardner et al. |
| 2011/0111058 A1 | 5/2011 | Shalwitz et al. |
| 2011/0112055 A1 | 5/2011 | Gardner et al. |
| 2011/0212951 A1 | 9/2011 | Gray et al. |
| 2011/0268694 A1 | 11/2011 | Shalwitz et al. |
| 2011/0274699 A1 | 11/2011 | Rotello et al. |
| 2011/0319455 A1 | 12/2011 | Klein et al. |
| 2012/0077853 A1 | 3/2012 | Gray et al. |
| 2012/0077975 A1 | 3/2012 | Gray et al. |
| 2012/0128625 A1 | 5/2012 | Shalwitz et al. |
| 2012/0129847 A1 | 5/2012 | Peters et al. |
| 2013/0023542 A1 | 1/2013 | Gray et al. |
| 2013/0023543 A1 | 1/2013 | Gray et al. |
| 2013/0095065 A1 | 4/2013 | Peters et al. |
| 2013/0095105 A1 | 4/2013 | Peters et al. |
| 2013/0096140 A1 | 4/2013 | Gray et al. |
| 2013/0137741 A1 | 5/2013 | Kabra et al. |
| 2013/0158010 A1 | 6/2013 | Shalwitz et al. |
| 2013/0158045 A1 | 6/2013 | Gardner et al. |
| 2013/0190324 A1 | 7/2013 | Kompella et al. |
| 2013/0324558 A1 | 12/2013 | Gray et al. |
| 2013/0331386 A1 | 12/2013 | Shalwitz et al. |
| 2014/0010805 A1 | 1/2014 | Hart et al. |
| 2014/0044707 A1 | 2/2014 | Rotello et al. |
| 2014/0066458 A1 | 3/2014 | Shalwitz et al. |
| 2014/0073566 A1 | 3/2014 | Koh et al. |
| 2014/0179693 A1 | 6/2014 | Shalwitz et al. |
| 2014/0221666 A1 | 8/2014 | Gray et al. |
| 2014/0242026 A1 | 8/2014 | Shalwitz et al. |
| 2014/0249100 A1 | 9/2014 | Shalwitz et al. |
| 2014/0275103 A1 | 9/2014 | Peters et al. |
| 2014/0288134 A1 | 9/2014 | Peters et al. |
| 2014/0364419 A1 | 12/2014 | Shalwitz et al. |
| 2015/0030603 A1 | 1/2015 | Kim et al. |
| 2015/0050277 A1 | 2/2015 | Peters et al. |
| 2015/0065781 A1 | 3/2015 | Bais et al. |
| 2015/0071941 A1 | 3/2015 | Sodhi et al. |
| 2015/0125455 A1 | 5/2015 | Green et al. |
| 2015/0125542 A1 | 5/2015 | Ohto et al. |
| 2015/0157617 A1 | 6/2015 | Shalwitz et al. |
| 2015/0175676 A1 | 6/2015 | Fandl et al. |
| 2015/0190432 A1 | 7/2015 | Doiron et al. |
| 2015/0210656 A1 | 7/2015 | Gray et al. |
| 2015/0218098 A1 | 8/2015 | Gardner et al. |
| 2015/0232575 A1 | 8/2015 | Peters et al. |
| 2015/0258120 A1 | 9/2015 | Zarnitsyn et al. |
| 2015/0259335 A1 | 9/2015 | Janusz et al. |
| 2015/0290235 A1 | 10/2015 | Gros et al. |
| 2015/0297740 A1 | 10/2015 | Rau et al. |
| 2016/0000871 A1 | 1/2016 | Quaggin et al. |
| 2016/0008327 A1 | 1/2016 | Shalwitz et al. |
| 2016/0030393 A1 | 2/2016 | Breslin et al. |
| 2016/0038467 A1 | 2/2016 | Peters |
| 2016/0045566 A1 | 2/2016 | Purcell et al. |
| 2016/0058828 A1 | 3/2016 | Dumont et al. |
| 2016/0082129 A1 | 3/2016 | Peters |
| 2016/0130321 A1 | 5/2016 | Burian |
| 2016/0130337 A1 | 5/2016 | Gekkieva et al. |
| 2016/0137717 A1 | 5/2016 | Burian |
| 2016/0144025 A1 | 5/2016 | Vitti et al. |
| 2016/0151410 A1 | 6/2016 | Ma et al. |
| 2016/0151448 A1 | 6/2016 | Van et al. |
| 2016/0159893 A1 | 6/2016 | Burian et al. |
| 2016/0168240 A1 | 6/2016 | Burian et al. |
| 2016/0220540 A1 | 8/2016 | Peters et al. |
| 2016/0220541 A1 | 8/2016 | Peters et al. |
| 2016/0251421 A1 | 9/2016 | Brown et al. |
| 2016/0252526 A1 | 9/2016 | Bergmann et al. |
| 2016/0374996 A1 | 12/2016 | Gray et al. |
| 2017/0260265 A1 | 9/2017 | Duerr et al. |
| 2017/0298019 A1 | 10/2017 | Gardner et al. |
| 2017/0319602 A1 | 11/2017 | Peters et al. |
| 2018/0009890 A1 | 1/2018 | Peters et al. |
| 2018/0016245 A1 | 1/2018 | Shalwitz et al. |
| 2018/0022741 A1 | 1/2018 | Peters et al. |
| 2018/0037579 A1 | 2/2018 | Peters et al. |
| 2018/0044432 A1 | 2/2018 | Peters et al. |
| 2018/0092883 A1 | 4/2018 | Peters et al. |

FOREIGN PATENT DOCUMENTS

| | | | |
|---|---|---|---|
| EP | 1165115 B1 | 5/2003 | |
| EP | 1292335 B1 | 5/2007 | |
| EP | 2004697 A2 | 12/2008 | |
| EP | 2371865 A2 | 10/2011 | |
| EP | 2385763 A1 | 11/2011 | |
| EP | 2451279 A1 | 5/2012 | |
| EP | 2142189 B1 | 2/2013 | |
| EP | 2592072 A2 | 5/2013 | |
| EP | 2592073 A2 | 5/2013 | |
| EP | 2624916 A2 | 8/2013 | |
| EP | 2766043 A1 | 8/2014 | |
| EP | 2041129 B1 | 9/2014 | |
| EP | 2041102 B1 | 11/2014 | |
| EP | 2803663 A1 | 11/2014 | |
| EP | 2038265 B1 | 3/2015 | |
| EP | 2967066 A1 | 1/2016 | |
| WO | WO-9622997 A1 | 8/1996 | |
| WO | WO-9631598 A1 | 10/1996 | |
| WO | WO-9818914 A1 | 5/1998 | |
| WO | WO-0057901 A1 | 10/2000 | |
| WO | WO-03072100 A1 | 9/2003 | |
| WO | WO-03084565 A2 | 10/2003 | |
| WO | WO-2004043927 A1 | 5/2004 | |
| WO | WO-2004043928 A2 | 5/2004 | |
| WO | WO-2005089755 A1 | 9/2005 | |
| WO | WO-2006068953 A2 | 6/2006 | |
| WO | WO-2006116713 A1 | 11/2006 | |
| WO | WO-2007033216 A2 | 3/2007 | |
| WO | WO-2007116360 A2 | 10/2007 | |
| WO | WO 2008/002569 * | 1/2008 | ........... C07D 277/28 |
| WO | WO-2008002569 A2 | 1/2008 | |
| WO | WO-2008002570 A2 | 1/2008 | |
| WO | WO-2008002571 A2 | 1/2008 | |
| WO | WO-2008002570 B1 | 4/2008 | |
| WO | WO-2008002571 B1 | 4/2008 | |
| WO | WO-2010081172 A1 | 7/2010 | |
| WO | WO-2011005330 A1 | 1/2011 | |
| WO | WO-2011057112 A1 | 5/2011 | |
| WO | WO-2011057115 A1 | 5/2011 | |
| WO | WO-2011057121 A1 | 5/2011 | |
| WO | WO-2012047966 A2 | 4/2012 | |
| WO | WO-2013056233 A1 | 4/2013 | |
| WO | WO-2013056240 A1 | 4/2013 | |
| WO | WO-2014145068 A1 | 9/2014 | |
| WO | WO-2015138882 A1 | 9/2015 | |
| WO | WO-2015152416 A1 | 10/2015 | |
| WO | WO-2016022813 A1 | 2/2016 | |
| WO | WO-2016049183 A1 | 3/2016 | |

OTHER PUBLICATIONS

Notice of allowance dated Apr. 4, 2018 for U.S. Appl. No. 14/657,276.
Office action dated Oct. 12, 2016 for U.S. Appl. No. 14/657,276.
Office action dated Feb. 22, 2017 for U.S. Appl. No. 14/657,276.
Office action dated Sep. 8, 2017 for U.S. Appl. No. 14/657,276.
Goel, et al. Effects of vascular-endothelial protein tyrosine phosphatase inhibition on breast cancer vasculature and metastatic progression. J Natl Cancer Inst. Aug. 21, 2013;105(16):1188-201. doi: 10.1093/jnci/djt164. Epub Jul. 30, 2013.
Guo, et al., Development of BACE1 Inhibitors for Alzheimer's Disease, Current Medicinal Chemistry, 2006, 13:1811-29.

(56) References Cited

OTHER PUBLICATIONS

Hoekstra, et al., thrombin receptor (par-t) antagonists. heterocycle-based peptidomimetics of the sellr agonist motif, Bioorganic & Medicinal Chemistry Letters 8, 1998, 1649-54.
International search report and written opinion dated Jul. 30, 2015 for PCT/US2015/020425.
Khattab, et al., Coupling Reactions of Hydralazine with Amino Acids and their Adducts for Antihypertensive Activities, J. Heterocyclic Chem., (2004), 41:387-392.
Pubchem. Compound Summary for: CID 52799544. Create Date: May 20, 2011. Retrieved on Apr. 27, 2015. https://pubchem.ncbi.nlm.nih.gov/compound/52799544.
STN Registry database entry for CAS RN 1222455-25-5 (Entered STN database May 12, 2010), Accessed Sep. 4, 2017.

* cited by examiner

SEQUENCE LISTING

<160> NUMBER OF SEQ ID NOS: 2

<210> SEQ ID NO 1
<211> LENGTH: 231
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val

```
                    35                  40                  45
Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro Tyr Tyr Gly Thr Ser His Trp Tyr Phe Asp Val
                100                 105                 110

Trp Gly Gln Gly Thr Leu Val Thr Val Ser Ser Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
210                 215                 220

Ser Cys Asp Lys Thr His Leu
225                 230

<210> SEQ ID NO 2
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Gln Leu Thr Gln Ser Pro Ser Ser Leu Ser Ala Ser Val Gly
 1                   5                  10                  15

Asp Arg Val Thr Ile Thr Cys Ser Ala Ser Gln Asp Ile Ser Asn Tyr
                 20                  25                  30

Leu Asn Trp Tyr Gln Gln Lys Pro Gly Lys Ala Pro Lys Val Leu Ile
                 35                  40                  45

Tyr Phe Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160
```

-continued

```
Glu Ser Val Thr Glu Gln Asp Ser Lys Asp Ser Thr Tyr Ser Leu Ser
                165             170             175

Ser Thr Leu Thr Gln Ser Ser Gly Leu Tyr Ser Leu Ser Val Val
            180             185             190

Thr Val Pro Ser Ser Ser Leu Gly Thr Gln Thr Tyr Ile Cys Asn Val
            195             200             205

Asn His Lys Pro Ser Asn Thr Lys Val Asp Lys Lys Val Glu Pro Lys
    210             215             220

Ser Cys Asp Lys Thr His Leu
225             230
```

HPTP-BETA INHIBITORS

CROSS-REFERENCE TO RELATED APPLICATIONS

This Application is a continuation of U.S. application Ser. No. 14/657,276 filed Mar. 13, 2015, which claims the benefit of U.S. Provisional Application No. 61/953,680, filed Mar. 14, 2014, the contents of each of which is incorporated herein by reference in its entirety.

SEQUENCE LISTING

The instant application contains a Sequence Listing which has been submitted electronically in ASCII format via EFS-Web and is hereby incorporated by reference in its entirety. Said ASCII copy, created on Mar. 12, 2015 Apr. 23, 2018, is named 45725713301SL.TXT and is 4,569 bytes in size.

INCORPORATION BY REFERENCE

Each patent, publication, and non-patent literature cited in the application is hereby incorporated by reference in its entirety as if each was incorporated by reference individually.

BACKGROUND

The eye comprises several structurally and functionally distinct vascular beds, which supply ocular components critical to the maintenance of vision. These include the retinal and choroidal vasculatures, which supply the inner and outer portions of the retina, respectively, and the limbal vasculature located at the periphery of the cornea. Injuries and diseases that impair the normal structure or function of these vascular beds are among the leading causes of visual impairment and blindness. For example, diabetic retinopathy is a common disease affecting the retinal vasculature, and is a leading cause of vision loss among the working age population in the United States. Vascularization of the cornea secondary to injury or disease is yet another category of ocular vascular disease that can lead to severe impairment of vision.

or aflibercept (2 mg) by intravitreal injection at the discretion of the study investigator.

Figure 48:
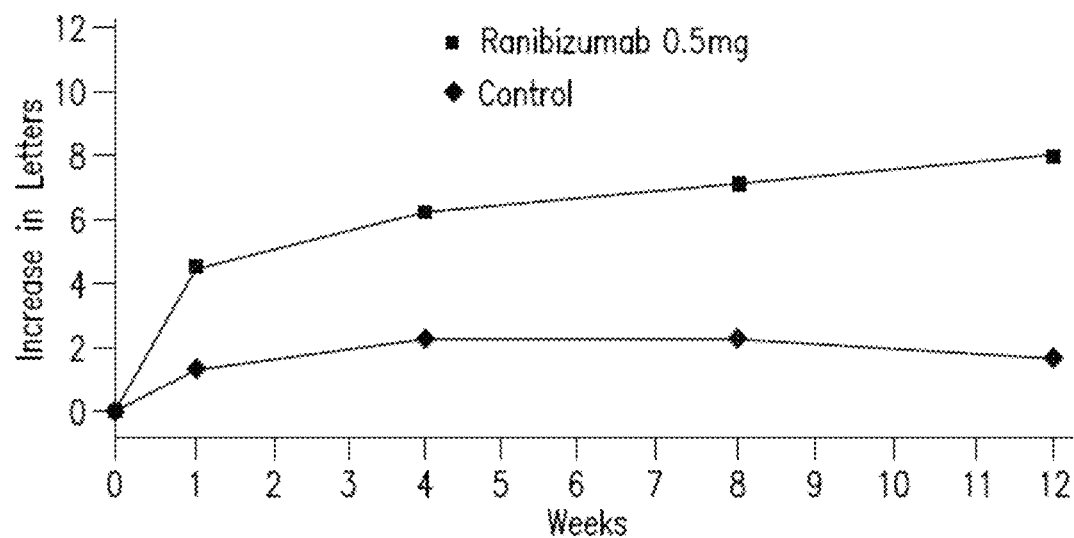

FIG. 48 depicts the results of Phase III studies to determine the effect of intravitreal injections of ranibizumab in patients with diabetic macular edema.

Figure 49:
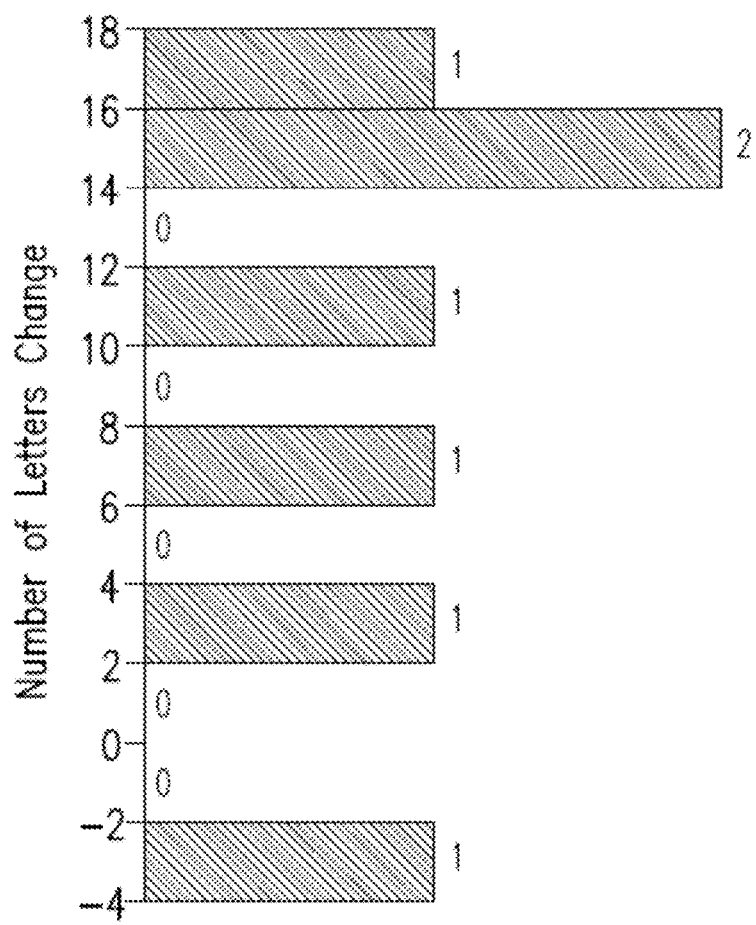

FIG. 49 depicts the increased visual acuity of a study wherein 4 patients received 5 mg of a compound disclosed herein subcutaneously twice daily for 28 days and subsequently were treated with either ranibizumab (0.3 or 0.5 mg) or aflibercept (2 mg) by intravitreal injection.

Figure 50:
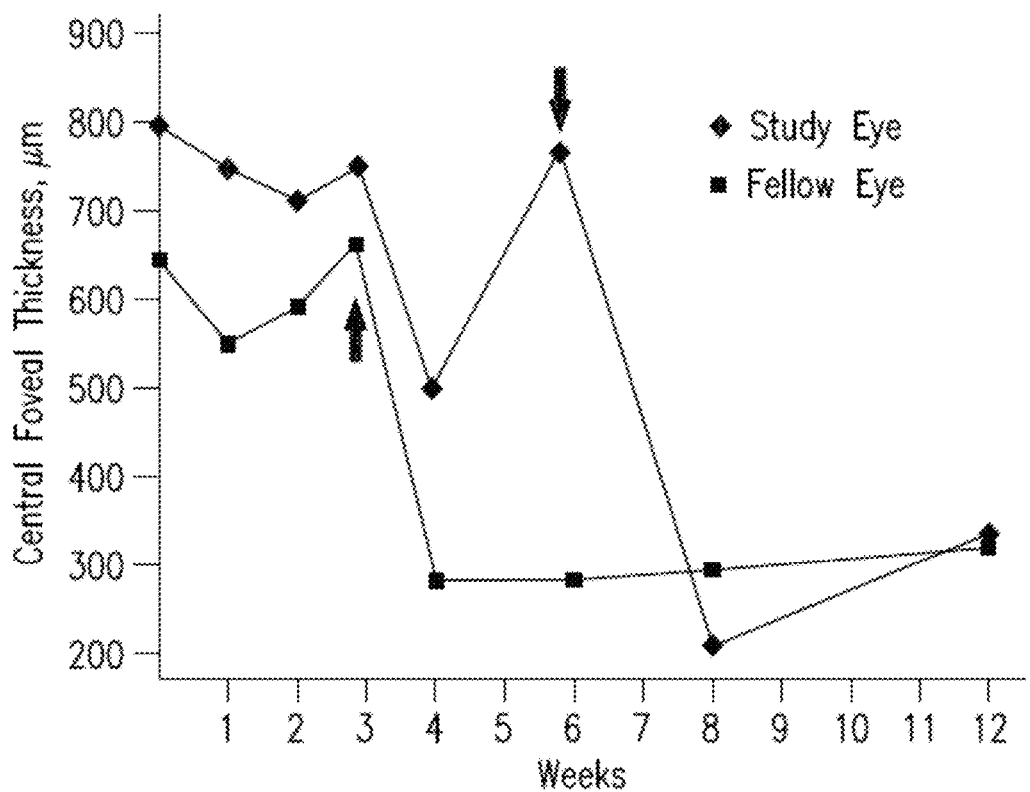

FIG. 50 graphs changes in central foveal thickness over time in an eye treated with a drug/antibody combination.

Figure 51:
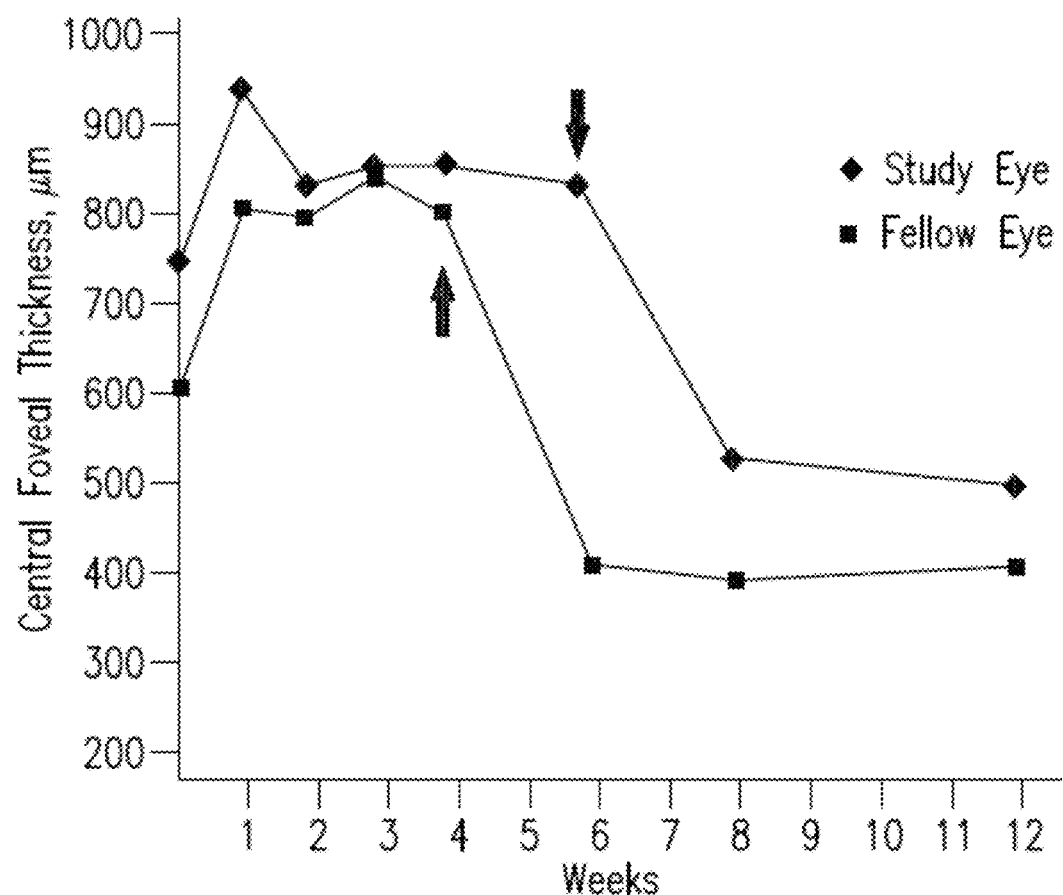

FIG. 51 graphs changes in central foveal thickness over time in an eye treated with a drug/antibody combination.

Figure 52:
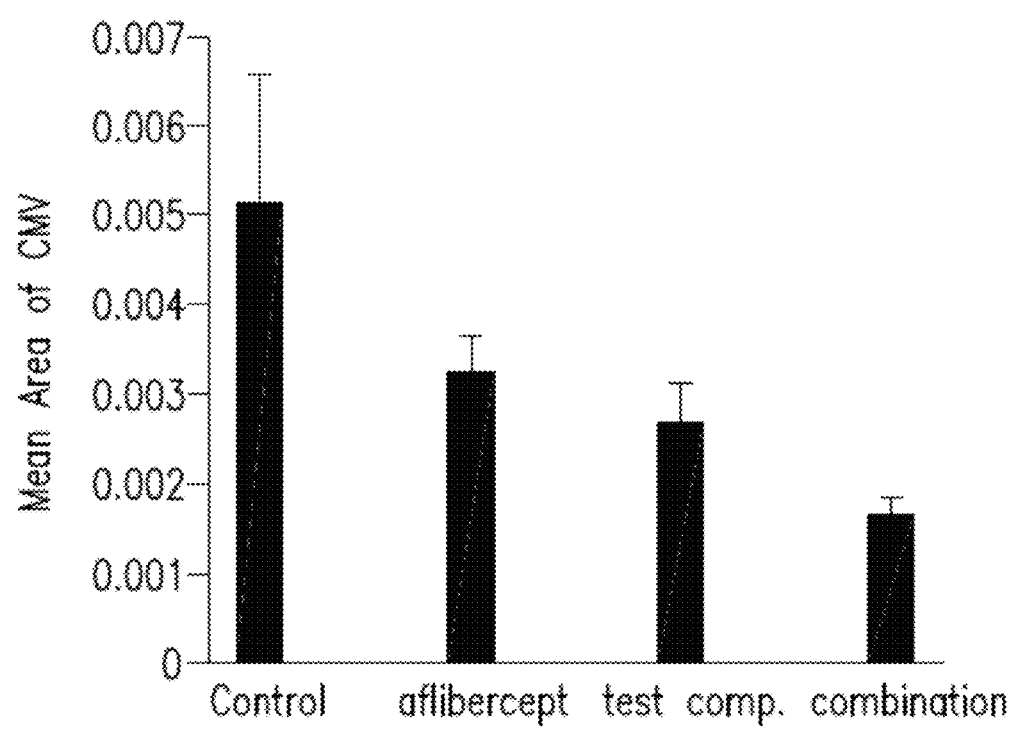

FIG. 52 is a graphic representation of in vivo experiments performed in 6 week old C57BL/6 mice.

Figure 53A:
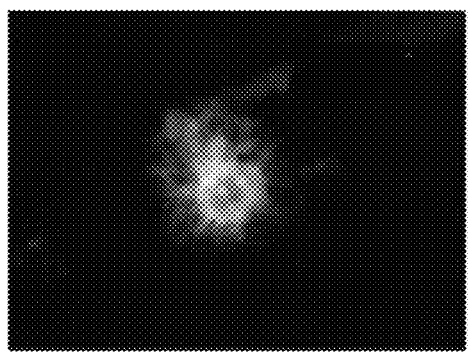

FIG. 53A illustrates the extent of choroidal neovascularization evident in a control sample stained with FITC-labeled *Griffonia simplicifolia* (GSA) of the experiment of FIG. 52.

Figure 53B:
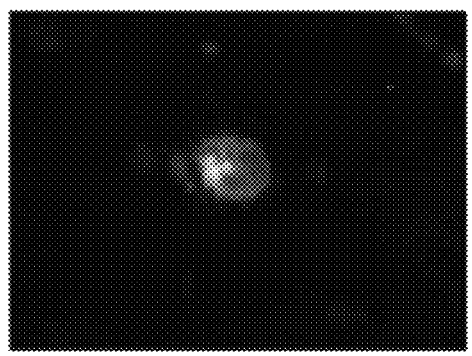

FIG. 53B represents the extent of neovascularization in the choroidal tissue of animals treated with aflibercept, stained with FITC-labeled *Griffonia simplicifolia* (GSA).

Figure 53C:
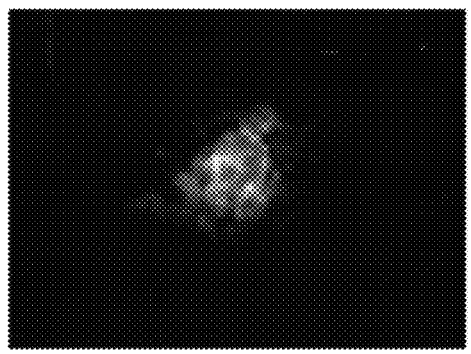

FIG. 53C represents the extent of neovascularization in tissue treated with a Tie-2 signaling enhancer, which was stained with FITC-labeled *Griffonia simplicifolia* (GSA).

Figure 53D:
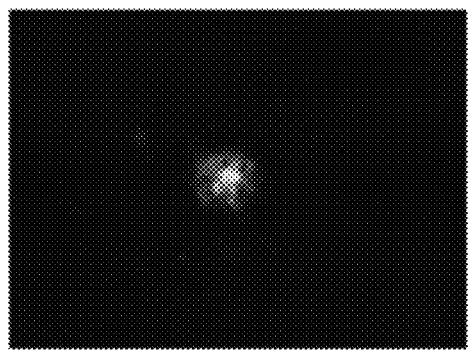

FIG. 53D represents the extent of neovascularization present in tissue receiving a combined therapy of aflibercept and a compound disclosed herein, stained with FITC-labeled *Griffonia simplicifolia* (GSA).

SUMMARY OF THE INVENTION

In some embodiments, the invention provides a compound of formula:

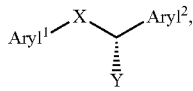

wherein: Aryl$^1$ is an aryl group which is substituted or unsubstituted; Aryl$^2$ is an aryl group which is substituted or unsubstituted; X is alkylene, alkenylene, alkynylene, an ether linkage, an amine linkage, an amide linkage, an ester linkage, a thioether linkage, a carbamate linkage, a carbonate linkage, a ureido linkage, a sulfone linkage, any of which is substituted or unsubstituted, or a chemical bond; and Y is H, aryl, heteroaryl, NH(aryl), NH(heteroaryl), NHSO$_2$R$^g$, or NHCOR$^g$, any of which is substituted or unsubstituted, or

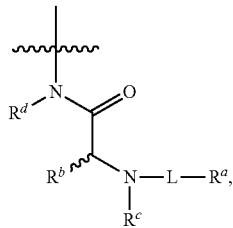

wherein: L is alkylene, alkenylene, or alkynylene, any of which is substituted or unsubstituted, or together with the nitrogen atom to which L is bound forms an amide linkage, a carbamate linkage, a ureido linkage, or a sulfonamide linkage, or a chemical bond, or together with any of R$^a$, R$^b$, R$^c$, and R$^d$ forms a ring that is substituted or unsubstituted; R$^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, R$^b$, R$^c$, and R$^d$ forms a ring that is substituted or unsubstituted; R$^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, R$^a$, R$^c$, and R$^d$ forms a ring that is substituted or unsubstituted; R$^c$ is H or alkyl which is substituted or unsubstituted, or together with any of L, R$^a$, R$^b$, and R$^d$ forms a ring that is substituted or unsubstituted; R$^d$ is H or alkyl which is substituted or unsubstituted, or together with any of L, R$^a$, R$^b$, and R$^c$ forms a ring that is substituted or unsubstituted; and R$^g$ is H, alkyl, alkenyl, alkynyl, aryl, arylalkyl, heterocyclyl, heterocyclylalkyl, heteroaryl, or heteroarylalkyl, any of which is substituted or unsubstituted, or a pharmaceutically-acceptable salt, tautomer, or zwitterion thereof.

In some embodiments, the invention provides a compound of formula:

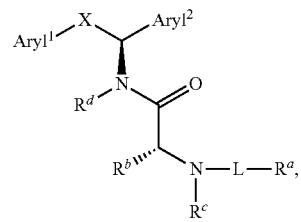

wherein:
Aryl$^1$ is an aryl group which is substituted or unsubstituted;
Aryl$^2$ is an aryl group which is substituted or unsubstituted;
X is alkylene, alkenylene, alkynylene, an ether linkage, an amine linkage, an amide linkage, an ester linkage, a thioether linkage, a carbamate linkage, a carbonate linkage, a ureido linkage, a sulfone linkage, any of which is substituted or unsubstituted, or a chemical bond; L is alkylene, alkenylene, or alkynylene, any of which is substituted or unsubstituted, or together with the nitrogen atom to which L is bound forms an amide linkage, a carbamate linkage, a ureido linkage, or a sulfonamide linkage, or a chemical bond, or together with any of R$^a$, R$^b$, R$^c$, and R$^d$ forms a ring that is substituted or unsubstituted; R$^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, R$^b$, R$^c$, and R$^d$ forms a ring that is substituted or unsubstituted; R$^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, R$^a$, R$^c$, and R$^d$ forms a ring that is substituted or unsubstituted; R$^c$ is H or alkyl which is substituted or unsubstituted, or together with any of L, R$^a$, R$^b$, and R$^d$ forms a ring that is substituted or unsubstituted; R$^d$ is H or alkyl which is substituted or unsubstituted, or together with any of L, R$^a$, R$^b$, and R$^c$ forms a ring that is substituted or unsubstituted; and R$^g$ is H, alkyl, alkenyl, alkynyl, aryl, arylalkyl, heterocyclyl, heterocyclylalkyl, heteroaryl, or heteroarylalkyl, any of which is substituted or unsubstituted, or a pharmaceutically-acceptable salt, tautomer, or zwitterion thereof.

In some embodiments, the invention provides a pharmaceutical composition comprising two Tie-2 activators, wherein the two Tie-2 activators are stereoisomers of one another, wherein the pharmaceutical composition is in a unit dosage form.

In some embodiments, the invention provides a pharmaceutical composition comprising a Tie-2 activator and a stereoisomer of the Tie-2 activator, wherein the stereoisomer activates Tie-2 with a potency that is from about 0.001% to about 100% the potency of the Tie-2 activator.

In some embodiments, the invention provides a method comprising contacting with a reaction mixture a compound of formula:

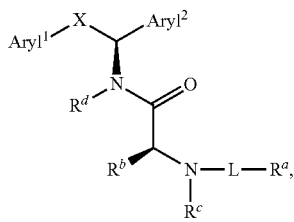

wherein:
Aryl$^1$ is an aryl group which is substituted or unsubstituted;
Aryl$^2$ is an aryl group which is substituted or unsubstituted;
X is alkylene, alkenylene, alkynylene, an ether linkage, an amine linkage, an amide linkage, an ester linkage, a thioether linkage, a carbamate linkage, a carbonate linkage, a ureido linkage, a sulfone linkage, any of which is substituted or unsubstituted, or a chemical bond; L is alkylene, alkenylene, or alkynylene, any of which is substituted or unsubstituted, or together with the nitrogen atom to which L is bound forms an amide linkage, a carbamate linkage, a ureido linkage, or a sulfonamide linkage, or a chemical bond, or together with any of R$^a$, R$^b$, R$^c$, and R$^d$ forms a ring that is substituted or unsubstituted; R$^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, R$^b$, R$^c$, and R$^d$ forms a ring that is substituted or unsubstituted; R$^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, R$^a$, R$^c$, and R$^d$ forms a ring that is substituted or unsubstituted; R$^c$ is H or alkyl which is substituted or unsubstituted, or together with any of L, R$^a$, R$^b$, and R$^d$ forms a ring that is substituted or unsubstituted; R$^d$ is H or alkyl which is substituted or unsubstituted, or together with any of L, R$^a$, R$^b$, and R$^c$ forms a ring that is substituted or unsubstituted; and R$^g$ is H, alkyl, alkenyl, alkynyl, aryl, arylalkyl, heterocyclyl, heterocyclylalkyl, heteroaryl, or heteroarylalkyl, any of which is substituted or unsubstituted, or a salt, tautomer, or zwitterion thereof, wherein a stereocenter of the compound or salt thereof inverts, thereby providing a stereoisomer of the compound or a salt, tautomer, or zwitterion of the stereoisomer.

DETAILED DESCRIPTION

Provided herein are compounds and methods of treating ocular disorders that are characterized by vascular instability, vascular leakage, and neovascularization. HPTP-β is a member of the receptor-like family of the protein tyrosine phosphatases (PTPases). HPTP-β is a transmembrane protein found primarily in endothelial cells that displays structural and functional similarity to cell adhesion molecules (CAMs). HPTP-β is unique among receptor-like PTPases in that it contains a single catalytic domain. One of the main functions of HPTP-β is to regulate Tie-2 negatively.

Tie-2 is a receptor tyrosine kinase found almost exclusively in endothelial cells. The principle regulators of Tie-2 phosphorylation are Angiopoietin-1 (Ang-1) and Angiopoietin-2 (Ang-2). Upon Ang-1 binding to Tie-2, the level of Tie-2 receptor phosphorylation increases. The duration of Tie-2 receptor phosphorylation is regulated by HPTP-β, which cleaves off the phosphate. Tie-2 receptor phosphorylation helps maintain endothelial cell proximity; therefore, the duration of Tie-2 receptor phosphorylation is an important determinant of endothelial cell proximity. For example, when severe inflammation occurs, the capillary endothelial cells separate, allowing proteins to enter the interstitial space. Separation of the capillary endothelial cells, and subsequent leak of proteins in the interstitial space, is known as vascular leak, and can lead to dangerous hypotension, edema, hemoconcentration, and hypoalbuminemia.

The present disclosure relates to compositions and methods for treating conditions, such as ocular diseases, wherein neovasculatization and vascular leakage can be present. These diseases can display an elevated angiogenic response in ocular vessels. The present disclosure describes HPTP-β inhibitors that can provide vascular stabilization.

Human Protein Tyrosine Phosphatase-Beta (HPTP-β) Inhibitors.

Compounds disclosed herein can be effective as Tie-2 activators. The compounds can effect that activity, for example, by binding to or inhibiting HPTP-β. Such compounds can bind to HPTP-β, for example, by mimicking the binding mechanism of a native substrate, such as a phosphorylated compound. A compound can be a phosphate mimetic or bioisostere, for example, a sulfamic acid. The compound could also be derived from an amino acid building block or comprise an amino acid backbone for efficiency and economy of synthesis.

In some embodiments, a compound of the invention is a compound of the formula:

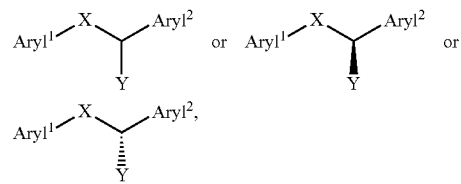

wherein:
Aryl$^1$ is an aryl group which is substituted or unsubstituted;
Aryl$^2$ is an aryl group which is substituted or unsubstituted;
X is alkylene, alkenylene, alkynylene, an ether linkage, an amine linkage, an amide linkage, an ester linkage, a thioether linkage, a carbamate linkage, a carbonate linkage, a ureido linkage, a sulfone linkage, any of which is substituted or unsubstituted, or a chemical bond; and Y is H, aryl, heteroaryl, NH(aryl), NH(heteroaryl), NHSO$_2$R$^g$, or NHCOR$^g$, any of which is substituted or unsubstituted, or

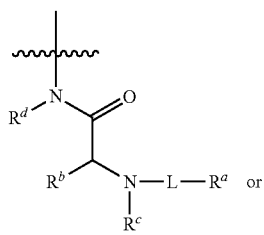

or

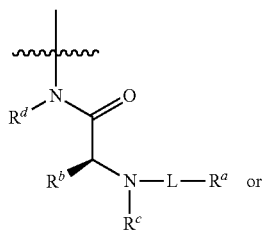

or

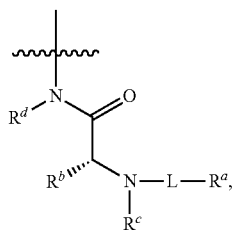

wherein:

L is alkylene, alkenylene, or alkynylene, any of which is substituted or unsubstituted, or together with the nitrogen atom to which L is bound forms an amide linkage, a carbamate linkage, a ureido linkage, or a sulfonamide linkage, or a chemical bond, or together with any of $R^a$, $R^b$, $R^c$, and $R^d$ forms a ring that is substituted or unsubstituted; $R^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, $R^b$, $R^c$, and $R^d$ forms a ring that is substituted or unsubstituted; $R^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, $R^a$, $R^c$, and $R^d$ forms a ring that is substituted or unsubstituted; $R^c$ is H or alkyl which is substituted or unsubstituted, or together with any of L, $R^a$, $R^b$, and $R^d$ forms a ring that is substituted or unsubstituted; $R^d$ is H or alkyl which is substituted or unsubstituted, or together with any of L, $R^a$, $R^b$, and $R^c$ forms a ring that is substituted or unsubstituted; and $R^g$ is H, alkyl, alkenyl, alkynyl, aryl, arylalkyl, heterocyclyl, heterocyclylalkyl, heteroaryl, or heteroarylalkyl, any of which is substituted or unsubstituted, or a pharmaceutically-acceptable salt, tautomer, or zwitterion thereof.

In some embodiments, aryl[1] is substituted or unsubstituted phenyl, aryl[2] is substituted or unsubstituted heteroaryl, and X is alkylene. In some embodiments, aryl[1] is substituted phenyl, aryl[2] is substituted heteroaryl, and X is methylene.

In some embodiments, a compound is of the formula:

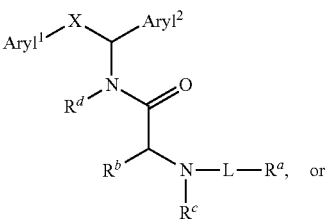

or

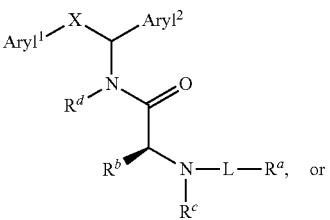

or

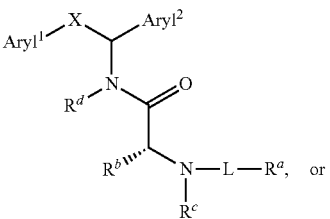

or

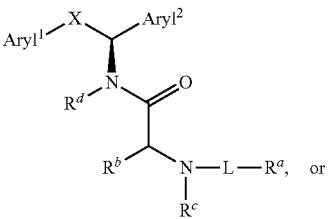

or

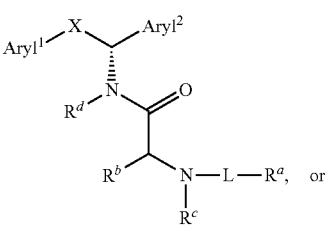

or

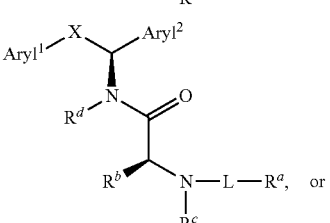

or

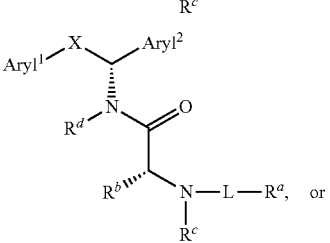

or

-continued

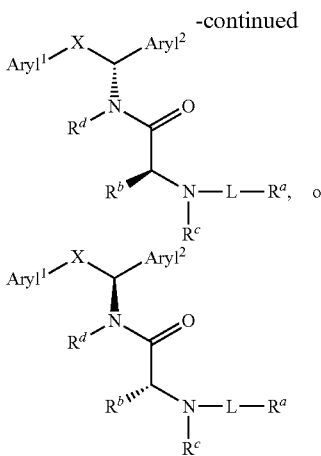

wherein aryl¹ is para-substituted phenyl, aryl² is substituted heteroaryl; X is methylene; L is alkylene, alkenylene, or alkynylene, any of which is substituted or unsubstituted, or together with the nitrogen atom to which L is bound forms an amide linkage, a carbamate linkage, a ureido linkage, or a sulfonamide linkage, or a chemical bond; $R^a$ is H, alkyl, alkenyl, alkynyl, aryl, arylalkyl, heterocyclyl, heterocyclylalkyl, heteroaryl, or heteroarylalkyl, any of which is substituted or unsubstituted; $R^b$ is H, alkyl, alkenyl, alkynyl, aryl, arylalkyl, heterocyclyl, heterocyclylalkyl, heteroaryl, or heteroarylalkyl, any of which is substituted or unsubstituted; $R^c$ is H or alkyl which is substituted or unsubstituted; and $R^d$ is H or alkyl which is substituted or unsubstituted.

In some embodiments, aryl¹ is para-substituted phenyl; aryl² is a substituted thiazole moiety; X is methylene; L together with the nitrogen atom to which L is bound forms a carbamate linkage; $R^a$ is alkyl, which is substituted or unsubstituted; $R^b$ is arylalkyl, which is substituted or unsubstituted; $R^c$ is H; and $R^d$ is H.

In some embodiments, Aryl² is:

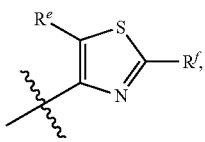

wherein $R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a ureido group, a thioether group, a thioester group, a thioacid group, aryl, arylalkyl, heterocyclyl, heterocyclylalkyl, heteroaryl, or heteroarylalkyl, any of which is substituted or unsubstituted; and $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a ureido group, a thioether group, a thioester group, a thioacid group, aryl, arylalkyl, heterocyclyl, heterocyclylalkyl, heteroaryl, or heteroarylalkyl, any of which is substituted or unsubstituted.

In some embodiments, $R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and $R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted. In some embodiments, $R^e$ is H, OH, F, Cl, Br, I, alkyl, or an alkoxy group, any of which is substituted or unsubstituted and $R^f$ is alkyl, aryl, heterocyclyl, or heteroaryl, any of which is substituted or unsubstituted. In some embodiments, aryl¹ is 4-phenylsulfamic acid; $R^a$ is alkyl, which is substituted or unsubstituted; $R^b$ is arylalkyl, which is substituted or unsubstituted; $R^e$ is H; and $R^f$ is heteroaryl. In some embodiments, aryl¹ is 4-phenylsulfamic acid; $R^a$ is alkyl; which is substituted or unsubstituted; $R^b$ is arylalkyl, which is substituted or unsubstituted; $R^e$ is H; and $R^f$ is alkyl In some embodiments, Aryl² is:

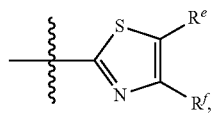

wherein $R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a ureido group, a thioether group, a thioester group, a thioacid group, aryl, arylalkyl, heterocyclyl, heterocyclylalkyl, heteroaryl, or heteroarylalkyl, any of which is substituted or unsubstituted, $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a ureido group, a thioether group, a thioester group, a thioacid group, aryl, arylalkyl, heterocyclyl, heterocyclylalkyl, heteroaryl, or heteroarylalkyl, any of which is substituted or unsubstituted. In some embodiments, $R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and $R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted. In some embodiments, $R^e$ is H, OH, F, Cl, Br, I, alkyl, or an alkoxy group, any of which is substituted or unsubstituted; and $R^f$ is alkyl, aryl, heterocyclyl, or heteroaryl, any of which is substituted or unsubstituted. In some embodiments, aryl¹ is 4-phenylsulfamic acid; $R^a$ is alkyl, which is substituted or unsubstituted; $R^b$ is arylalkyl, which is substituted or unsubstituted; $R^e$ is H; and $R^f$ is heteroaryl.

In some embodiments, a substituted phenyl group is:

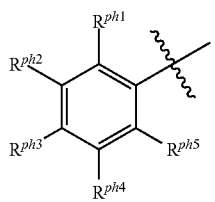

wherein:
each of $R^{ph1}$, $R^{ph2}$, $R^{ph3}$, $R^{ph4}$, and $R^{ph5}$ is independently H, OH, F, Cl, Br, I, CN, sulfamic acid, tosylate, mesylate, triflate, besylate, alkyl, alkenyl, alkynyl, an alkoxy group, a sulfhydryl group, a nitro group, a nitroso group, an azido group, a sulfoxide group, a sulfone group, a sulfonamide group, an ether group, a carboxylic acid group, a carboxaldehyde group, an ester group, an amine group, an amide group, a carbonate group, a carbamate group, a ureido group, a thioether group, a thioester group, a thioacid group, aryl, arylalkyl, heterocyclyl, heterocyclylalkyl, heteroaryl, or heteroarylalkyl.

Illustrative compounds include the following:

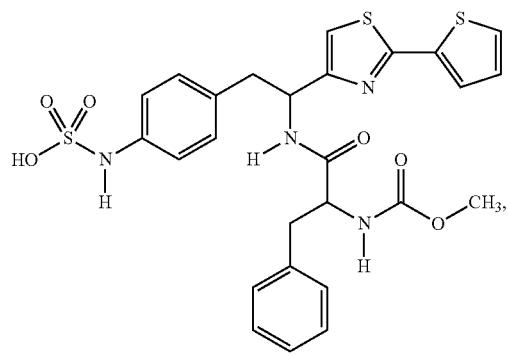

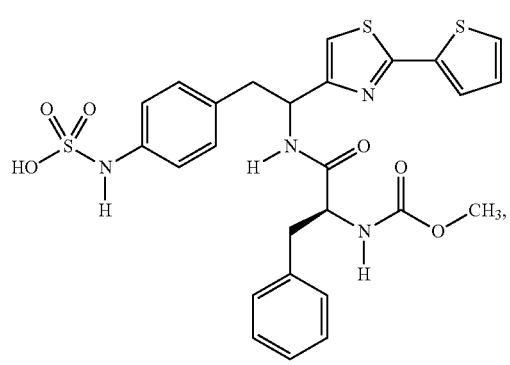

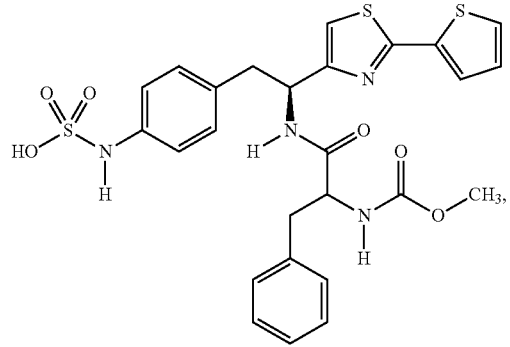

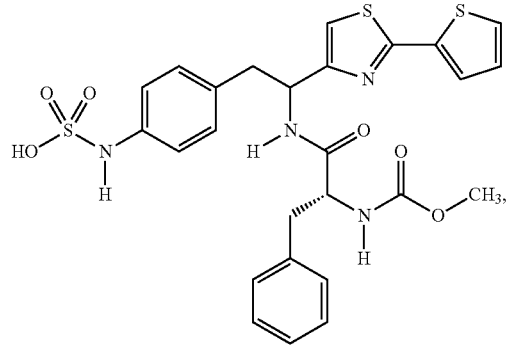

-continued

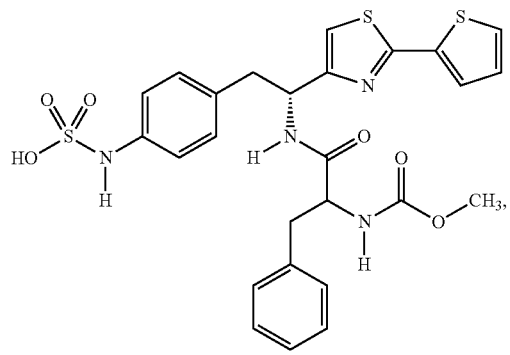

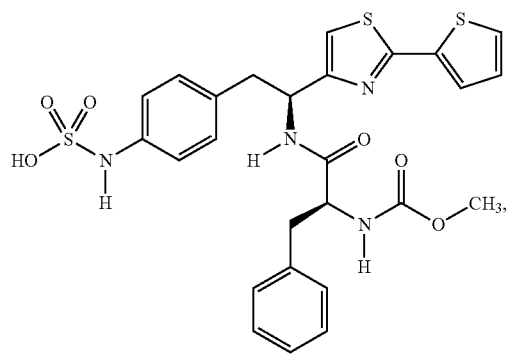

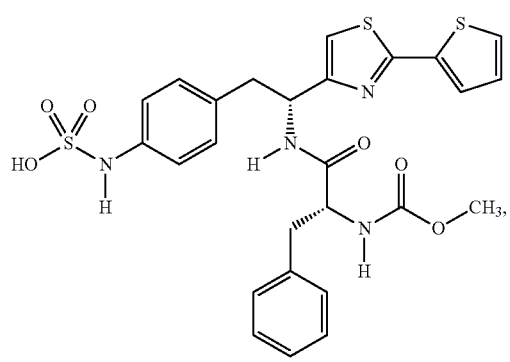

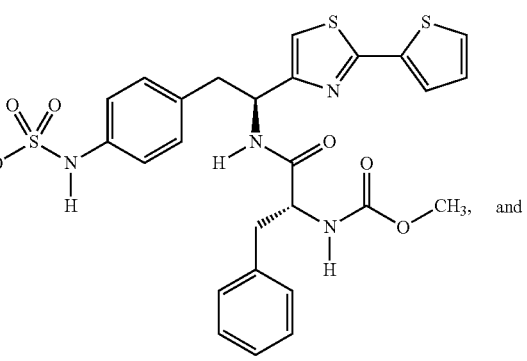

and

-continued

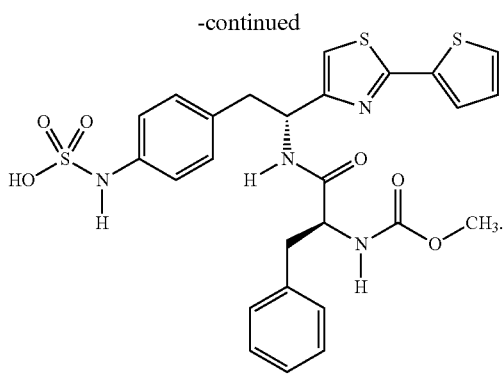

Optional Substituents for Chemical Groups.

Non-limiting examples of optional substituents include hydroxyl groups, sulfhydryl groups, halogens, amino groups, nitro groups, nitroso groups, cyano groups, azido groups, sulfoxide groups, sulfone groups, sulfonamide groups, carboxyl groups, carboxaldehyde groups, imine groups, alkyl groups, halo-alkyl groups, alkenyl groups, halo-alkenyl groups, alkynyl groups, halo-alkynyl groups, alkoxy groups, aryl groups, aryloxy groups, aralkyl groups, arylalkoxy groups, heterocyclyl groups, acyl groups, acyloxy groups, carbamate groups, amide groups, ureido groups, and ester groups.

Non-limiting examples of alkyl and alkylene groups include straight, branched, and cyclic alkyl and alkylene groups. An alkyl group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of cyclic alkyl groups include cyclopropyl, cyclobutyl, cyclopentyl, cyclohexyl, cycloheptyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl.

An aryloxy group can be, for example, an oxygen atom substituted with any aryl group, such as phenoxy.

An aralkyl group can be, for example, any alkyl group substituted with any aryl group, such as benzyl.

An arylalkoxy group can be, for example, an oxygen atom substituted with any aralkyl group, such as benzyloxy.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

An acyl group can be, for example, a carbonyl group substituted with hydrocarbyl, alkyl, hydrocarbyloxy, alkoxy, aryl, aryloxy, aralkyl, arylalkoxy, or a heterocycle. Non-limiting examples of acyl include acetyl, benzoyl, benzyloxycarbonyl, phenoxycarbonyl, methoxycarbonyl, and ethoxycarbonyl.

An acyloxy group can be an oxygen atom substituted with an acyl group. An ester or an ester group comprises an acyloxy group. A non-limiting example of an acyloxy group, or an ester group, is acetate.

A carbamate group can be an oxygen atom substituted with a carbamoyl group, wherein the nitrogen atom of the carbamoyl group is unsubstituted, monosubstituted, or disubstituted with one or more of hydrocarbyl, alkyl, aryl, heterocyclyl, or aralkyl. When the nitrogen atom is disubstituted, the two substituents together with the nitrogen atom can form a heterocycle.

A compound described herein can be at least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure on a chemical, optical, isomeric, enantiomeric, or diastereomeric basis. Purity can be assessed, for example, by HPLC, MS, LC/MS, melting point, or NMR.

Pharmaceutically-Acceptable Salts.

The invention provides the use of pharmaceutically-acceptable salts of any compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate salt, an ethanesulfonate salt, a benzenesulfonate salt, a p-toluenesulfonate salt, a citrate salt, an oxalate salt, or a maleate salt.

Optical Activity.

Optical activity is the ability of a chiral molecule to rotate a plane of polarized light. Molecules that can rotate a beam of light are optically active. Those that rotate light clockwise are dextrorotatory, and those that rotate light counterclockwise are levorotatory. If only one enantiomer is present in a sample, the sample is optically pure. When both enatiomers are present in equal amounts, the effects of optical rotation sum to zero. If a mixture of enantiomers is present, but one enatiomer is in excess, the sample is optically active.

Optical activity can be measured using a polarimeter, which determines the specific rotation of a substance based upon the temperature, wavelength of light used, and concentration of the substance, expressed as the angle to which the material causes polarized light to rotate. A polarimeter holds a sample tube, through which light is passed via a polarizing filter. The analyzing lens is rotated such that the light is visible to the user; the amount (expressed in degrees) that the lens must be rotated to make the light visible is known as the observed rotation, and is used to calculate the specific rotation of the sample being tested.

The specific rotation of a sample can be about +1, about −1, about +2°, about −2°, about +3°, about −3°, about +4°, about −4°, about +5°, about −5°, about +6°, about −60, about +7°, about −7°, about +8°, about −8°, about +9°, about −9°, about +10°, about −10°, about +11°, about −11°, about +12°, about −12°, about +13°, about −13°, about +14°, about 14°, about +15°, about −15°, about +16°, about −16°, about +17°, about −17°, about +18°, about −18°, about +19°, about −19°, about +20°, about −20°, about +21°, about −21°, about +22°, about −22°, about +23°, about −23°, about +24°, about −24°, about +25°, about −25°, about +26°, about −26°, about +27°, about −27°, about +28°, about −28°, about +29°, about −29°, about +30°, about −30°, about +40°, about −40°, about +50°, about −50°, about +60°, about −60°, about +70°, about −70°, about +80°, about −80°, about +90°, about −90°, about +100°, about −100°, about +110°, about −110°, about +120°, about −120°, about +130°, about −130°, about +140°, about −140°, about +150°, about −150°, about +160°, about −160°, about +170°, about −170°, about +180°, about −180°, about +190°, about −190°, about +200°, about −200°, about +210°, about −210°, about +220°, about −220°, about +230°, about −230°, about +240°, about −240°, about +250°, about −250°, about +260°, about −260°, about +270°, about −270°, about +280°, about −280°, about +290°, about −290°, about +300°, about −300°, about +310°, about −310°, about +320°, about −320°, about +330°, about −330°, about +340°, about −340°, about +350°, about −350°, about +360°, or about −360°.

Circular dichroism (CD) is the difference in absorption of left-handed circularly polarised light (L-CPL) and right-handed circularly polarised light (R-CPL), and occurs when a molecule contains one or more chiral light-absorbing groups. Optically active chiral molecules preferentially absorb one direction of the polarized light, causing differently polarized light beams to travel through an optically active medium with different velocities.

In some embodiments, the pharmaceutical composition disclosed herein contains a mixture of stereoisomers. A stereoisomer can be present as a percentage of the total mixture of about 0.0001%, about 0.0005%, about 0.001%, about 0.005%, about 0.01%, about 0.05%, about 0.1%, about 0.5%, about 1%, about 2%, about 3%, about 4%, about 5%, about 6%, about 7%, about 8%, about 9%, about 10%, about 15%, about 20%, about 25%, about 30%, about 35%, about 40%, about 45%, or about 50%.

Optical activity of a sample can change, for example, through the racemization, epimerization, or inversion of stereocenters of compounds in the same. For example, if a compound of the following formula:

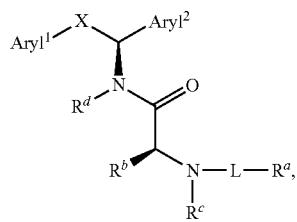

is subjected to suitable reaction conditions or contacted with a suitable reagent or catalyst, then a stereocenter of the compound can change, for example, to provide a compound of any of the following formulae, or a mixture thereof:

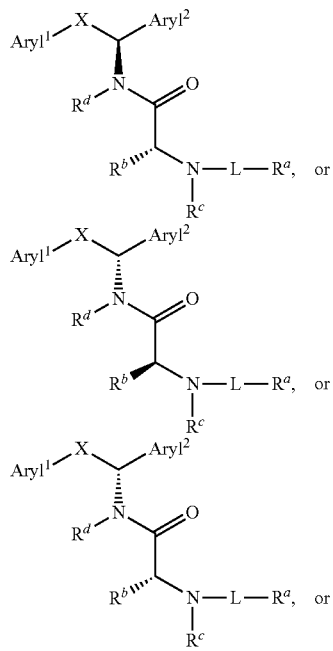

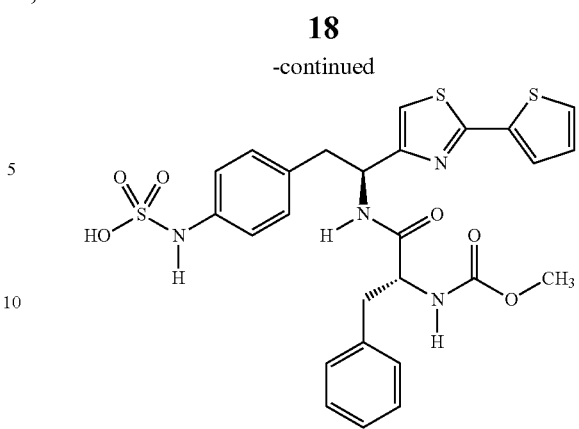

or a stereoisomer, tautomer, or salt thereof.

A compound having a stereocenter and a starting material having a stereocenter can be coupled together under suitable reaction conditions or in the presence of a suitable reagent or catalyst, and undergo inversion of one or more stereocenters during the reaction. For example, a compound of formula:

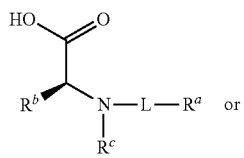

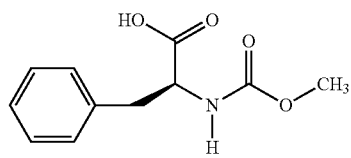

can be coupled to a starting material of formula:

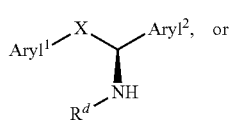

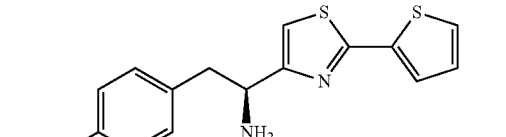

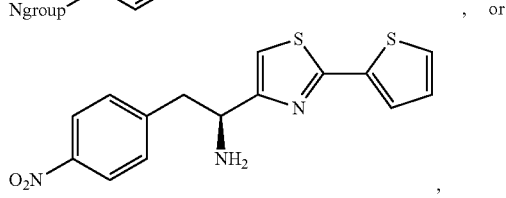

wherein N group is a functional group that contains a nitrogen atom, to provide a product of formula:

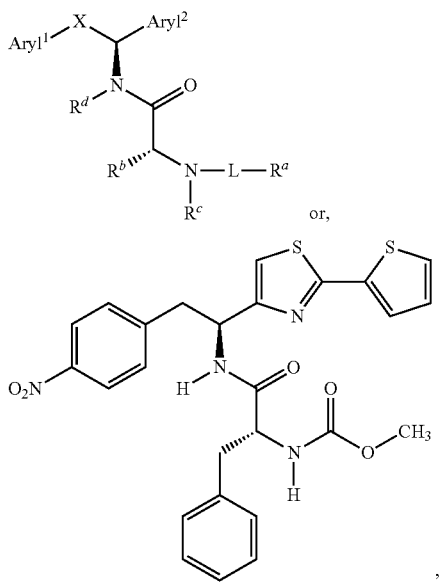

or a stereoisomer, tautomer, or salt thereof.

Nonlimiting examples of suitable reagents and catalysts include acids, bases, coupling agents, and additives. Nonlimiting examples of acids include hydrochloric acid, hydrobromic acid, hydroiodic acid, nitric acid, nitrous acid, sulfuric acid, sulfurous acid, a phosphoric acid, tartaric acid, acetic acid, succinic acid, methanesulfonic acid, ethanesulfonic acid, benzenesulfonic acid, p-toluenesulfonic acid, citric acid, and triflic acid. Non-limiting examples of bases include lithium hydroxide, sodium hydroxide, potassium hydroxide, lithium alkoxide, sodium alkoxide, potassium alkoxide, lithium methoxide, sodium methoxide, potassium methoxide, lithium ethoxide, sodium ethoxide, potassium ethoxide, lithium isopropoxide, sodium isopropoxide, potassium isopropoxide, lithium carbonate, sodium carbonate, potassium carbonate, lithium bicarbonate, sodium bicarbonate, potassium bicarbonate, lithium phosphate, sodium phosphate, potassium phosphate, dilithium phosphate, disodium phosphate, dipotassium phosphate, trilithium phosphate, trisodium phosphate, tripotassium phosphate, ammonia, a trialkyl amine, ammonium hydroxide, trimethyl amine, triethyl amine, tribenzyl amine, diisopropylethyl amine, DBU, DBN, pyridine, imidazole, 2,6-lutidine, quinoline, 1,8-bis(dimethylamino)naphthylene, N-methylmorpholine, N-methylpiperidine, and dimethylaminopyridine. Non-limiting examples of coupling agents inclde DCC, DIC, EDCI, HBTU, TBTU, HATU, HCTU, BOP, PyBOP, PyAOP, PyBroP, TSTU, TOTU, TPTU, TDBTU, DEPBT, CDI, T3P, and pivaloyl chloride. Non-limiting examples of additives include silica, alumina, magnesium oxide, titanium oxide, zeolite, active carbon, montmorillonite, HOBt, and HOAt.

Antibodies.

Compounds of the invention can be co-formulated or co-administered with antibodies, for example, anti-VEGF agents. Non-limiting examples of such antibodies include ranibizumab, bevacizumab, and aflibercept.

An antibody can comprise a heavy chain and a light chain. In some embodiments, the heavy chain comprises SEQ ID NO: 1:

GluValGlnLeuValGluSerGlyGlyGlyLeuValGlnProGlyGly

SerLeuArgLeuSerCysAlaAlaSerGlyTyrAspPheThrHisTyr

GlyMetAsnTrpValArgGlnAlaProGlyLysGlyLeuGluTrpVal

GlyTrpIleAsnThrTyrThrGlyGluProThrTyrAlaAlaAspPhe

LysArgArgPheThrPheSerLeuAspThrSerLysSerThrAlaTyr

LeuGlnMetAsnSerLeuArgAlaGluAspThrAlaValTyrTyrCys

AlaLysTyrProTyrTyrTyrGlyThrSerHisTrpTyrPheAspVal

TrpGlyGlnGlyThrLeuValThrValSerSerAlaSerThrLysGly

ProSerValPheProLeuAlaProSerSerLysSerThrSerGlyGly

ThrAlaAlaLeuGlyCysLeuValLysAspTyrPheProGluProVal

ThrValSerTrpAsnSerGlyAlaLeuThrSerGlyValHisThrPhe

ProAlaValLeuGlnSerSerGlyLeuTyrSerLeuSerSerValVal

ThrValProSerSerSerLeuGlyThrGlnThrTyrIleCysAsnVal

AsnHisLysProSerAsnThrLysValAspLysLysValGluProLys

SerCysAspLysThrHisLeu.

In some embodiments, the heavy chain is SEQ ID NO: 1.
In some embodiments, the light chain comprises SEQ ID NO:2:

AspIleGlnLeuThrGlnSerProSerSerLeuSerAlaSerValGly

AspArgValThrIleThrCysSerAlaSerGlnAspIleSerAsnTyr

LeuAsnTrpTyrGlnGlnLysProGlyLysAlaProLysValLeuIle

TyrPheThrSerSerLeuHisSerGlyValProSerArgPheSerGly

SerGlySerGlyThrAspPheThrLeuThrIleSerSerLeuGlnPro

GluAspPheAlaThrTyrTyrCysGlnGlnTyrSerThrValProTrp

ThrPheGlyGlnGlyThrLysValGluIleLysArgThrValAlaAla

ProSerValPheIlePheProProSerAspGluGlnLeuLysSerGly

ThrAlaSerValValCysLeuLeuAsnAsnPheTyrProArgGluAla

LysValGlnTrpLysValAspAsnAlaLeuGlnSerGlyAsnSerGln

GluSerValThrGluGlnAspSerLysAspSerThrTyrSerLeuSer

SerThrLeuThrGlnSerSerGlyLeuTyrSerLeuSerSerValVal

ThrValProSerSerSerLeuGlyThrGlnThrTyrIleCysAsnVal

AsnHisLysProSerAsnThrLysValAspLysLysValGluProLys

SerCysAspLysThrHisLeu.

In some embodiments, the light chain is SEQ ID NO:2.
An antibody used herein can comprise one or both of SEQ ID NOs: 1 and 2. An antibody used herein can consist of one or both of SEQ ID NOs: 1 and 2.

Formulations.

The disclosed solubilizing systems can comprise one or more pharmaceutically acceptable agents, which alone or in combination solubilize a compound herein or a pharmaceutically acceptable salt thereof.

Alcohols.

A non-limiting example of a solubilizing agent includes an organic solvent. Non-limiting examples of organic solvents include alcohols, for example, $C_1$-$C_4$ linear alkyl, $C_3$-$C_4$ branched alkyl, ethanol, ethylene glycol, glycerin, 2-hydroxypropanol, propylene glycol, maltitol, sorbitol, xylitol; substituted or unsubstituted aryl, and benzyl alcohol. Cyclodextrins.

Non-limiting examples of cyclodextrins include β-cyclodextrin, methyl β-cyclodextrin, 2-hydroxypropyl-β-cyclodextrin, sulfobutyl ether-β-cyclodextrin sodium salt, and 2-hydroxypropyl-β-cyclodextrin. A cyclodextrin can possess a large cyclic structure with a channel passing through the center of the structure. The interior of the cyclodextrin can be hydrophobic, and interact favorably with hydrophobic molecules. The exterior of the cyclodextrin can be highly hydrophilic owing to the several hydroxyl groups exposed to bulk solvent. Capture of a hydrophobic molecule, such as a compound disclosed herein, in the channel of the cyclodextrin can result in the formation of a complex stabilized by non-covalent hydrophobic interactions. The complex can be soluble in water, and carry the captured hydrophobic molecule into the bulk solvent.

The disclosed solubilizing systems comprise 2-hydroxypropyl-beta-cyclodextrin (HPβ-CD). 2-Hydroxypropyl-β-cyclodextrin [CAS No. 128446-35-5] is commercially available as Cavitron™. 2-Hydroxypropyl-β-cyclodextrin, also described known as hydroxypropyl-β-cyclodextrin, 2-hydroxypropyl-beta-cyclodextrin, hydroxypropyl-beta-cyclodextrin or HPβCD, can be represented by either of the following formulae:

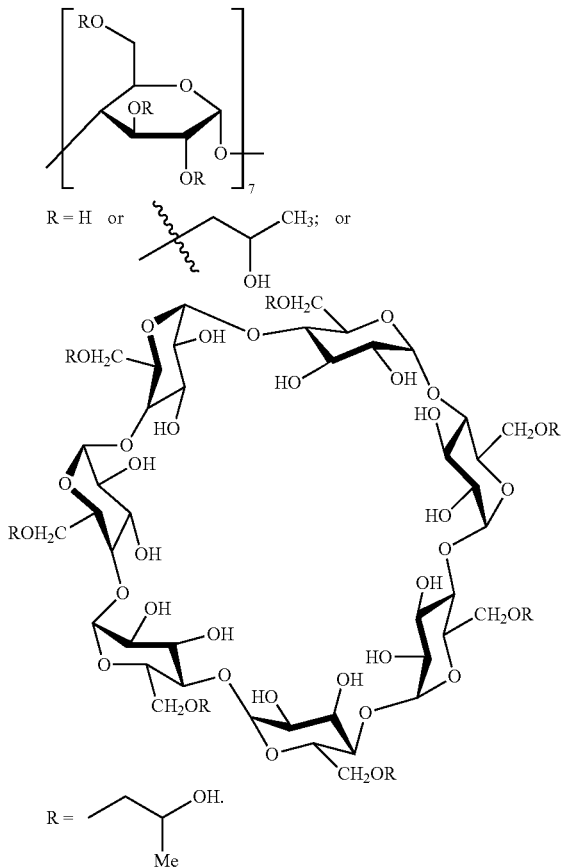

The average molecular weight of Cavitron™, is approximately 1396 Da, wherein the average degree of substitution is from about 0.5 to about 1.3 units of 2-hydroxypropyl per ring glucose unit.

In one embodiment, a formulation disclosed herein can comprise a ratio of about 20 parts of a compound herein or a pharmaceutically acceptable salt thereof to about 1 part solubilizing system (about 20:about 1), to about 1 part of the compound herein or a pharmaceutically acceptable salt thereof to about 20 parts solubilizing system (about 1:about 20). For example, a formulation containing about 100 mg of a compound herein or a pharmaceutically acceptable salt thereof can contain from about 5 mg to about 2000 mg of a solubilizing agent, such as a cyclodextrin. In another embodiment, the ratio can be based on number, or moles, or compound compared to number, or moles, of the solubilizing system.

The following are non-limiting examples of ratios of a compound herein and a solubilizing agent, such as a cyclodextrin. The following examples alternatively describe the ratio of a solubilizing agent, such as a cyclodextrin, and a compound herein. The ratio can be: about 20:about 1; about 19.9:about 1; about 19.8:about 1; about 19.7:about 1; about 19.6:about 1; about 19.5:about 1; about 19.4:about 1; about 19.3:about 1; about 19.2:about 1; about 19.1:about 1; about 19:about 1; about 18.9:about 1; about 18.8:about 1; about 18.7:about 1; about 18.6:about 1; about 18.5:about 1; about 18.4:about 1; about 18.3:about 1; about 18.2:about 1; about 18.1:about 1; about 18:about 1; about 17.9:about 1; about 17.8:about 1; about 17.7:about 1; about 17.6:about 1; about 17.5:about 1; about 17.4:about 1; about 17.3:about 1; about 17.2:about 1; about 17.1:about 1; about 17:about 1; about 16.9:about 1; about 16.8:about 1; about 16.7:about 1; about 16.6:about 1; about 16.5:about 1; about 16.4:about 1; about 16.3:about 1; about 16.2:about 1; about 16.1:about 1; about 16:about 1; about 15.9:about 1; about 15.8:about 1; about 15.7:about 1; about 15.6:about 1; about 15.5:about 1; about 15.4:about 1; about 15.3:about 1; about 15.2:about 1; about 15.1:about 1; about 15:about 1; about 14.9:about 1; about 14.8:about 1; about 14.7:about 1; about 14.6:about 1; about 14.5:about 1; about 14.4:about 1; about 14.3:about 1; about 14.2:about 1; about 14.1:about 1; about 14:about 1; about 13.9:about 1; about 13.8:about 1; about 13.7:about 1; about 13.6:about 1; about 13.5:about 1; about 13.4:about 1; about 13.3:about 1; about 13.2:about 1; about 13.1:about 1; about 13:about 1; about 12.9:about 1; about 12.8:about 1; about 12.7:about 1; about 12.6:about 1; about 12.5:about 1; about 12.4:about 1; about 12.3:about 1; about 12.2:about 1; about 12.1:about 1; about 12:about 1; about 11.9:about 1; about 11.8:about 1; about 11.7:about 1; about 11.6:about 1; about 11.5:about 1; about 11.4:about 1; about 11.3:about 1; about 11.2:about 1; about 11.1:about 1; about 11:about 1; about 10.9:about 1; about 10.8:about 1; about 10.7:about 1; about 10.6:about 1; about 10.5:about 1; about 10.4:about 1; about 10.3:about 1; about 10.2:about 1; about 10.1:about 1; about 10:about 1; about 9.9:about 1; about 9.8:about 1; about 9.7:about 1; about 9.6:about 1; about 9.5:about 1; about 9.4:about 1; about 9.3:about 1; about 9.2:about 1; about 9.1:about 1; about 9:about 1; about 8.9:about 1; about 8.8:about 1; about 8.7:about 1; about 8.6:about 1; about 8.5:about 1; about 8.4:about 1; about 8.3:about 1; about 8.2:about 1; about 8.1:about 1; about 8:about 1; about 7.9:about 1; about 7.8:about 1; about 7.7:about 1; about 7.6:about 1; about 7.5:about 1; about 7.4:about 1; about 7.3:about 1; about 7.2:about 1; about 7.1:about 1; about 7:about 1; about 6.9:about 1; about 6.8:about 1; about 6.7:about 1; about 6.6:about 1; about 6.5:about 1; about 6.4:about 1; about 6.3:about 1; about 6.2:about 1; about 6.1:about 1; about 6:about 1; about 5.9:about 1; about 5.8:about 1; about 5.7:about 1; about 5.6:about 1; about 5.5:about 1; about 5.4:about 1; about 5.3:about 1; about 5.2:about 1; about 5.1:about 1; about 5:about 1; about 4.9:about 1; about 4.8:about 1; about 4.7:about 1; about 4.6:about 1; about 4.5:about 1; about 4.4:about 1; about 4.3:about 1; about 4.2:about 1; about 4.1:about 1; about 4:about 1; about 3.9:about 1; about 3.8:about 1; about 3.7:about 1; about 3.6:about 1; about 3.5:about 1; about 3.4:about 1; about 3.3:about 1; about 3.2:about 1; about 3.1:about 1; about 3:about 1; about 2.9:about 1; about 2.8:about 1; about 2.7:about 1; about 2.6:about 1; about 2.5:about 1; about 2.4:about 1; about 2.3:about 1; about 2.2:about 1; about 2.1:about 1; about 2:about 1; about 1.9:about 1; about 1.8:about 1; about 1.7:about 1; about 1.6:about 1; about 1.5:about 1; about 1.4:about 1; about 1.3:about 1; about 1.2:about 1; about 1.1:about 1; or about 1:about 1.

Polyvinylpyrrolidone.

Another non-limiting example of a solubilizing agent is polyvinylpyrrolidone (PVP), having the formula:

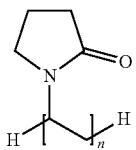

wherein the index n is from about 40 to about 200. PVP's can have an average molecular weight from about 5500 to about 28,000 g/mol. One non-limiting example is PVP-10, having an average molecular weight of approximately 10,000 g/mol.

Polyakyleneoxides and Ethers Thereof.

Another non-limiting example of solubilizing agents includes polyalkyleneoxides, and polymers of alcohols or polyols. Polymers can be mixed, or contain a single monomeric repeat subunit. For example, polyethylene glycols having an average molecular weight of from about 200 to about 20,000, for example, PEG 200, PEG 400, PEG 600, PEG 1000, PEG 1450, PEG 1500, PEG 4000, PEG 4600, and PEG 8000. In a same embodiment, a composition comprises one or more polyethylene glycols chosen from PEG 400, PEG 1000, PEG 1450, PEG 4600 and PEG 8000.

Other polyalkyleneoxides are polypropylene glycols having the formula:

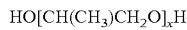

wherein the index x represents the average number of propyleneoxy units in the polymer. The index x can be represented by a whole number or a fraction. For example, a polypropylene glycol having an average molecular weight of 8,000 g/mole (PEG 8000) can be represented by the formulae:

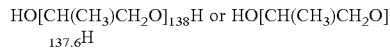

or the polypropylene glycol can be represented by the common, short hand notation: PEG 8000.

Another example of polypropylene glycols can have an average molecular weight from about 1200 g/mol to about 20,000 g/mol, i.e., a polypropylene glycol having an average molecular weight of about 8,000 g/mol, for example, PEG 8000.

Another solubilizing agent is Polysorbate 80 (Tween™ 80), which is an oleate ester of sorbitol and its anhydrides copolymerized with approximately 20 moles of ethylene oxide for each mole of sorbitol and sorbitol anhydrides. Polysorbate 80 is made up of sorbitan mono-9-octadecanoate poly(oxy-1,2-ethandiyl) derivatives.

Solubilizing agents also include poloxamers having the formula:

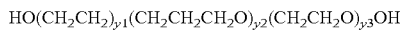

which are nonionic block copolymers composed of a polypropyleneoxy unit flanked by two polyethyleneoxy units. The indices $y^1$, $y^2$, and $y^3$ have values such that the poloxamer has an average molecular weight of from about 1000 g/mol to about 20,000 g/mol.

In some embodiments, a compound or pharmaceutically-acceptable salt thereof is present in a formulation in an amount of about 0.1 mg/mL to about 100 mg/mL, about 0.1 mg/mL to about 1 mg/mL, about 0.1 mg/mL to about 5 mg/mL, about 5 mg/mL to about 10 mg/mL, about 10 mg/mL to about 15 mg/mL, about 15 mg/mL to about 20 mg/mL, about 20 mg/mL to about 25 mg/mL, about 25 mg/mL to about 30 mg/mL, about 30 mg/mL to about 35 mg/mL, about 35 mg/mL to about 40 mg/mL, about 40 mg/mL to about 45 mg/mL, about 45 mg/mL to about 50 mg/mL, about 50 mg/mL to about 55 mg/mL, about 55 mg/mL to about 60 mg/mL, about 60 mg/mL to about 65 mg/mL, about 65 mg/mL to about 70 mg/mL, about 70 mg/mL to about 75 mg/mL, about 75 mg/mL to about 80 mg/mL, about 80 mg/mL to about 85 mg/mL, about 85 mg/mL to about 90 mg/mL, about 90 mg/mL to about 95 mg/mL, or about 95 mg/mL to about 100 mg/mL.

In some embodiments, a compound or pharmaceutically-acceptable salt thereof is present in a formulation in an amount of about 1 mg/mL, about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL about 12 mg/mL, about 13 mg/mL, about 14 mg/mL, about 15 mg/mL, about 16 mg/mL, about 17 mg/mL, about 18 mg/mL, about 19 mg/mL, about 20 mg/mL, about 21 mg/mL about 22 mg/mL, about 23 mg/mL, about 24 mg/mL, about 25 mg/mL, about 26 mg/mL, about 27 mg/mL, about 28 mg/mL, about 29 mg/mL, about 30 mg/mL, about 31 mg/mL about 32 mg/mL, about 33 mg/mL, about 34 mg/mL, about 35 mg/mL, about 36 mg/mL, about 37 mg/mL, about 38 mg/mL, about 39 mg/mL, about 40 mg/mL, about 41 mg/mL about 42 mg/mL, about 43 mg/mL, about 44 mg/mL, about 45 mg/mL, about 46 mg/mL, about 47 mg/mL, about 48 mg/mL, about 49 mg/mL, about 50 mg/mL, about 51 mg/mL about 52 mg/mL, about 53 mg/mL, about 54 mg/mL, about 55 mg/mL, about 56 mg/mL, about 57 mg/mL, about 58 mg/mL, about 59 mg/mL, about 60 mg/mL, about 61 mg/mL about 62 mg/mL, about 63 mg/mL, about 64 mg/mL, about 65 mg/mL, about 66 mg/mL, about 67 mg/mL, about 68 mg/mL, about 69 mg/mL, about 70 mg/mL, about 71 mg/mL about 72 mg/mL, about 73 mg/mL, about 74 mg/mL, about 75 mg/mL, about 76 mg/mL, about 77 mg/mL, about 78 mg/mL, about 79 mg/mL, about 80 mg/mL, about 81 mg/mL about 82 mg/mL, about 83 mg/mL, about 84 mg/mL, about 85 mg/mL, about 86 mg/mL, about 87 mg/mL, about 88 mg/mL, about 89 mg/mL, about 90 mg/mL, about 91 mg/mL about 92 mg/mL, about 93 mg/mL, about 94 mg/mL, about 95 mg/mL, about 96 mg/mL, about 97 mg/mL, about 98 mg/mL, about 99 mg/mL, or about 100 mg/mL.

A formulation that is disclosed herein can be made more soluble by the addition of an additive or agent. The improvement of solubility of the formulation can increase by about 5%, about 10%, about 15%, about 20%, about 25%, about 30%, about 35%, 0%, a 40%, about 45%, about 50%, about 55%, about 60%, about 65%, about 70%, about 75% about 80%, about 85%, about 90%, about 95%, about 100%, about 110%, about 120%, about 130%, about 140%, about 150%, about 160%, about 170%, about 180%, about 190%, about 200%, about 225%, about 250%, about 275%, about 300%, about 325%, about 350%, about 375%, about 400%, about 450%, or about 500%.

A formulation disclosed herein can be stable for about 1 day, about 2 days, about 3 days, about 4 days, about 5 days, about 6 days, about 7 days, about 8 days, about 9 days, about 10 days, about 2 weeks, about 4 weeks, about 6 weeks, about 8 weeks, about 10 weeks, about 12 weeks, about 3 months, about 4 months, about 5 months, about 6 months, about 7 months, about 8 months, about 9 months, about 10 months, about 11 months, or about one year. A formulation disclosed herein can be stable, for example, at about 0° C., about 5° C., about 10° C., about 15° C., about 20° C., about 25° C., about 30° C., about 35° C., about 40° C., about 45° C., about 50° C., about 60° C., about 70° C., or about 80° C.

Excipients.

A pharmaceutical composition of the invention can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, rectal, aerosol, parenteral, ophthalmic, pulmonary, transdermal, vaginal, otic, nasal, and topical administration.

A pharmaceutical composition can be administered in a local or systemic manner, for example, via injection of the compound directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated readily by combining the active compounds with pharmaceutically-acceptable carriers or excipients. Such carriers can be used to formulate tablets, powders, pills, dragees, capsules, liquids, gels, syrups, elixirs, slurries, suspensions and the like, for oral ingestion by a subject.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Cores can be provided with suitable coatings. For this purpose, concentrated sugar solutions can be used, which can contain an excipient such as gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings, for example, for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. A gelatin can be alkaline-processed. The push-fit capsules can contain the active ingredients in admixture with filler such as lactose, binders such as starches, and/or lubricants such as talc or magnesium stearate and, stabilizers. In soft capsules, the active compounds can be dissolved or suspended in suitable liquids, such as fatty oils, liquid paraffin, or liquid polyethylene glycols. Stabilizers can be added. All formulations for oral administration are provided in dosages suitable for such administration.

For buccal or sublingual administration, the compositions can be tablets, lozenges, or gels.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

Formulations suitable for transdermal administration of the active compounds can employ transdermal delivery devices and transdermal delivery patches, and can be lipophilic emulsions or buffered aqueous solutions, dissolved and/or dispersed in a polymer or an adhesive. Such patches can be constructed for continuous, pulsatile, or on demand delivery of pharmaceutical compounds. Transdermal delivery can be accomplished by means of iontophoretic patches. Additionally, transdermal patches can provide controlled delivery. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices can be in the form of a bandage comprising a backing member, a reservoir containing compounds and carriers, a rate controlling barrier to deliver the compounds to the skin of the subject at a controlled and predetermined rate over a prolonged period of time, and adhesives to secure the device to the skin or the eye.

For administration by inhalation, the active compounds can be in a form as an aerosol, a mist, or a powder. Pharmaceutical compositions are conveniently delivered in the form of an aerosol spray presentation from pressurized packs or a nebuliser, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone and PEG. In suppository forms of the compositions, a low-melting wax such as a mixture of fatty acid glycerides or cocoa butter can be used.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compounds described herein can be manufactured, for example, by mixing, dissolving, granulating, dragee-making, levigating, emulsifying, encapsulating, entrapping, or compression processes.

The pharmaceutical compositions can include at least one pharmaceutically acceptable carrier, diluent, or excipient and compounds described herein as free-base or pharmaceutically-acceptable salt form. The methods and pharmaceutical compositions described herein include the use crystalline forms (also known as polymorphs), and active metabolites of these compounds having the same type of activity.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, cachets, and suppositories. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals, and any combination thereof.

Non-limiting examples of pharmaceutically-acceptable excipients suitable for use in the invention include granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, anti-microbial agents, plant cellulosic material and spheronization agents, and any combination thereof.

A composition of the invention can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that drug release rates and drug release profiles can be matched to physiological and chronotherapeutic requirements or, alternatively, has been formulated to effect release of a drug at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

The disclosed compositions can optionally comprise from about 0.001% to about 0.005% weight by volume pharmaceutically acceptable preservatives. One non-limiting example of a suitable preservative is benzyl alcohol.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), each of which is incorporated by reference in its entirety.

The disclosed methods include administration of a HPTP-β inhibitor, or a pharmaceutically acceptable salt thereof, in combination with a pharmaceutically acceptable carrier. The carrier can be selected to minimize any degradation of the active ingredient and to minimize any adverse side effects in the subject.

In another aspect, the HPTP-β inhibitor or a pharmaceutically acceptable salt thereof can be used prophylactically, i.e., as a preventative agent after treatment with an anti-VEGF agent has stopped. The HPTP-β inhibitor or a pharmaceutically acceptable salt thereof herein can be conveniently formulated into pharmaceutical compositions composed of one or more pharmaceutically acceptable carriers. See e.g., *Remington's Pharmaceutical Sciences*, latest edition, by E. W. Martin Mack Pub. Co., Easton, Pa., which discloses typical carriers and conventional methods of preparing pharmaceutical compositions that can be used in conjunction with the preparation of formulations of the compound described herein and which is incorporated by reference herein. Such pharmaceuticals can be standard carriers for administration of compositions to humans and non-humans, including solutions such as sterile water, saline, and buffered solutions at physiological pH. Other compositions can be administered according to standard procedures. For example, pharmaceutical compositions can also include one or more additional active ingredients such as antimicrobial agents, anti-inflammatory agents, and anesthetics.

Non-limiting examples of pharmaceutically-acceptable carriers include, but are not limited to, saline, Ringer's solution and dextrose solution. The pH of the solution can be from about 5 to about 8, and can be from about 7 to about 7.5. Further carriers include sustained release preparations such as semipermeable matrices of solid hydrophobic polymers containing the HPTP-β inhibitor or a pharmaceutically-acceptable salt thereof, where the matrices are in the form of shaped articles, e.g., films, liposomes, microparticles, or microcapsules.

The disclosed methods relate to administering the HPTP-β inhibitor or a pharmaceutically acceptable salt thereof as part of a pharmaceutical composition. In various embodiments, compositions of the invention can comprise a liquid comprising an active agent in solution, in suspension, or both. Liquid compositions can include gels. In one embodiment, the liquid composition is aqueous. Alternatively, the composition can take form of an ointment. In another embodiment, the composition is an in situ gellable aqueous composition. In some embodiments, the composition is an in situ gellable aqueous solution. Such a composition can comprise a gelling agent in a concentration effective to promote gelling upon contact with the eye or lacrimal fluid in the exterior of the eye. Aqueous compositions of the invention have ophthalmically compatible pH and osmolality. The composition can comprise an ophthalmic depot formulation comprising an active agent for sub-conjunctival administration. The microparticles comprising the active agent can be embedded in a biocompatible pharmaceutically acceptable polymer or a lipid encapsulating agent. The depot formulations may be adapted to release all or substantially all the active material over an extended period of time. The polymer or lipid matrix, if present, may be adapted to degrade sufficiently to be transported from the site of administration after release of all or substantially all of the active agent. The depot formulation can be a liquid formulation, comprising a pharmaceutically-acceptable polymer and a dissolved or dispersed active agent. Upon injection, the polymer forms a depot at the injections site, e.g. by gelifying or precipitating. The composition can comprise a solid article that can be inserted in a suitable location in the eye, such as between the eye and eyelid or in the conjuctival sac, where the article releases the active agent. Solid articles suitable for implantation in the eye can comprise polymers and can be bioerodible or non-bioerodible.

Pharmaceutical formulations can include additional carriers, as well as thickeners, diluents, buffers, preservatives, and surface active agents in addition to the compounds disclosed herein. Pharmaceutical formulations can also include one or more additional active ingredients such as antimicrobial agents, anti-inflammatory agents, anesthetics, and the like.

An excipient can fill a role as simple and direct as being an inert filler, or an excipient as used herein may be part of a pH stabilizing system or coating to insure delivery of the ingredients safely to the stomach.

The HPTP-β inhibitor or a pharmaceutically-acceptable salt thereof can also be present in liquids, emulsions, or suspensions for delivery of active therapeutic agents in aerosol form to cavities of the body such as the nose, throat, or bronchial passages. The ratio of HPTP-β inhibitor or a pharmaceutically-acceptable salt thereof to the other compounding agents in these preparations can vary as the dosage form requires.

Depending on the intended mode of administration, the pharmaceutical compositions administered as part of the disclosed methods can be in the form of solid, semi-solid or liquid dosage forms, such as, for example, tablets, suppositories, pills, capsules, powders, liquids, suspensions, lotions, creams, gels, or the like, for example, in unit dosage form suitable for single administration of a precise dosage. The compositions can contain, as noted above, an effective amount of the HPTP-β inhibitor or a pharmaceutically-acceptable salt thereof in combination with a pharmaceutically-acceptable carrier and, in addition, can include other medicinal agents, pharmaceutical agents, carriers, adjuvants, diluents, etc.

For solid compositions, nontoxic solid carriers include, for example, pharmaceutical grades of mannitol, lactose, starch, magnesium stearate, sodium saccharin, talc, cellulose, glucose, sucrose, and magnesium carbonate. In one embodiment, a composition comprising the HPTP-β inhibitor or a pharmaceutically acceptable salt thereof in an amount of approximately 5 mg per 0.1 mL liquid is prepared. The liquid phase comprises sterile water and an appropriate amount of a saccharide or polysaccharide.

Methods of Administration and Treatment Methods.

Pharmaceutical compositions containing the compounds described herein can be administered for prophylactic and/or therapeutic treatments. In therapeutic applications, the compositions can be administered to a subject already suffering from a disease or condition, in an amount sufficient to cure or at least partially arrest the symptoms of the disease or condition, or to cure, heal, improve, or ameliorate the condition. Compounds can also be administered to lessen a likelihood of developing, contracting, or worsening a condition. Amounts effective for this use can vary based on the severity and course of the disease or condition, previous therapy, the subject's health status, weight, response to the drugs, and the judgment of the treating physician.

Multiple therapeutic agents can be administered in any order or simultaneously. If simultaneously, the multiple therapeutic agents can be provided in a single, unified form, or in multiple forms, for example, as multiple separate pills. The compounds can be packed together or separately, in a single package or in a plurality of packages. One or all of the therapeutic agents can be given in multiple doses. If not simultaneous, the timing between the multiple doses may vary.

Compounds and compositions of the invention can be packaged as a kit. In some embodiments, the invention provides a kit comprising a compound disclosed herein, or a pharmaceutically-acceptable salt thereof, and written instructions on use of the kit in the treatment of a condition described herein. In some embodiments, the invention provides a kit comprising a compound disclosed herein, or a pharmaceutically-acceptable salt thereof, an antibody, and written instructions on use of the kit in the treatment of a condition described herein.

The compounds described herein can be administered before, during, or after the occurrence of a disease or condition, and the timing of administering the composition containing a compound can vary. For example, the compounds can be used as a prophylactic and can be administered continuously to subjects with a propensity to conditions or diseases in order to lessen a likelihood of the occurrence of the disease or condition. The compounds and compositions can be administered to a subject during or as soon as possible after the onset of the symptoms. The administration of the compounds can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein. A compound can be administered as soon as is practical after the onset of a disease or condition is detected or suspected, and for a length of time necessary for the treatment of the disease, such as, for example, from about 1 month to about 3 months. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for parenteral injection can be presented in unit dosage form, for example, in ampoules, or in multi-dose containers with a preservative.

A compound described herein can be present in a composition in a range of from about 1 mg to about 2000 mg; from about 5 mg to about 1000 mg, from about 10 mg to about 25 mg to 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

Methods.

Disclosed herein are methods for the treatment of diseases or conditions of the eye, for example, diabetic macular edema, age-related macular degeneration (including wet form), choroidal neovascularization, diabetic retinopathy, ocular ischemia, uveitis, retinal vein occlusion (central or branch), ocular trauma, surgery induced edema, surgery induced neovascularization, cystoid macular edema, ocular ischemia, changes in central foveal thickness, and uveitis. These diseases or conditions can be characterized by changes in the ocular vasculature whether progressive or non-progressive, whether a result of an acute disease or condition, or a chronic disease or condition. In some embodiments, these diseases can be characterized by an increased level of plasma Vascular Endothelial Growth Factor (VEGF).

In some embodiments, the disclosed methods relate to the administration of the HPTP-β inhibitor or a pharmaceutically acceptable salt thereof, as well as compositions comprising the HPTP-β inhibitor or a pharmaceutically-acceptable salt thereof.

In some embodiments, the methods of the disclosure are drawn towards co-administration of a HPTP-β inhibitor or a pharmaceutically-acceptable salt thereof which stabilizes the vasculature against leakage, and one or more anti-VEGF agents.

In some embodiments, the methods of the disclosure are drawn towards co-administration of a HPTP-β inhibitor or a pharmaceutically-acceptable salt thereof which stabilizes the vasculature against neovascularization, and one or more anti-VEGF agents.

In some embodiments, the inhibitor stabilizes the vasculature against leakage and neovascularization.

In some embodiments, a human subject with at least one visually impaired eye is treated with an HPTP-β inhibitor or a pharmaceutically acceptable salt thereof via subcutaneous or intravitreal injection. Improvement of clinical symptoms can be monitored via, for example, indirect ophthalmoscopy, fundus photography, fluorescein angiopathy, electroretinography, external eye examination, slit lamp biomicroscopy, applanation tonometry, pachymetry, optical coherence tomography and autorefaction. As described herein, the dosing can occur at any frequency determined by the administrator. After cessation of the anti-VEGF agent treatment, subsequent doses can be administered weekly or monthly, e.g., with a frequency of 2-8 weeks or 1-12 months apart depending upon the response.

One aspect of the disclosed methods relates to diseases that are a direct or indirect result of diabetes, inter alia, diabetic macular edema and diabetic retinopathy. The ocular vasculature of the diabetic becomes unstable over time leading to conditions such as non-proliferative retinopathy, macular edema, and proliferative retinopathy. As fluid leaks into the center of the macula, the part of the eye where sharp, straight-ahead vision occurs, the buildup of fluid and the associated protein begin to deposit on or under the macula. This results in swelling that causes the subject's central vision to become distorted. This condition is referred to as "macular edema." Another condition that can occur is non-proliferative retinopathy in which vascular changes, such as microaneurysms, outside the macular region of the eye can be observed.

These conditions can progress to diabetic proliferative retinopathy, which is characterized by increased neovascularization. These new blood vessels are fragile and are susceptible to bleeding. The result is scarring of the retina, as well as occlusion or total blockage of the light pathway through the eye due to the over formation of new blood vessels. Diabetic macular edema can begin during either the proliferative or non-proliferative stage of diabetic retinopathy.

Diabetic retinopathy is a common cause of vision loss in working-aged Americans. Severe vision loss can occur due to tractional retinal detachments that complicate retinal neovascularization (NV), and moderate vision loss can be caused by diabetic macular edema (DME). The pathogenesis of DME can involve hypoxia. VEGF is a hypoxia-regulated gene, and VEGF levels are increased in hypoxic or ischemic retina. Injection of VEGF into mouse eyes causes breakdown of the inner blood-retinal barrier and sustained release of VEGF in the eyes of monkeys causes macular edema.

The effects of VEGF on vascular endothelial cells are modulated by Tie2 receptors, which are selectively expressed on vascular endothelial cells and are required for embryonic vascular development. Angiopoietin 1 (Ang1) binds Tie2 with high affinity and initiates phosphorylation and downstream signaling. Angiopoietin 2 (Ang2) binds Tie2 with high affinity, but does not stimulate phosphorylation in cultured endothelial cells. Ang2 acts as a competitive inhibitor of Ang1 and transgenic mice overexpressing Ang2 have a phenotype similar to Ang1-deficient mice, and Ang2 is a developmentally- and hypoxia-regulated permissive factor for VEGF-induced neovascularization in the retina. Ang2 reduces stabilizing signals from the matrix making endothelial cells dependent upon VEGF and other soluble stimulators; when VEGF is high, neovascularization is stimulated and when VEGF is low, neovascularization regresses. In contrast, Ang1 increases stabilizing signals from the matrix and makes the vasculature unresponsive to soluble stimulators like VEGF.

Angiopoietin 2 binds Tie2, but does not stimulate phosphorylation and therefore acts as an antagonist under most circumstances. In the eye, Ang2 is upregulated at sites of neovascularization and acts as a permissive factor for VEGF. Increased expression of VEGF in the retina does not stimulate sprouting of neovascularization from the superficial or intermediate capillary beds of the retina or the choriocapillaris, but does stimulate sprouting from the deep capillary bed. Co-expression of VEGF and Ang2 at the surface of the retina causes sprouting of neovascularization from the superficial retinal capillaries.

Macular degeneration is a condition characterized by a gradual loss or impairment of eyesight due to cell and tissue degeneration of the yellow macular region in the center of the retina. Macular degeneration is often characterized as one of two types, non-exudative (dry form) or exudative (wet form). Although both types are bilateral and progressive, each type can reflect different pathological processes. The wet form of age-related macular degeneration (AMD) is the most common form of choroidal neovascularization and a leading cause of blindness in the elderly. AMD affects millions of Americans over the age of 60, and is a leading cause of new blindness among the elderly.

Choroidal neovascular membrane (CNVM) is a problem that is related to a wide variety of retinal diseases, and is commonly linked to AMD. With CNVM, abnormal blood vessels stemming from the choroid (the blood vessel-rich tissue layer just beneath the retina) grow up through the retinal layers. These new vessels are very fragile and break easily, causing blood and fluid to pool within the layers of the retina.

Diabetes (diabetes mellitus) is a metabolic disease caused by the inability of the pancreas to produce insulin or to use the insulin that is produced. The most common types of diabetes are type 1 diabetes (often referred to as Juvenile Onset Diabetes Mellitus) and type 2 diabetes (often referred to as Adult Onset Diabetes Mellitus). Type 1 diabetes results from the body's failure to produce insulin due to loss of insulin producing cells, and presently requires the person to inject insulin. Type 2 diabetes generally results from insulin resistance, a condition in which cells fail to use insulin properly.

Diabetes can be correlated to a large number of other conditions, including conditions or diseases of the eye including diabetic retinopathy (DR) and diabetic macular edema (DME), which are leading causes of vision loss and blindness in most developed countries. The increasing number of individuals with diabetes worldwide suggests that DR and DME continue to be major contributors to vision loss and associated functional impairment for years to come.

DR is a complication of diabetes that results from damage to the blood vessels of the light-sensitive tissue at the back of the eye (retina). In early stages, DR frequently causes no symptoms or only mild vision problems. Eventually, DR can result in blindness. DR can develop in anyone who has type 1 diabetes or type 2 diabetes.

At its earliest stage, non-proliferative retinopathy, microaneurysms occur in the retina's tiny blood vessels. As the disease progresses, more of these blood vessels become damaged or blocked and these areas of the retina send signals into the regional tissue to grow new blood vessels for nourishment. This stage is called proliferative retinopathy. The new blood vessels grow along the retina and along the surface of the clear, vitreous gel that fills the inside of the eye. By themselves, these blood vessels do not cause symptoms or vision loss. However, without timely treatment, these new blood vessels can leak blood (whole blood or some constituents thereof), resulting in severe vision loss and even blindness. Also, fluid can leak into the center of the macula, the part of the eye where sharp, straight-ahead vision occurs. The fluid and the associated proteins begin to deposit on or under the macula, which causesthe patient's central vision to become distorted. This condition is called macular edema, and can occur at any stage of diabetic retinopathy, but is more likely to occur as the disease progresses. About half of the people with proliferative retinopathy also have macular edema.

Uveitis is a condition in which the uvea becomes inflamed. The eye is shaped much like a tennis ball, hollow on the inside with three different layers of tissue surrounding a central cavity. The outermost is the sclera (white coat of the eye) and the innermost is the retina. The middle layer between the sclera and the retina is called the uvea. The uvea contains many of the blood vessels that nourish the eye. Complications of uveitis include glaucoma, cataracts or new blood vessel formation (neovascularization).

Ocular trauma is any sort of physical or chemical injury to the eye. Symptoms include redness or pain in the affected eye.

Surgery-induced edema is the development of swelling in the eye tissues following surgery on the retina or other part of the eye. Cystoid macular edema (CME) is an example of this phenomenon. CME can occur not only in people who have had cataract surgery, but also those with diabetes, retinitis pigmentosa, AMD, or conditions that cause chronic inflammation in the eye. Symptoms of CME include blurred or decreased central vision.

Ocular ischemic syndrome (OIS) encompasses the signs and symptoms that result from chronic vascular insufficiency. This condition is caused by ocular hypoperfusion due to occlusion or stenosis of the common or internal carotid arteries. OIS generally affects those between the ages of 50-80, who can also have systemic diseases such as hypertension or diabetes. Symptoms of OIS include orbital pain, vision loss, changes of the visual field, asymmetric cataract, and sluggish reaction to light.

Retinal vein occlusion (RVO) is the most common retinal vascular disease after diabetic retinopathy. Depending on the area of retinal venous drainage effectively occluded, the condition can be classified as central retinal vein occlusion (CRVO), hemispheric retinal vein occlusion (HRVO), or branch retinal vein occlusion (BRVO). Each type has two subtypes. Presentation of RVO is with variable painless visual loss with any combination of fundal findings consisting of retinal vascular tortuosity, retinal hemorrhages (blot and flame shaped), cotton wool spots, optic disc swelling, and macular edema. In a CRVO, retinal hemorrhages can be found in all four quadrants of the fundus, whereas these are restricted to either the superior or inferior fundal hemisphere in a HRVO. In a BRVO, hemorrhages are largely localized to the area drained by the occluded branch retinal vein. Vision loss occurs secondary to macular edema or ischemia.

Angiogenesis, the process of creating new blood vessels from pre-existing vessels, is essential to a wide range of physiological and pathological events including embryological development, menstruation, wound healing, and tumor growth. Most tumors require angiogenesis to grow and proliferate. VEGF is a major factor in angiogenesis, which can increase vessel permeability and capillary number.

Vascular endothelial growth factor (VEGF) is a protein that is primarily found in endothelial cells and has functions in vasculogenesis, angiogenesis, and permeabilization of blood vessels. The expression of VEGF is induced by hypoxia, activated oncogenes, and cytokines. VEGF activation not only leads to angiogenesis in normal human cells and tissues, but also angiogenesis in tumors, allowing for tumor progression and growth. Inhibition of VEGF inhibits tumor growth leading to tumor regression.

A variety of retinopathies are associated with increased levels of VEGF. Ischemia in the eye leads to an induction of VEGF production due to lack of oxygen. This increase in VEGF can cause hyperproliferation of blood vessels in the retina, eventually leading to blindness. The disclosed HPTP-β inhibitors act to stabilize ocular vasculature and, in some embodiments, a compound of the invention can counteract the stimulation caused by VEGF and other inflammatory agents that can be present in the diseased retina.

The compounds can be administered in any order convenient to the user or to the subject receiving treatment. In one non-limiting example of the disclosed methods, a compound herein or a pharmaceutically acceptable salt thereof is administered first followed by administration of ranibizumab. In another embodiment ranibizumab is administered first followed by administration of the compound herein or a pharmaceutically acceptable salt thereof. The time period between dosing or administration of the first component of treatment can be any time period convenient to the formulator or subject receiving treatment. For example, the compound herein or a pharmaceutically acceptable salt thereof can be administered minutes, hours, days or weeks prior to the administration of ranibizumab or more than one dosage of the compound herein or a pharmaceutically acceptable salt thereof can be given to establish a therapeutic amount in the subject being treated.

In a further embodiment, the compound herein or a pharmaceutically-acceptable salt thereof are administered daily in one or more doses and the ramibizumab is administered according to a separate schedule. For example, in addition to daily dosing of the compound herein, ranibizumab can be administered once a month, once every 2 months, once every 3 months, once every 4 months, once every 6 months, etc.

The dosage for an antibody described herein can be in any amount necessary. In one embodiment, the antibody is administered in an amount from about 0.05 mg to about 1.5 mg, from about 0.1 mg to about 1.5 mg, from about 0.1 to about 5 mg, from about 0.1 mg to about 3 mg, from about 0.5 mg to about 3 mg, or from about 0.5 mg to about 2 mg. In one non-limiting example, the antibody is administered in an amount of 1.2 mg. The amount of an antibodyadministered per treatment can be in any amount, for example, about 0.05 mg, about 0.06 mg, about 0.07 mg, about 0.08 mg, about 0.09 mg, about 0.1 mg, about 0.11 mg, about 0.12 mg, about 0.13 mg, about 0.14 mg, about 0.15 mg, about 0.16 mg, about 0.17, mg, about 0.18 mg, about 0.19 mg, about 0.2 mg, about 0.21 mg, about 0.22 mg, about 0.23 mg, about 0.24 mg, about 0.25 mg, about 0.26 mg, about 0.27, mg, about 0.28 mg, about 0.29 mg, about 0.3 mg, about 0.31 mg, about 0.32 mg, about 0.33 mg, about 0.34 mg, about 0.35 mg, about 0.36 mg, about 0.37, mg, about 0.38 mg, about 0.39 mg, about 0.4 mg, about 0.41 mg, about 0.42 mg, about 0.43 mg, about 0.44 mg, about 0.45 mg, about 0.46 mg, about 0.47, mg, about 0.48 mg, about 0.49 mg, about 0.5 mg, about 0.51 mg, about 0.52 mg, about 0.53 mg, about 0.54 mg, about 0.55 mg, about 0.56 mg, about 0.57, mg, about 0.58 mg, about 0.59 mg, about 0.6 mg, about 0.61 mg, about 0.62 mg, about 0.63 mg, about 0.64 mg, about 0.65 mg, about 0.66 mg, about 0.67, mg, about 0.68 mg, about 0.69 mg, about 0.7 mg, about 0.71 mg, about 0.72 mg, about 0.73 mg, about 0.74 mg, about 0.75 mg, about 0.76 mg, about 0.77, mg, about 0.78 mg, about 0.79 mg, about 0.8 mg, about 0.81 mg, about 0.82 mg, about 0.83 mg, about 0.84 mg, about 0.85 mg, about 0.86 mg, about 0.87, mg, about 0.88 mg, about 0.89 mg, about 0.9 mg, about 0.91 mg, about 0.92 mg, about 0.93 mg, about 0.94 mg, about 0.95 mg, about 0.96 mg, about 0.97, mg, about 0.98 mg, about 0.99 mg, about 1 mg, about 1.01 mg, about 1.02 mg, about 1.03 mg, about 1.04 mg, about 1.05 mg, about 1.06 mg, about 1.07, mg, about 1.08 mg, about 1.09 mg, 1.1 mg, about 1.11 mg, about 1.12 mg, about 1.13 mg, about 1.14 mg, about 1.15 mg, about 1.16 mg, about 1.17, mg, about 1.18 mg, about 1.19 mg, about 1.2 mg, about 1.21 mg, about 1.22 mg, about 1.23 mg, about 1.24 mg, about 1.25 mg, about 1.26 mg, about 1.27, mg, about 1.28 mg, about 1.29 mg, about 1.3 mg, about 1.31 mg, about 1.32 mg, about 1.33 mg, about 1.34 mg, about 1.35 mg, about 1.36 mg, about 1.37, mg, about 1.38 mg, about 1.39 mg, about 1.4 mg, about 1.41 mg, about 1.42 mg, about 1.43 mg, about 1.44 mg, about 1.45 mg, about 1.46 mg, about 1.47, mg, about 1.48 mg, about 1.49 mg, about 1.5 mg, about 1.51 mg, about 1.52 mg, about 1.53 mg, about 1.54 mg, about 1.55 mg, about 1.56 mg, about 1.57, mg, about 1.58 mg, about 1.59 mg, about 1.6 mg, about 1.61 mg, about 1.62 mg, about 1.63 mg, about 1.64 mg, about 1.65 mg, about 1.66 mg, about 1.67, mg, about 1.68 mg, about 1.69 mg, about 1.7 mg, about 1.71 mg, about 1.72 mg, about 1.73 mg, about 1.74 mg, about 1.75 mg, about 1.76 mg, about 1.77, mg, about 1.78 mg, about 1.79 mg, about 1.8 mg, about 1.81 mg, about 1.82 mg, about 1.83 mg, about 1.84 mg, about 1.85 mg, about 1.86 mg, about 1.87, mg, about 1.88 mg, about 1.89 mg, about 1.9 mg, about 1.91 mg, about 1.92 mg, about 1.93 mg, about 1.94 mg, about 1.95 mg, about 1.96 mg, about 1.97, mg, about 1.98 mg, about 1.99 mg, about 2 mg, about 2.5 mg, about 3 mg, about 3.5 mg, about 4 mg, about 4.5 mg, about 5 mg, about 6 mg, about 7 mg, about 8 mg, about 9 mg, or about 10 mg.

If the antibody is not administered simultaneously with the other compound herein, then the time between administration of the compound and the antibody can range, for example, from about 1 minute, about 2 minutes, about 3 minutes, about 4 minutes, about 5 minutes, about 10 minutes, about 15 minutes, about 20 minutes, about 25 minutes, about 30 minutes, about 40 minutes, about 50 minutes, about 60 minutes, about 2 hours, about 3 hours, about 4 hours, about 5 hours, about 10 hours, about 20 hours, about 1 day, about 2 days, about 3 days, about 4 days, about 5 days, about 6 days, about 1 week, about 2 weeks, about 3 weeks, to about 4 weeks.

The HPTP-β inhibitors or a pharmaceutically-acceptable salt thereof can be administered at any interval desired. For example, the compound can be administered once a week, 2 times a week, 3 times a week, 4 times a week, 5 times a week, 6 times a week, 7 times a week, 8 times a week, 9 times a week, or 10 times a week. The interval between daily dosing can be any hourly interval, for example, every hour, every 2 hours, every 3 hours, every 4 hours, every 5 hours, every 6 hours, every 7 hours, every 8 hours, every 9 hours, every 10 hours, every 11 hours, or every 12 hours.

Further non-limiting examples of anti-VEGF agents include dexamethasone, fluocinolone and triamcinolone. The disclosed methods can include implants that deliver an anti-VEGF agent. For example, HPTP-β inhibitors or a pharmaceutically-acceptable salt thereof can be co-administered before, during, or after an implant is provided to a subject suffering from a disease or condition described herein. For example, Ozurdex™ is an intraviteal implant that provides a supply of dexamethasone to a subject, Retisert™ and Iluvien™ are intravitreal implants that provide a supply of fluocinolone.

In some embodiments, a subject's Central Foveal Thickness is decreased from about 50 m to about 1000 m, from about 50 m to about 750 m, from about 200 m to about 1000 m, from about 150 m to about 500 m, from about 50 m to about 500 m, from about 250 m to about 650 m, from about 200 m to about 500 m, or from about 400 m to about 700 m. Visual acuity.

Further disclosed herein are methods for increasing the visual acuity of a subject having a disease or condition as disclosed herein. Visual acuity (VA) is acuteness or clearness of vision, which is dependent on the sharpness of the retinal focus within the eye and the sensitivity of the interpretative faculty of the brain. Visual acuity is a measure of the spatial resolution of the visual processing system. VA is tested by requiring the person whose vision is being tested to identify characters, typically numbers or letters, on a chart from a set distance. Chart characters are represented as black symbols against a white background. The distance between the person's eyes and the testing chart is set at a sufficient distance to approximate infinity in the way the lens attempts to focus. Twenty feet, or six meters, is essentially infinity from an optical perspective.

EXAMPLES

Example 1: Synthesis of an HPTP-Beta Inhibitor and its Diastereomers

Four compounds (A, B, C, and D) are shown below. Compound A is the S,R configuration; Compound B is the R,S configuration; Compound C is the R,R configuration; Compound D is the S, S configuration.

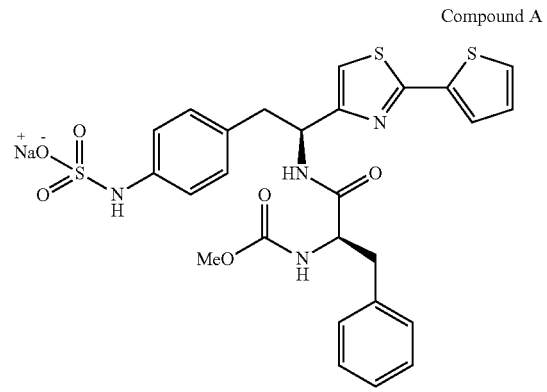

Compound C
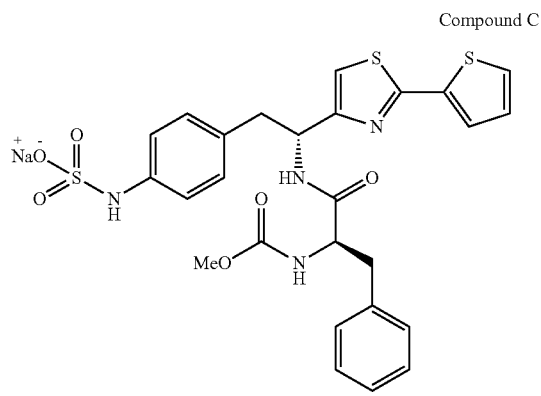
Compound D
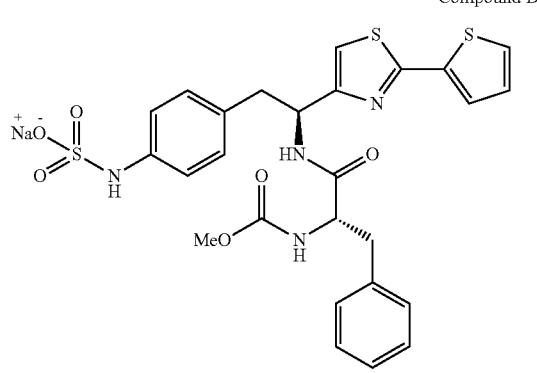
The generalized reaction scheme below was used to synthesize the compounds.
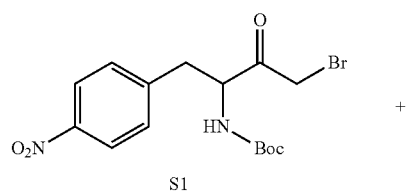
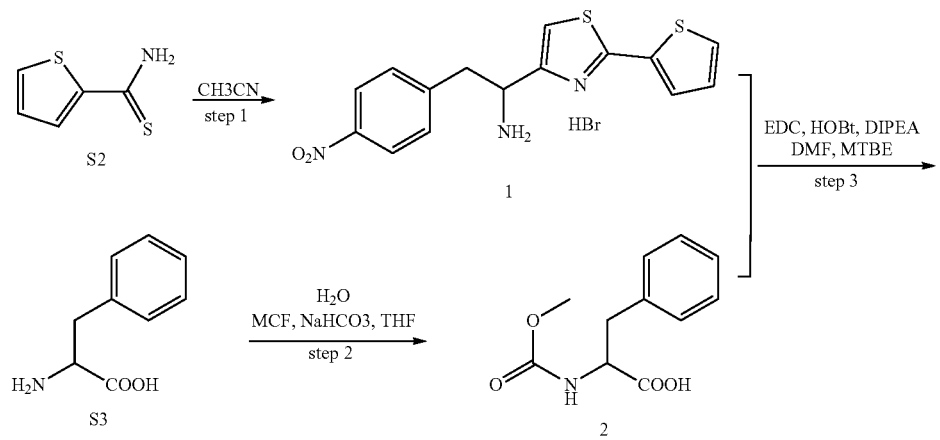
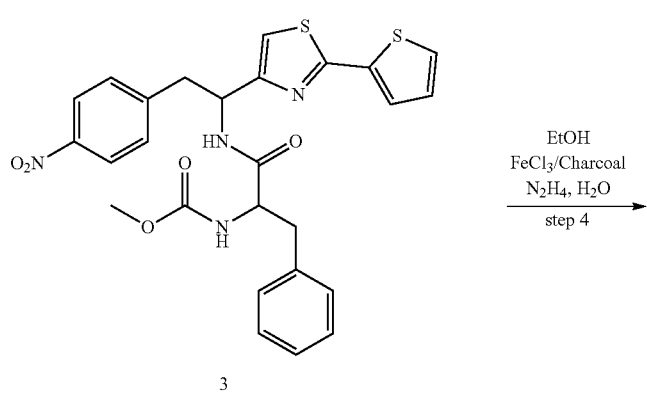

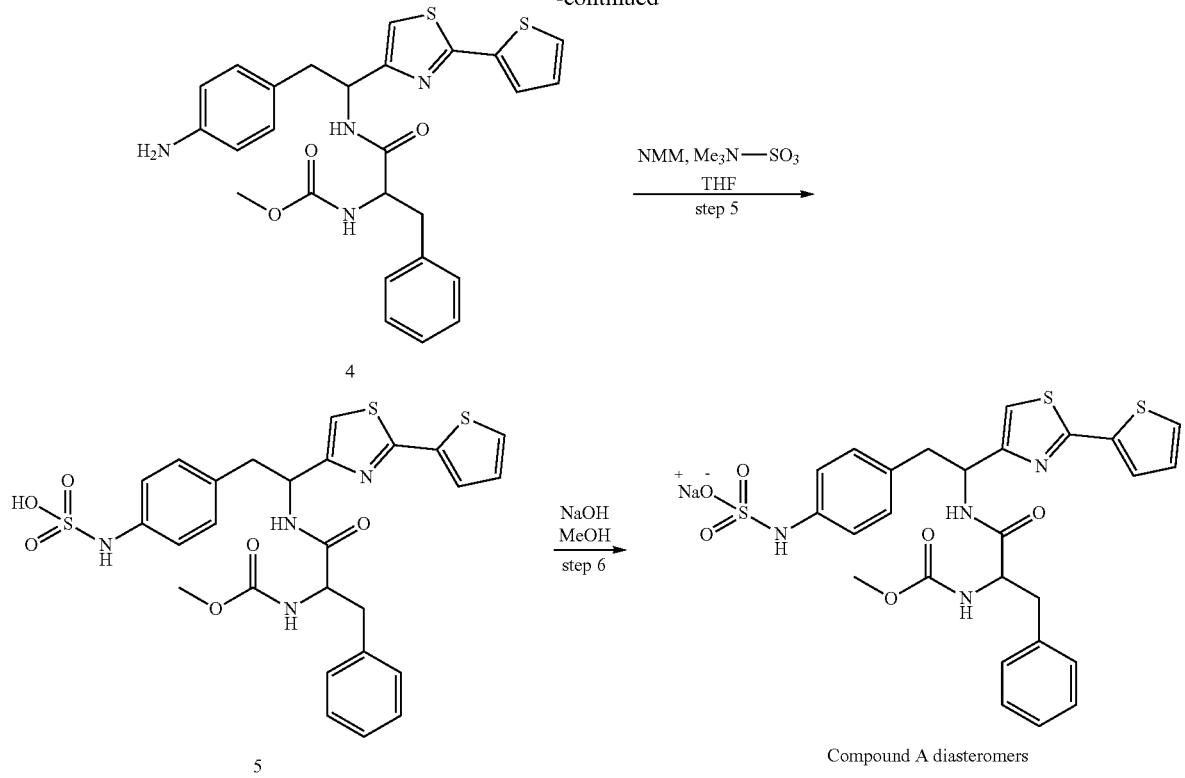

Compound A diasteromers

Synthesis of the starting material compound S for the synthesis of the compounds is detailed below:

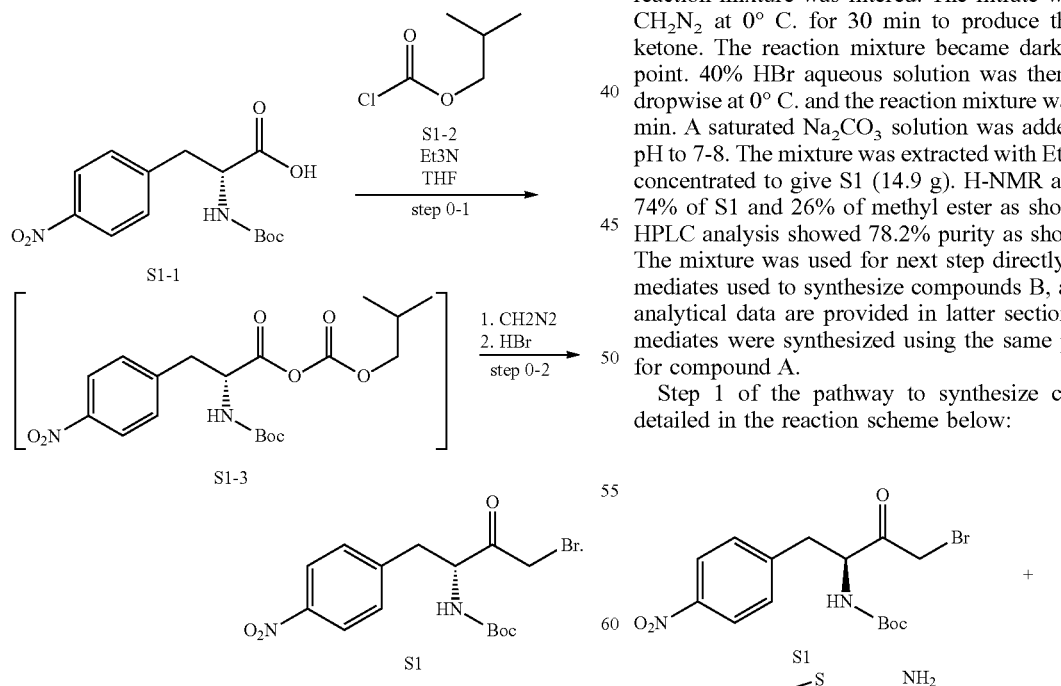

Figure 16:
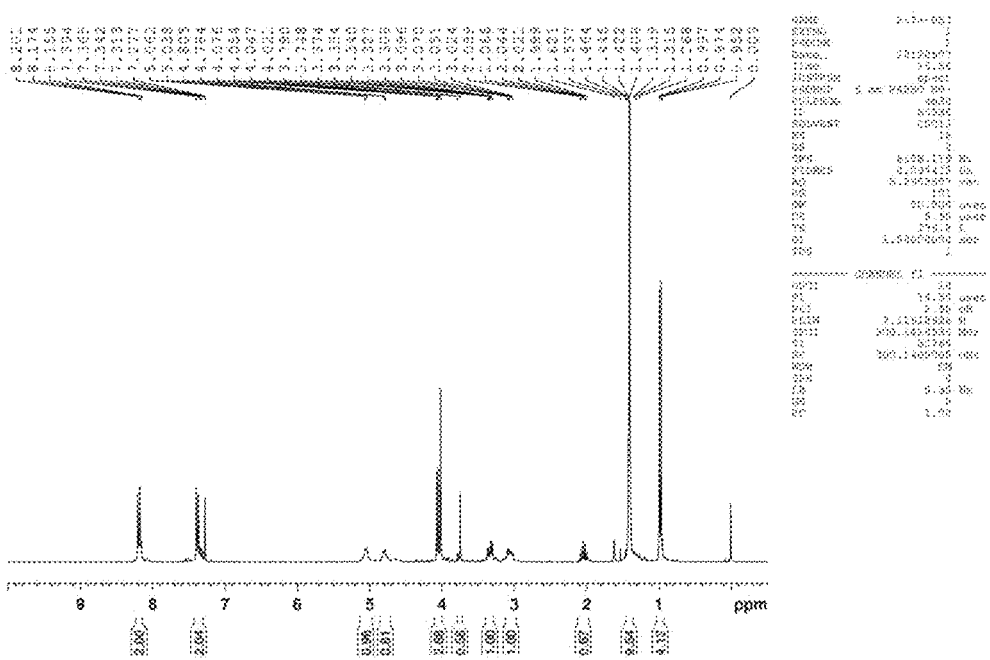
FIG. 16 displays the NMR data for the starting material for the synthesis of compound C.
Figure 17:
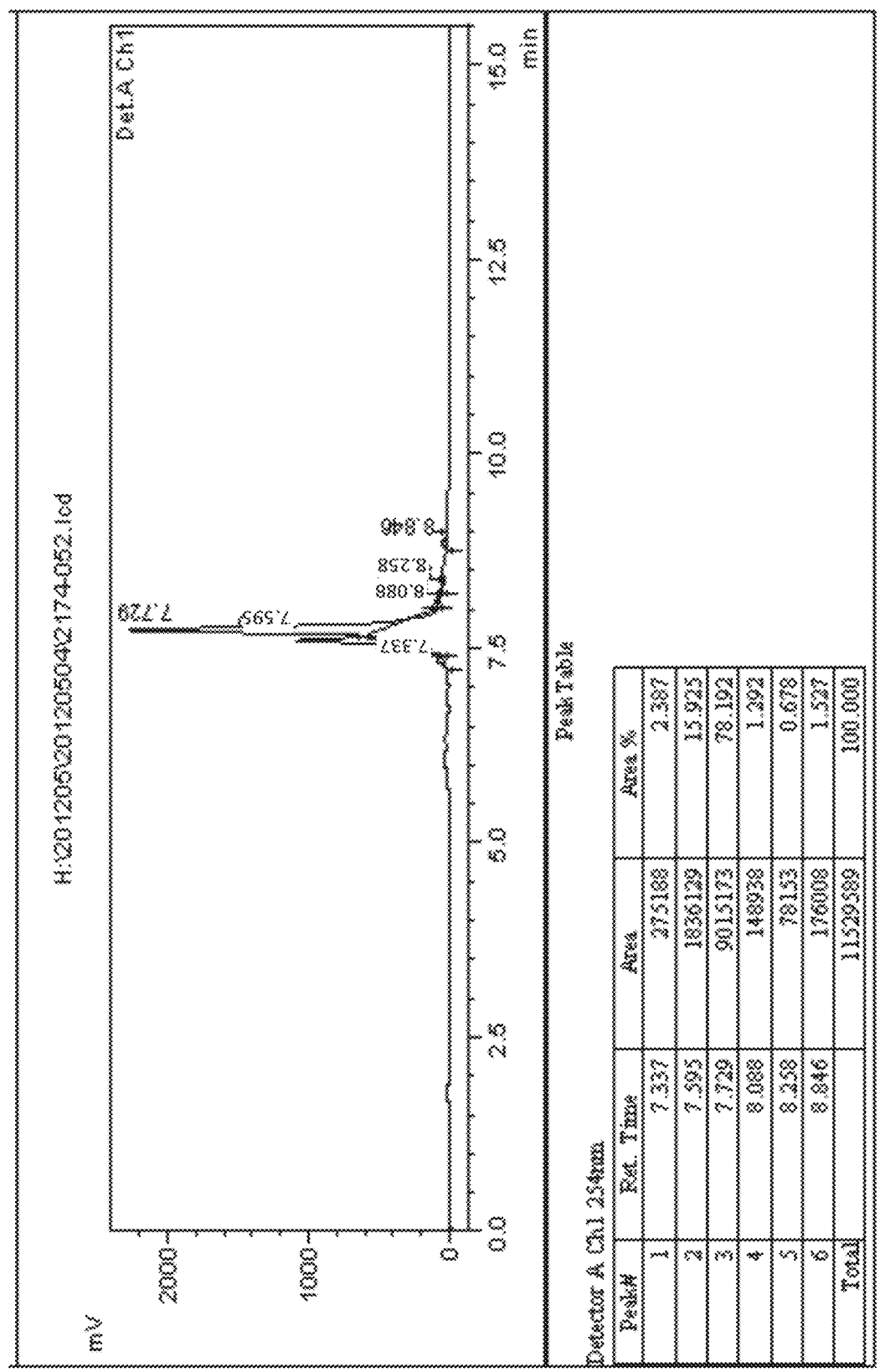
FIG. 17 displays the HPLC data for the starting material for the synthesis of compound C.

The R-isomer of compound S1 was prepared by adding compound S1-2 (5.7 mL, 44 mmol, 1.1 eq) dropwise at 0° C. to a solution of compound S1-1 (12 g, 38.7 mmol, 1.0 eq) and Et₃N (6.1 mL, d=0.75 g/mL, 44 mmol, 1.1 eq). After the addition, the mixture was stirred for another 1.5 h at 0° C. TLC analysis indicated that compound S1-1 was almost consumed. The reaction was stopped at that point and the reaction mixture was filtered. The filtrate was treated with CH₂N₂ at 0° C. for 30 min to produce the diazomethyl ketone. The reaction mixture became dark brown at that point. 40% HBr aqueous solution was then slowly added dropwise at 0° C. and the reaction mixture was stirred for 30 min. A saturated Na₂CO₃ solution was added to adjust the pH to 7-8. The mixture was extracted with EtOAc, dried and concentrated to give S1 (14.9 g). H-NMR analysis showed 74% of S1 and 26% of methyl ester as shown in FIG. 16. HPLC analysis showed 78.2% purity as shown in FIG. 17. The mixture was used for next step directly. For the intermediates used to synthesize compounds B, and C, only the analytical data are provided in latter sections as the intermediates were synthesized using the same procedure used for compound A.

Step 1 of the pathway to synthesize compound A is detailed in the reaction scheme below:

-continued

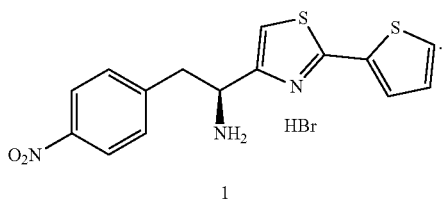

1

Synthesis of compound 1 was performed using a solution of compound S1 (10 g, 25.8 mmol 1.0 eq) and compound S2 (3.88 g, 27.0 mmol, 1.05 eq) in CH$_3$CN (200 mL) at reflux for 3 h. TLC analysis indicated that compound S1 was consumed. The reaction mixture was then cooled to room temperature. The solid was collected by filtration and dried under high vacuum. 10.2 g of 1 was obtained as a white solid. The yield was 96%.

Figure 1:
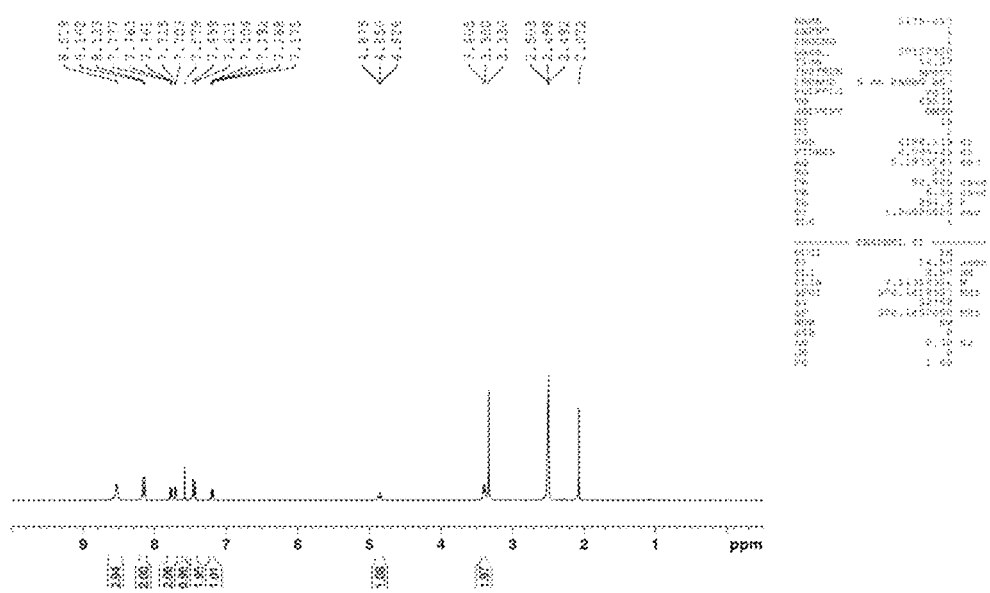
FIG. 1 displays the NMR data for the final product of step 1 of the synthesis of compound A.
Figure 2:
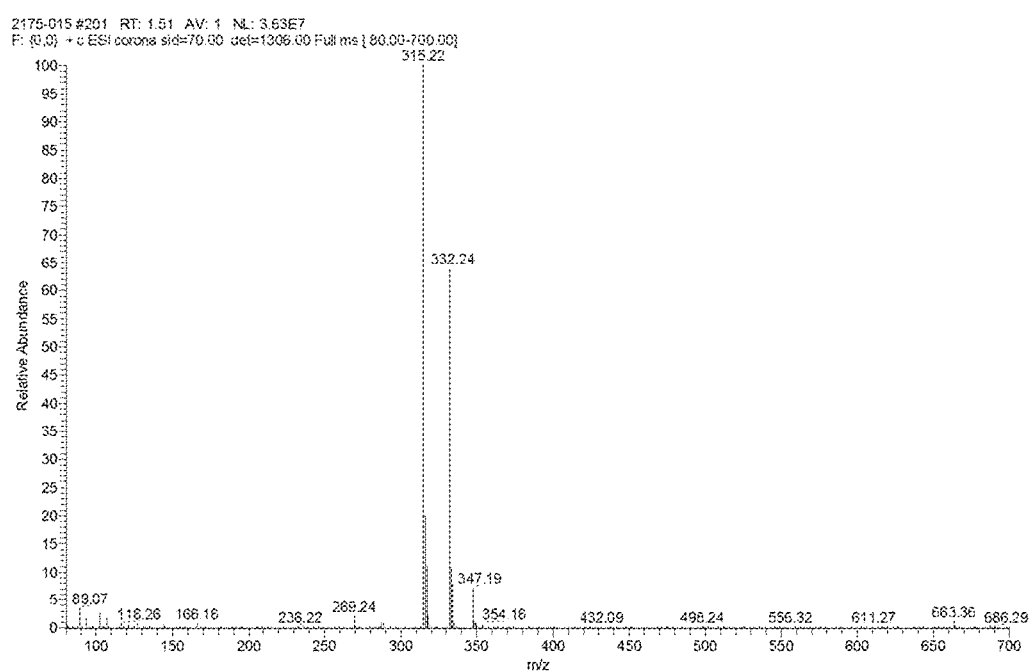
FIG. 2 displays the HPLC data for the final product of step 1 of the synthesis of compound A.
Figure 3:
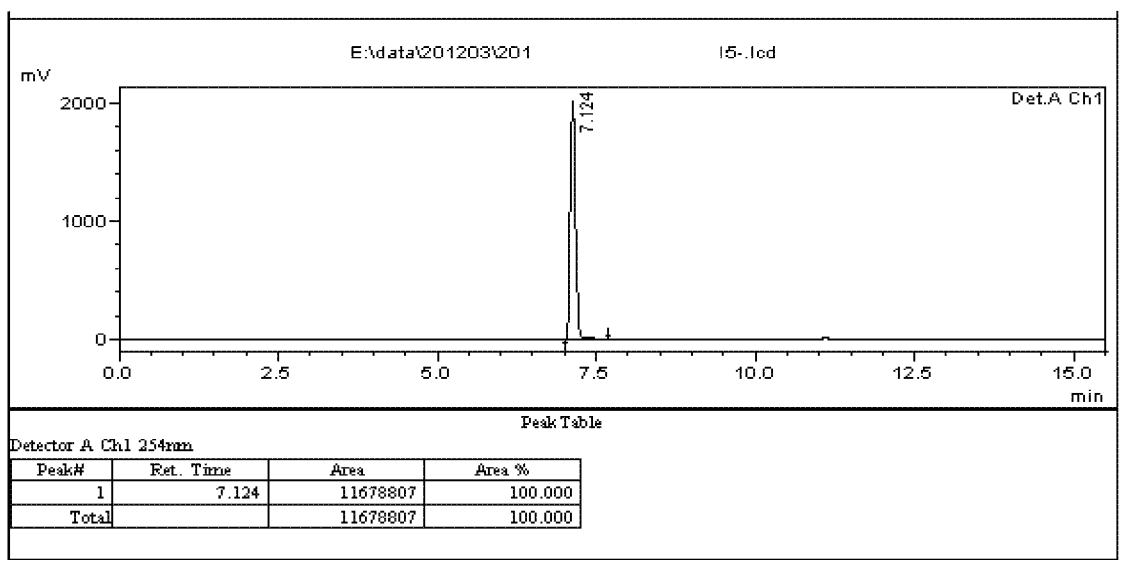
FIG. 3 displays the LCMS data for the final product of step 1 of the synthesis of compound A.

The analytical data for compound 1 were as follows: HPLC: ~100% (FIG. 2); LCMS (ESI+): m/z 332 (M+H) (FIG. 3); $^1$H-NMR (300 MHz, DMSO-d$_6$) δ 8.52 (br s, 3H), 8.15 (d, J=8.6 Hz, 2H), 7.77 (d, J=4.2 Hz, 1H), 7.70 (d, J=3.6 Hz, 1H), 7.57 (s, 1H), 7.18 (dd, J=4.2 Hz, J=3.6 Hz, 1H), 4.85 (t, J=7.4 Hz, 1H), 3.40 (d, J=7.4 Hz, 2H) (FIG. 1).

Step 2 of the scheme is detailed below.

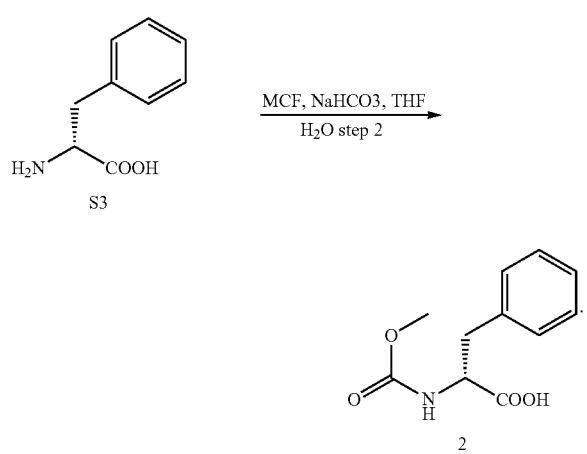

Synthesis of compound 2 was done by charging a 100 mL three-necked round-bottom flask with compound S3 (3 g, 18.2 mmol, 1.0 eq), THF (60 mL), water (60 mL) and NaHCO$_3$ (2.3 g, 27.4 mmol, 1.5 eq). The resulting slurry was cooled to 5° C. Methyl chloroformate (MCF) (2.0 g, 21.3 mmol, 1.2 eq) was added dropwise over 5 minutes and the resulting mixture was stirred at RT overnight. The pH of the reaction mixture was then adjusted to <2 by the addition of the concentrated HCl (~15 mL). The quenched reaction mixture was extracted with EtOAc (3×50 mL). The combined organic layer was washed with brine (3×100 mL), dried over MgSO$_4$, filtered and concentrated to give the crude product of compound 2 (4.3 g, yield >100%). Compound 2 was directly used for the next step without further purification.

Step 3 of the scheme is detailed below.

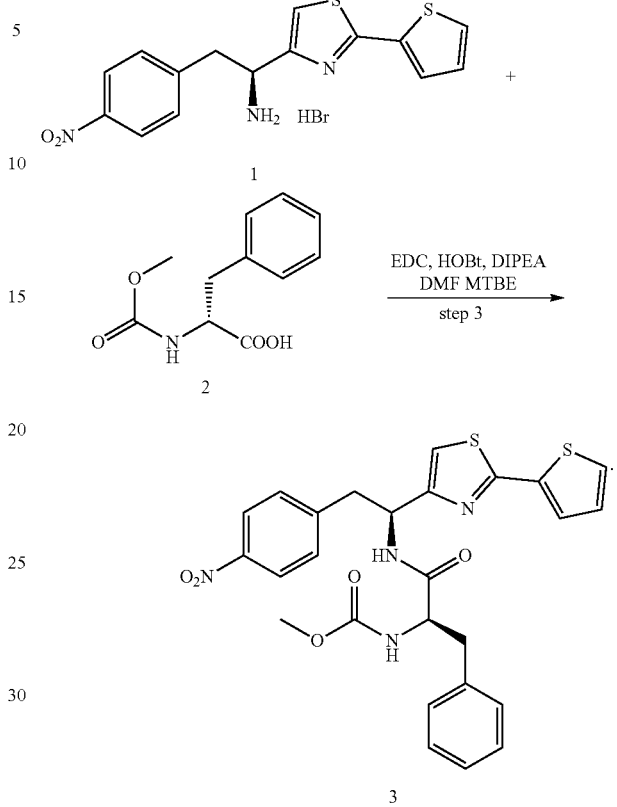

Synthesis for compound 3 was done by adding 1-(3-dimethylaminopropyl)-3-ethylcarbodiimide (EDC) (4.8 g, 27.2 mmol, 1.1 eq), followed by DIPEA (8.7 g, 4.28 g, 3 eq) to a solution of compound 1 (10.2 g, 24.7 mmol, 1.0 eq), compound 2 (5.53 g, 24.8 mmol, 1 eq), and 1-hydroxybenzotriazole (HOBt) (5.0 g, 41.6 mmol, 1.7 eq) in a mixture of DMF (70 mL) and MTBE (25 mL) at 0° C. The resulting mixture was stirred at 0° C. for 30 minutes, then allowed to warm to RT and stirred overnight. TLC analysis indicated that compound 1 was consumed. The reaction mixture was diluted with water (200 mL) and extracted with EtOAc (3×300 mL). The combined organic phase was washed with a diluted aqueous HCl solution (1 N, 200 mL), 5% aqueous NaHCO$_3$ (200 mL), water (200 mL) and brine (200 mL). The organic layer was then dried over Na$_2$SO$_4$ and concentrated to give 10 g of compound 3 as yellow solid. The yield was 75%. The crude product of compound 3 was directly used for the next step without further purification.

Figure 4:
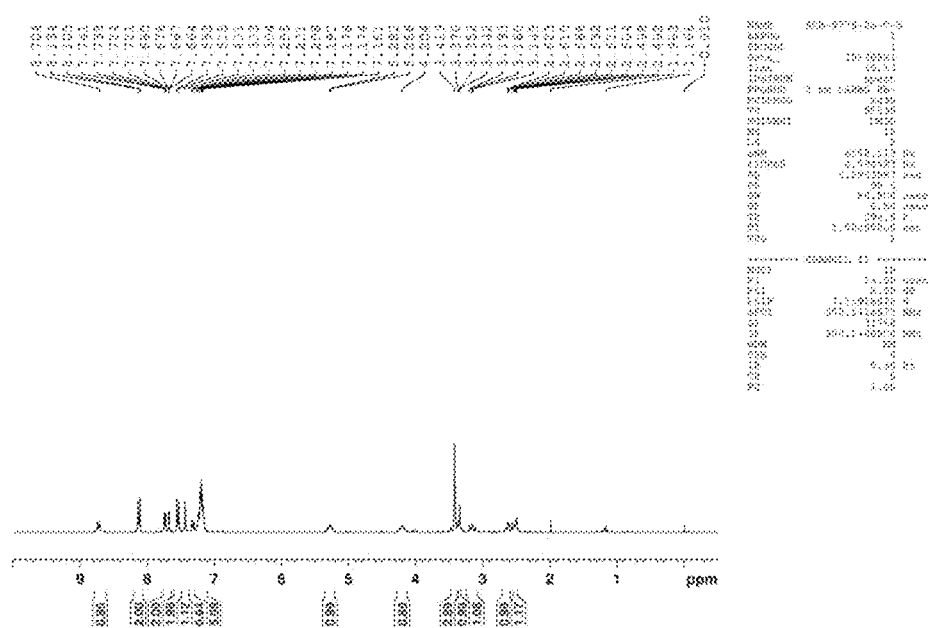
FIG. 4 displays the NMR data for the final product of step 3 of the synthesis of compound A.
Figure 5:
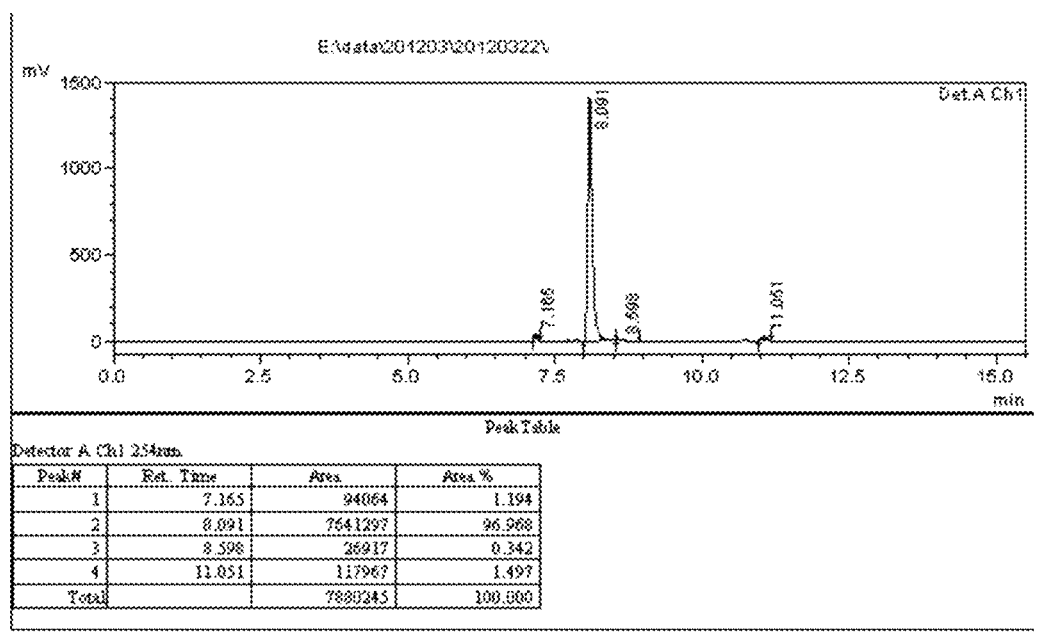
FIG. 5 displays the HPLC data for the final product of step 3 of the synthesis of compound A.
Figure 6:
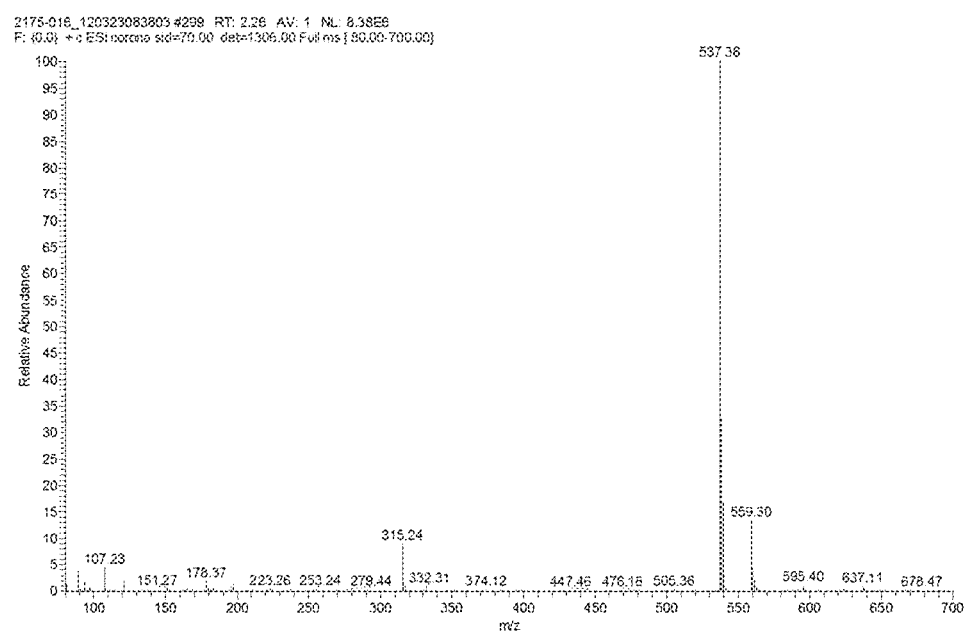
FIG. 6 displays the LCMS data for the final product of step 3 of the synthesis of compound A.

The analytical data for compound 3 were as follows: HPLC: 97% (FIG. 5); LCMS (ESI+): m/z 537 (M+H) (FIG. 6); $^1$H-NMR (300 MHz, DMSO-d$_6$) δ 8.72 (d, J=8.7 Hz, 1H), 8.12 (d, J=8.7 Hz, 2H), 7.73 (dd, J=0.9 Hz, 5.1 Hz, 1H), 7.67 (dd, J=0.9 Hz, 5.1 Hz, 1H), 7.54 (d, J=8.4 Hz, 2H), 7.43 (s, 1H), 7.32 (d, J=8.7 Hz, 1H), 7.25-7.10 (m, 6H), 5.23-5.31 (m, 1H), 4.16-4.23 (m, 1H), 3.41 (s, 3H), 3.34-3.37 (m, 1H), 3.11-3.19 (m, 1H), 2.61-2.66 (m, 1H), 2.49-2.53 (m, 1H) (FIG. 4).

Step 4 of the scheme is detailed below.

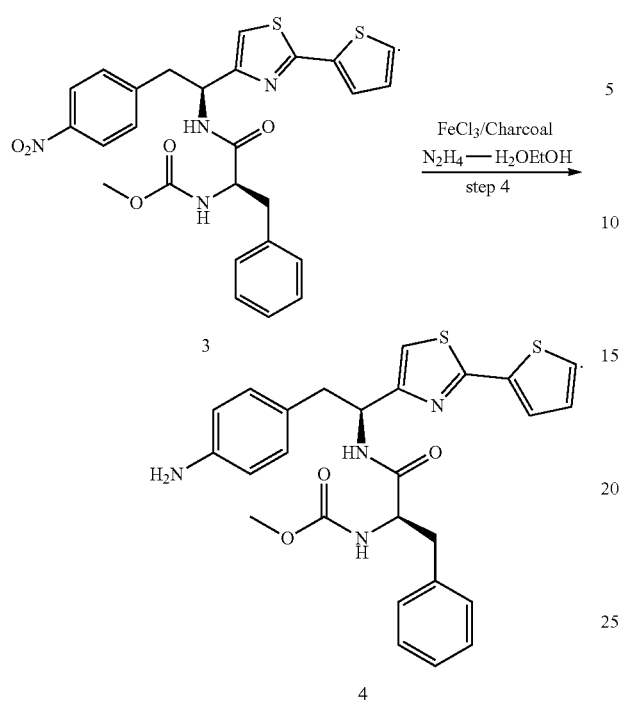

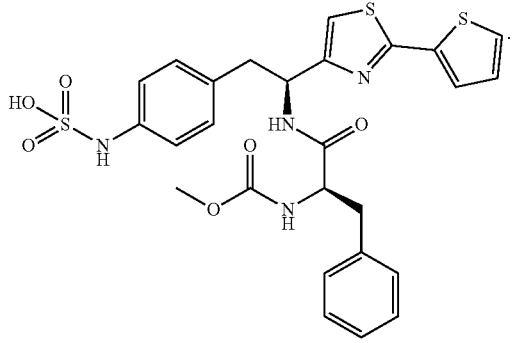

Synthesis for compound 4 was done by adding FeCl$_3$ (0.6 g, 3.7 mmol, 0.2 eq) and charcoal (4.0 g) to a solution of compound 3 (10 g, 18.7 mmol, 1.0 eq) in EtOH (400 mL). The mixture was heated to reflux and hydrazine hydrate (30.0 g, 600 mmol, 32.0 eq) was added. The reaction mixture was heated at reflux until compound 3 was completely consumed as indicated by TLC (~2 h). The charcoal and the inorganic salts were filtered off through a pad of Celite, and the Celite was washed with EtOH. The filtrate was concentrated to give 9.3 g of a crude product of compound 4 (yield 98.9%) as a white solid, which was directly used for the next step without further purification.

Figure 7:
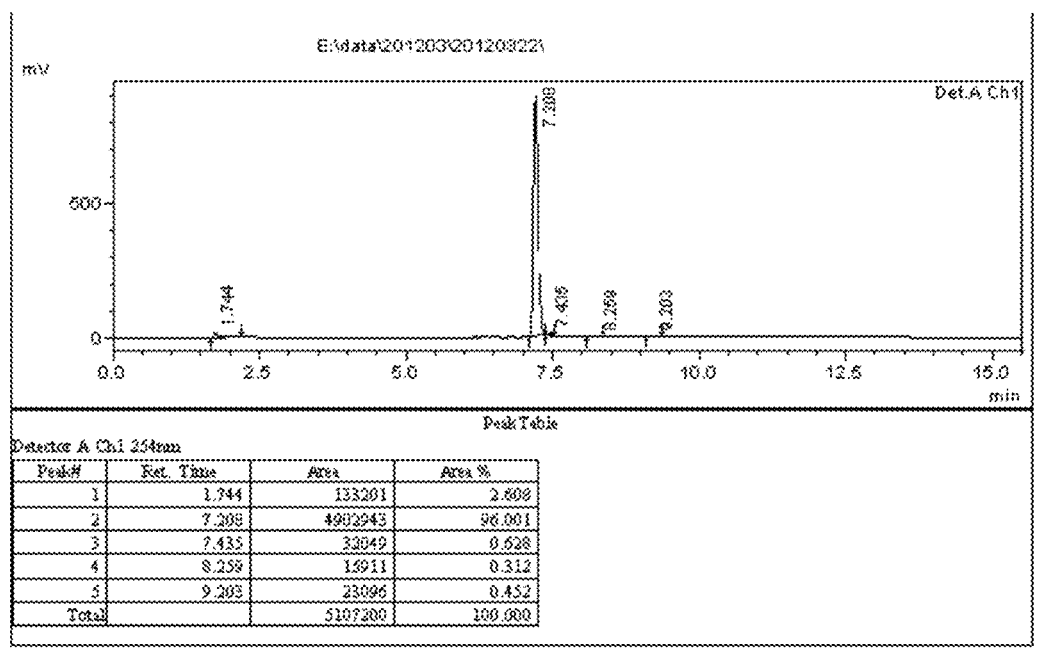
FIG. 7 displays the HPLC data for the final product of step 4 of the synthesis of compound A.
Figure 8:
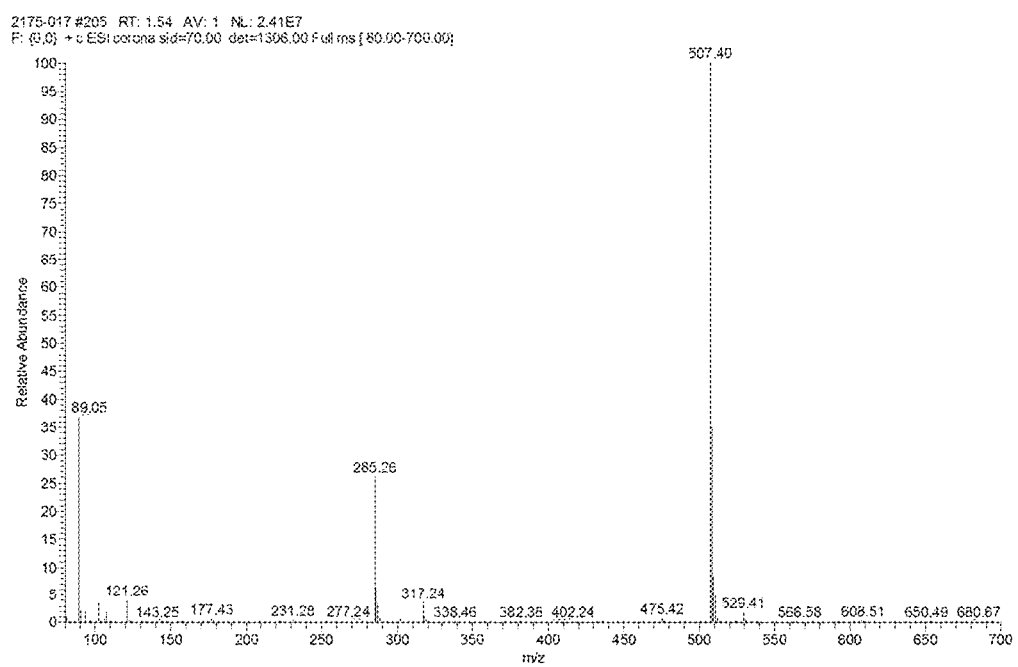
FIG. 8 displays the LCMS data for the final product of step 4 of the synthesis of compound A.
Figure 9:
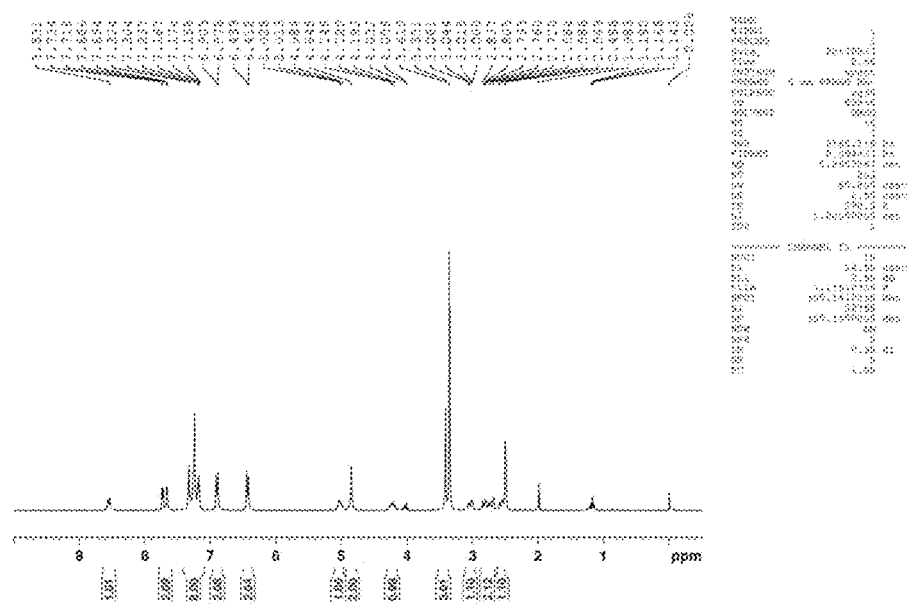
FIG. 9 displays the NMR data for the final product of step 4 of the synthesis of compound A.

The analytical data for compound 4 were as follows: HPLC: 96% (FIG. 7); LCMS (ESI+): m/z 507 (M+H) (FIG. 8); $^1$H-NMR (300 MHz, DMSO-d$_6$) δ 8.54 (d, J=8.7 Hz, 1H), 7.73 (d, J=4.8 Hz, 1H), 7.66 (d, J=3.6 Hz, 1H), 7.15-7.32 (m, 8H), 6.89 (d, J=8.1 Hz, 2H), 6.43 (d, J=8.1 Hz, 2H), 4.89-5.05 (m, 1H), 4.84 (s, 2H), 4.19-4.24 (m, 1H), 3.41 (s, 3H), 2.99-3.06 (m, 1H), 2.68-2.83 (m, 2H), 2.54-2.58 (m, 1H) (FIG. 9).

Step 5 of the scheme is detailed below.

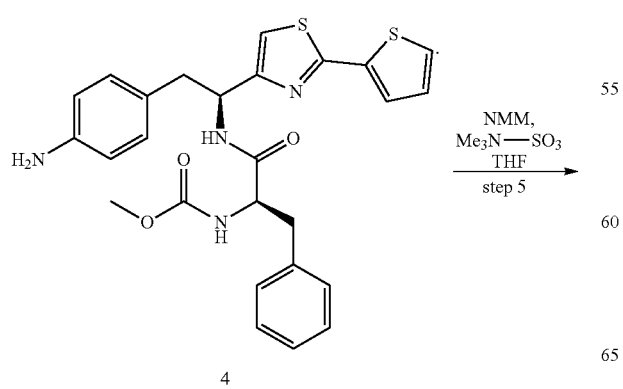

To create compound 5 Me$_3$NSO$_3$ (1.65 g, 11.9 mmol, 1.5 eq) and then NMM (1.45 g, 14.4 mmol, 1.8 eq) were added to a solution of compound 4 (4.0 g, 7.9 mmol, 1.0 eq) in dry THF (100 mL) at RT. The resulting mixture was heated to reflux and stirred overnight. TLC analysis of the reaction mixture indicated that compound 4 was not completely consumed. The reaction was stopped at that point. The reaction mixture was concentrated to dryness to afford the crude product of compound 5. The crude product of compound 5 was purified by flash column chromatography to give compound 5 (3.3 g, yield 71.7%) as a white solid containing traces of residual ethyl acetate.

Figure 10:
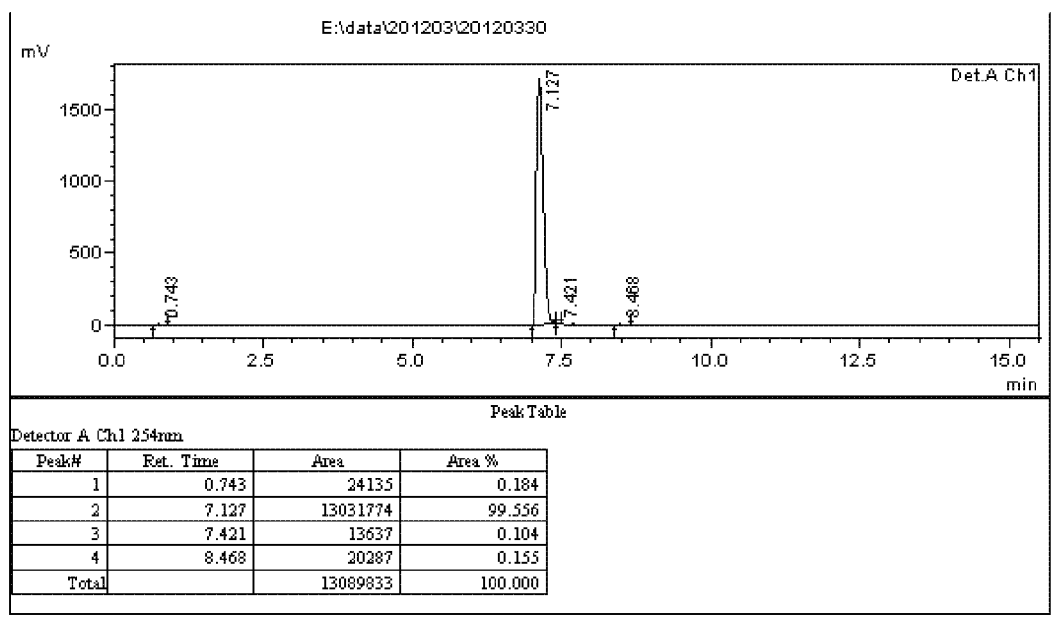
FIG. 10 displays the HPLC data for the final product of step 5 of the synthesis of compound A.
Figure 11:
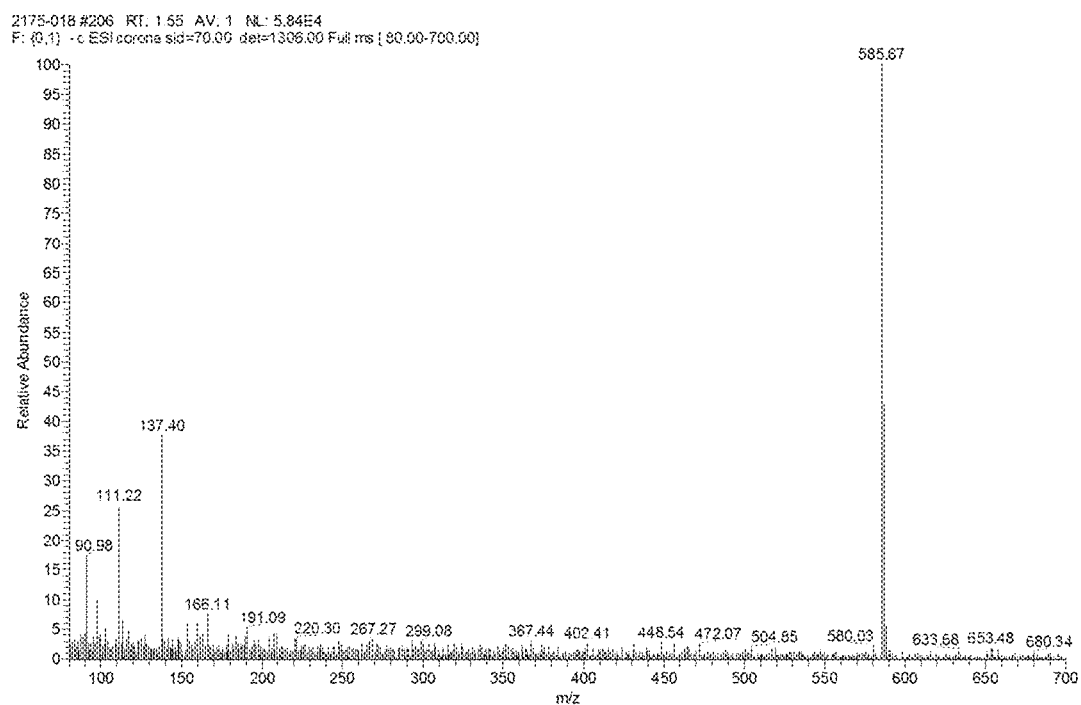
FIG. 11 displays the LCMS data for the final product of step 5 of the synthesis of compound A.
Figure 12:
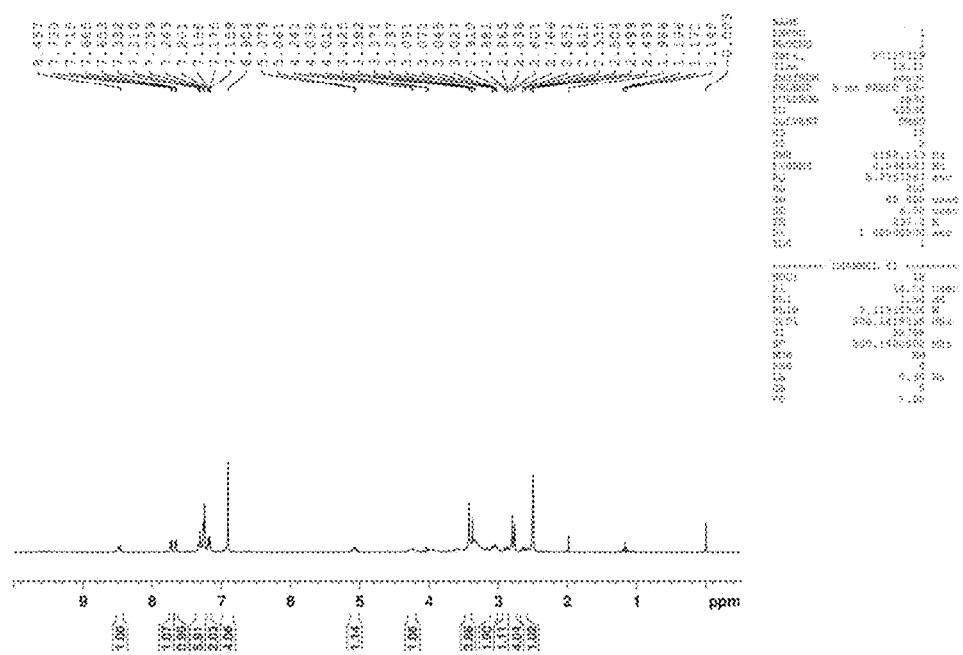
FIG. 12 displays the NMR data for the final product of step 5 of the synthesis of compound A.

The analytical data for compound 5 were as follows: HPLC: 99.6% (FIG. 10); LCMS (ESI$^-$): m/z 585 (M−H) (FIG. 11); $^1$H-NMR (300 MHz, DMSO-d$_6$) δ 8.47 (d, J=8.7 Hz, 1H), 7.72 (d, J=4.5 Hz, 1H), 7.66 (d, J=3.6 Hz, 1H), 7.24-7.33 (m, 6H), 7.16-7.20 (m, 2H), 6.90 (s, 4H), 5.06-5.08 (m, 1H), 4.20-4.26 (m, 1H), 3.42 (s, 3H), 3.02-3.09 (m, 2H), 2.86-2.91 (m, 1H), 2.76-2.83 (m, 2H), 2.61-2.65 (m, 1H) (FIG. 12).

Step 6 of the scheme is detailed below.

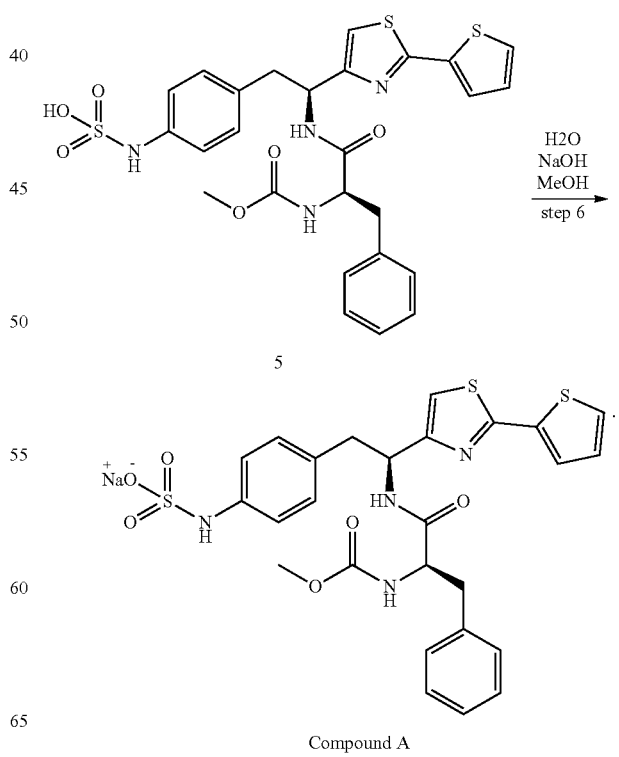

To create compound A an aqueous solution of NaOH (164 mg in 245 mg of H$_2$O, 4.1 mmol, 1.2 eq) was added dropwise at RT over 5 min to a solution of compound 5 (2.0 g, 3.4 mmol, 1.0 eq) in MeOH (20 mL) and the resulting reaction mixture was stirred at RT for 2 h. The solid product was collected by vacuum filtration, washed with EtOAc (100 mL), and then Et$_2$O (100 mL). 1.0 g of compound A was obtained as white solid. The yield was 48.3%.

Figure 13:
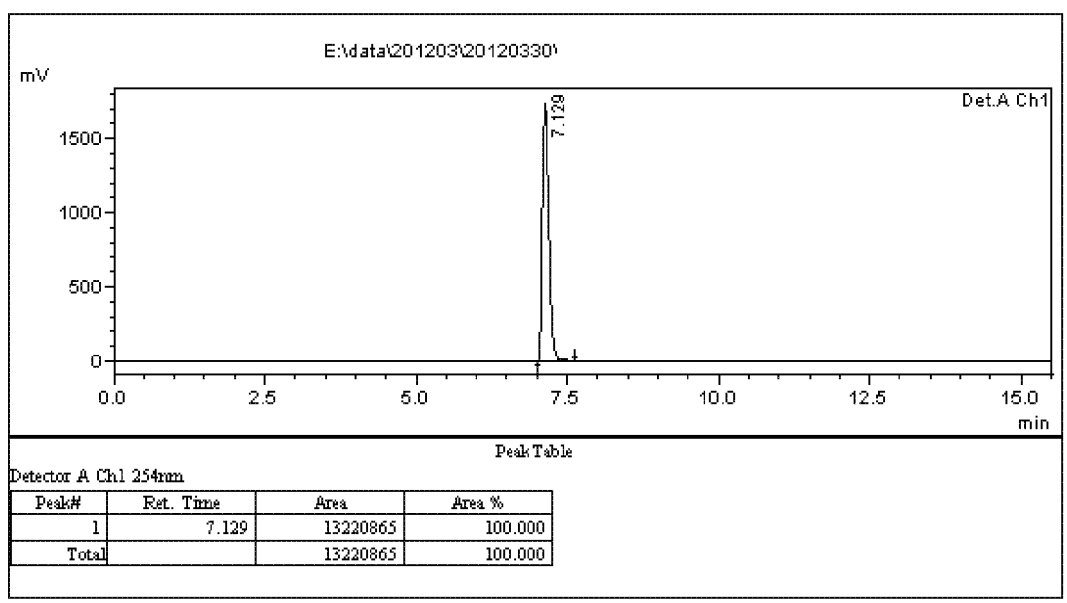
FIG. 13 displays the HPLC data for compound A.
Figure 14:
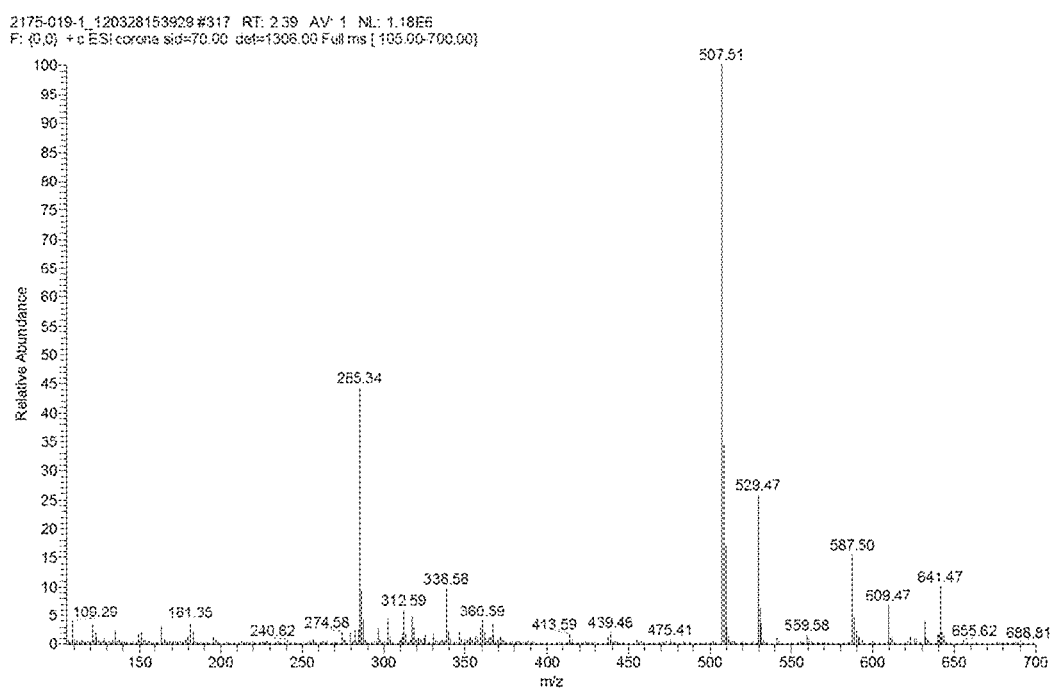
FIG. 14 displays the LCMS data for compound A.
Figure 15:
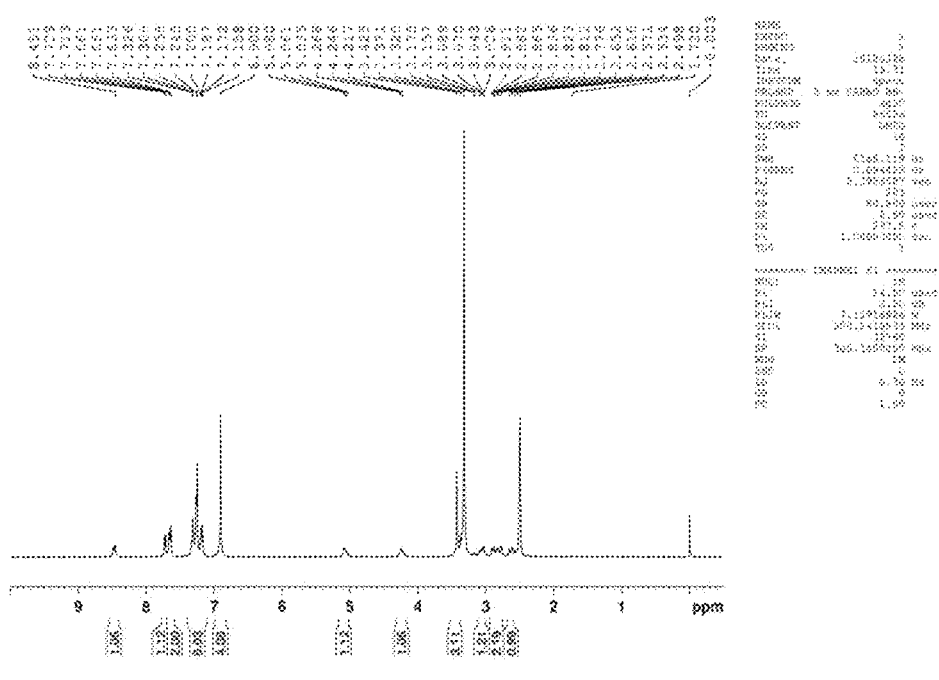
FIG. 15 displays the NMR data for compound A.

Analytical data for compound A were as follows: HPLC: ~100% (FIG. 13); LCMS (ESI+): m/z 587 (M-Na+2H) (FIG. 14); $^1$H-NMR (300 MHz, DMSO-d$_6$) δ 8.47 (d, J=8.4 Hz, 1H), 7.72 (d, J=4.8 Hz, 1H), 7.63-7.66 (m, 2H), 7.16-7.33 (m, 8H), 6.90 (s, 4H), 5.03-5.08 (m, 1H), 4.21-4.26 (m, 1H), 3.42 (s, 3H), 3.03-3.09 (m, 1H), 2.77-2.91 (m, 2H), 2.57-2.65 (m, 1H) (FIG. 15).

Step 1 of the pathway to synthesize compound C is detailed in the reaction scheme below:

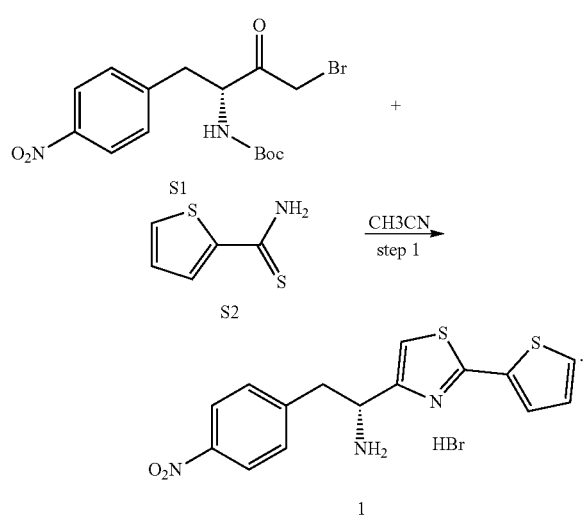

To create compound 1 a solution of compound S1 (14.9 g, ~74% purity, counted as 11 g of S1, 28.4 mmol, 1.0 eq) and compound S2 (4.1 g, 29.8 mmol, 1.05 eq) in CH$_3$CN (300 mL) was heated at reflux for 5 h. TLC analysis indicated that compound S1 was almost consumed. The reaction mixture was cooled to RT. The resulting solid was collected by vacuum filtration to provide 7.8 g of the crude product of compound 1.

Figure 18:
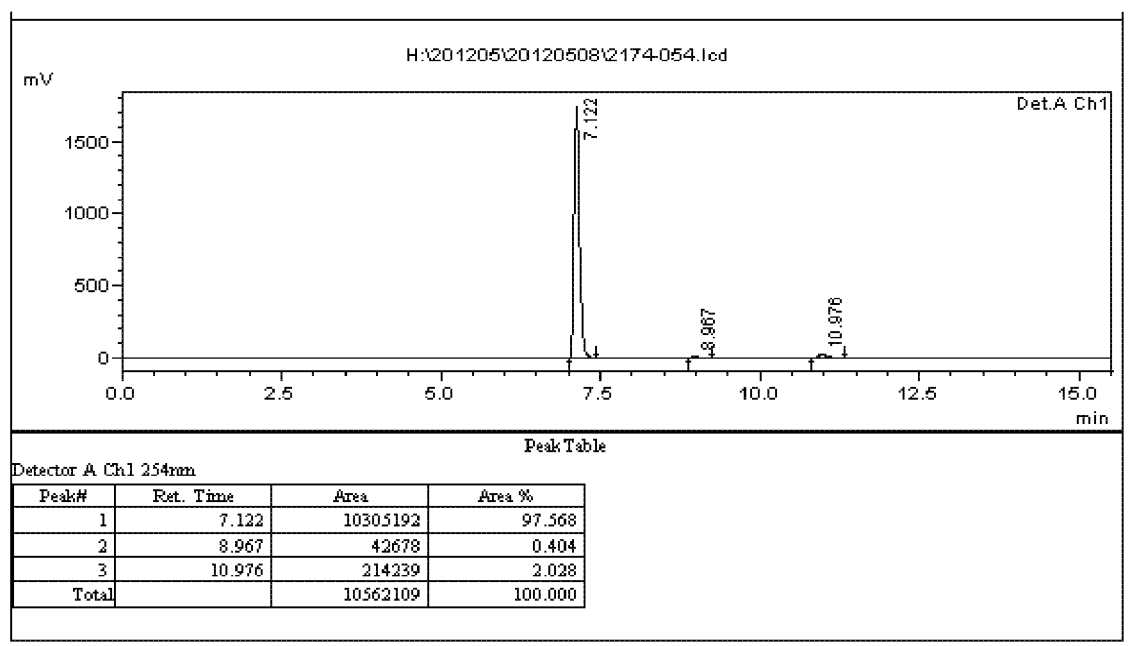
FIG. 18 displays the HPLC data for the final product of step 1 of the synthesis of compound C.
Figure 19:
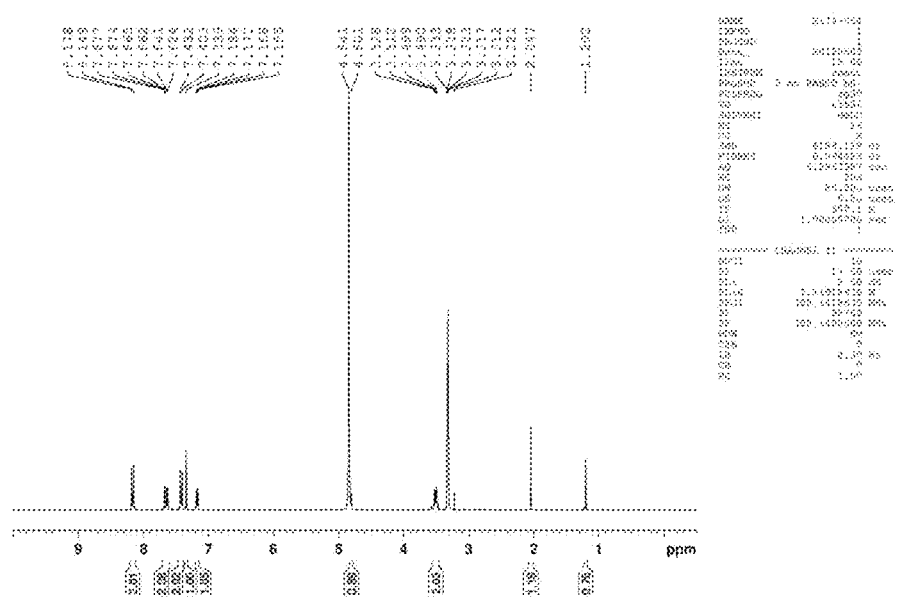
FIG. 19 displays the NMR data for the final product of step 1 of the synthesis of compound C.

The analytical data for compound 1 were as follows: HPLC: 97.5% (FIG. 18); $^1$H-NMR (300 MHz, CD$_3$OD) δ 8.17 (d, J=8.7 Hz, 2H), 7.63 (d, J=5.1 Hz, 2H), 7.43 (d, J=3.7 Hz, 2H), 7.33 (s, 1H), 7.16 (d, J=8.7 Hz, 1H), 4.84 (s, 1H), 3.58-3.43 (m, 2H) (FIG. 19).

Step 3 of the scheme is detailed below. Compound 3 was synthesized using the same procedure for step 3 for the synthesis of compound A.

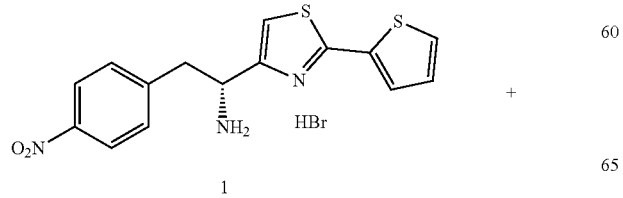

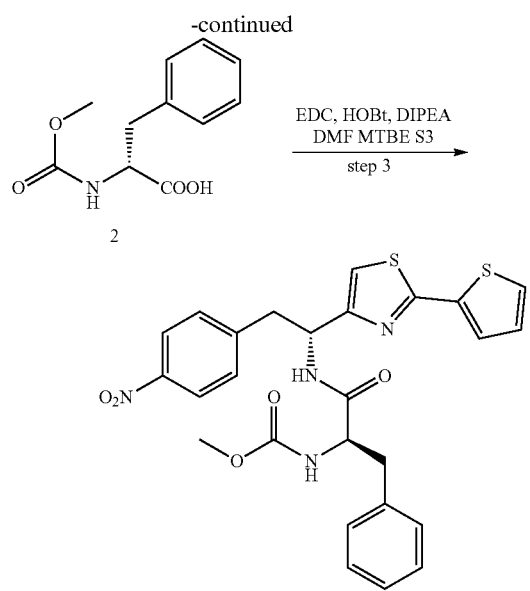

Figure 20:
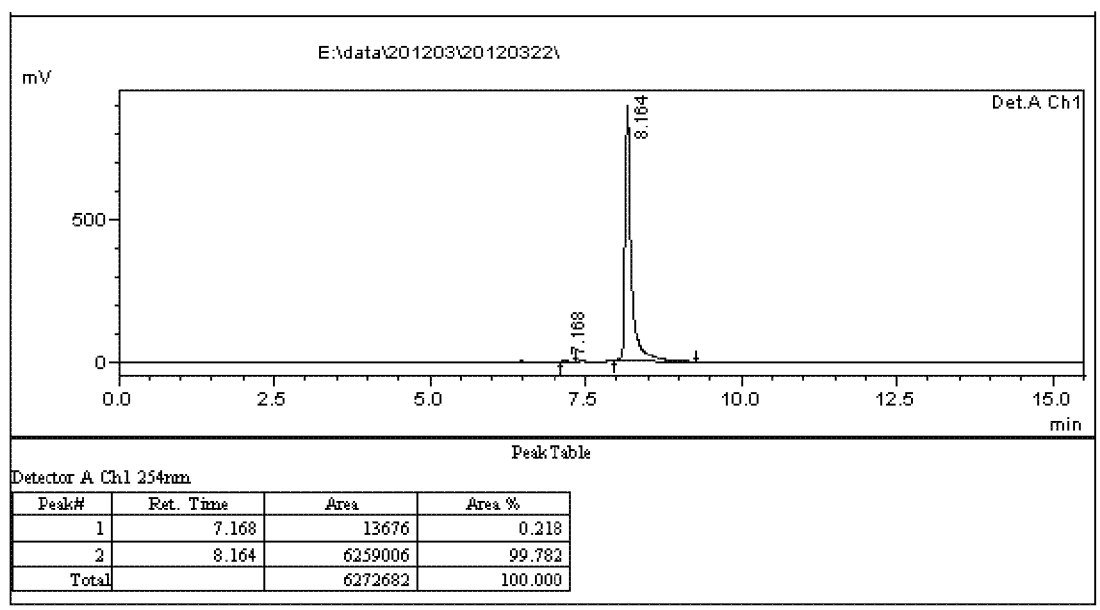
FIG. 20 displays the HPLC data for the final product of step 3 of the synthesis of compound C.
Figure 21:
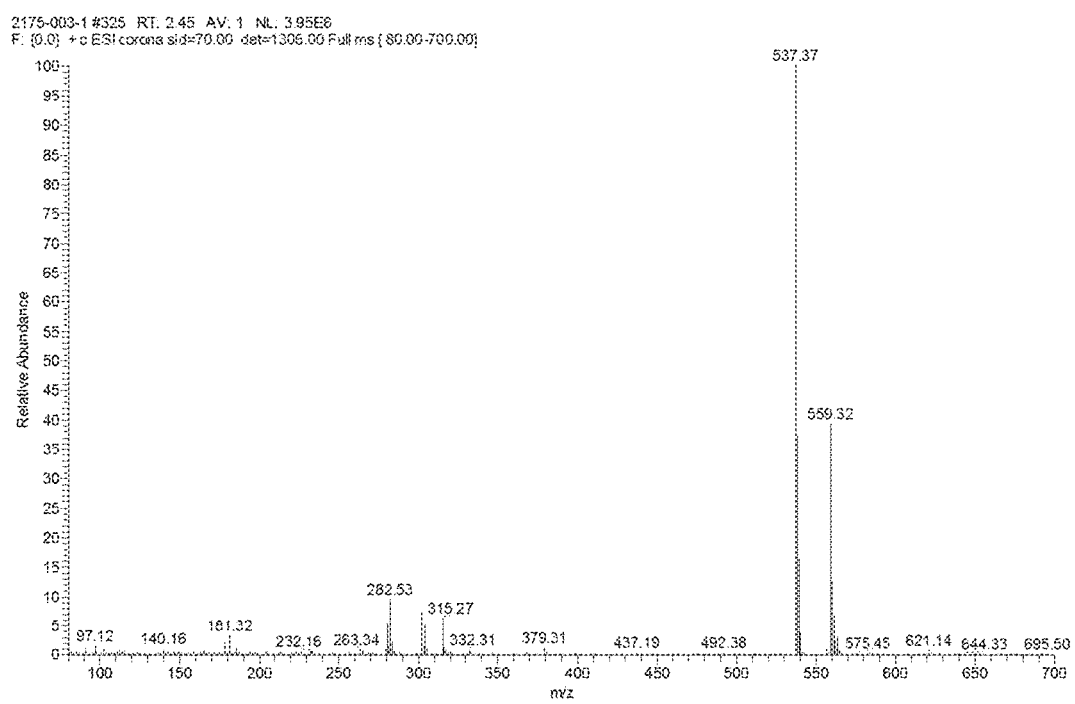
FIG. 21 displays the LCMS data for the final product of step 3 of the synthesis of compound C.
Figure 22:
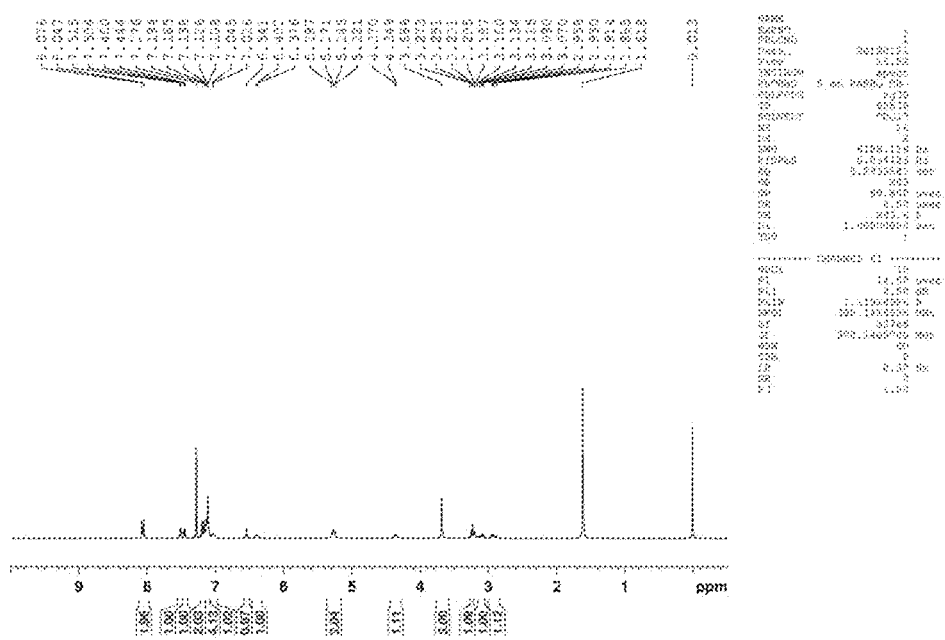
FIG. 22 displays the NMR data for the final product of step 3 of the synthesis of compound C.

The analytical data for compound 3 were as follows: HPLC: 97.8% (FIG. 20); LCMS (ESI+): m/z 537 (M+H) (FIG. 21); $^1$H-NMR (300 MHz, CDCl$_3$) δ 8.07 (d, J=8.5 Hz, 2H), 7.51 (d, J=3.4 Hz, 1H), 7.45 (d, J=5.0 Hz, 1H), 7.19 (d, J=8.5 Hz, 2H), 7.15-7.08 (m, 4H), 7.06-6.98 (m, 1H), 6.54 (s, 1H), 6.45-6.35 (m, 1H), 5.32-5.21 (m, 2H), 4.42-4.30 (m, 1H), 3.68 (s, 3H), 3.32-3.20 (m, 1H), 3.18-3.02 (m, 1H), 2.98-2.85 (m, 1H) (FIG. 22).

Step 4 of the scheme is detailed below. Compound 4 was synthesized using the same procedure for step 4 for the synthesis of compound A.

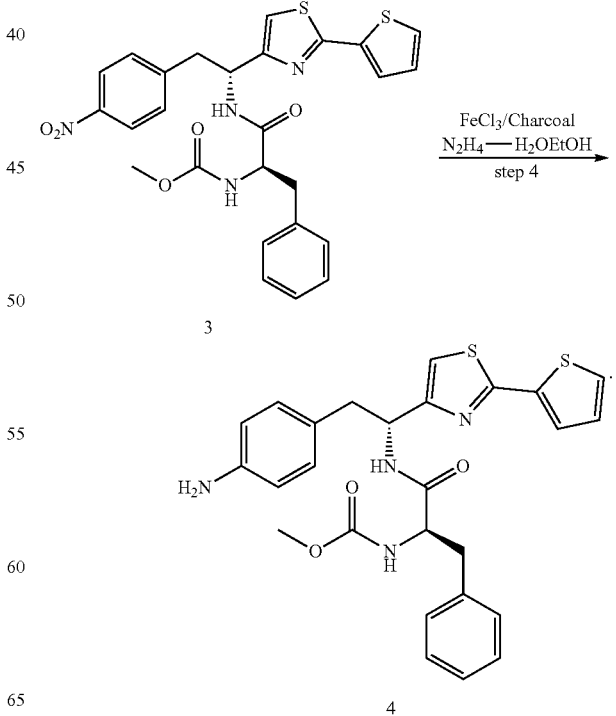

Figure 23:
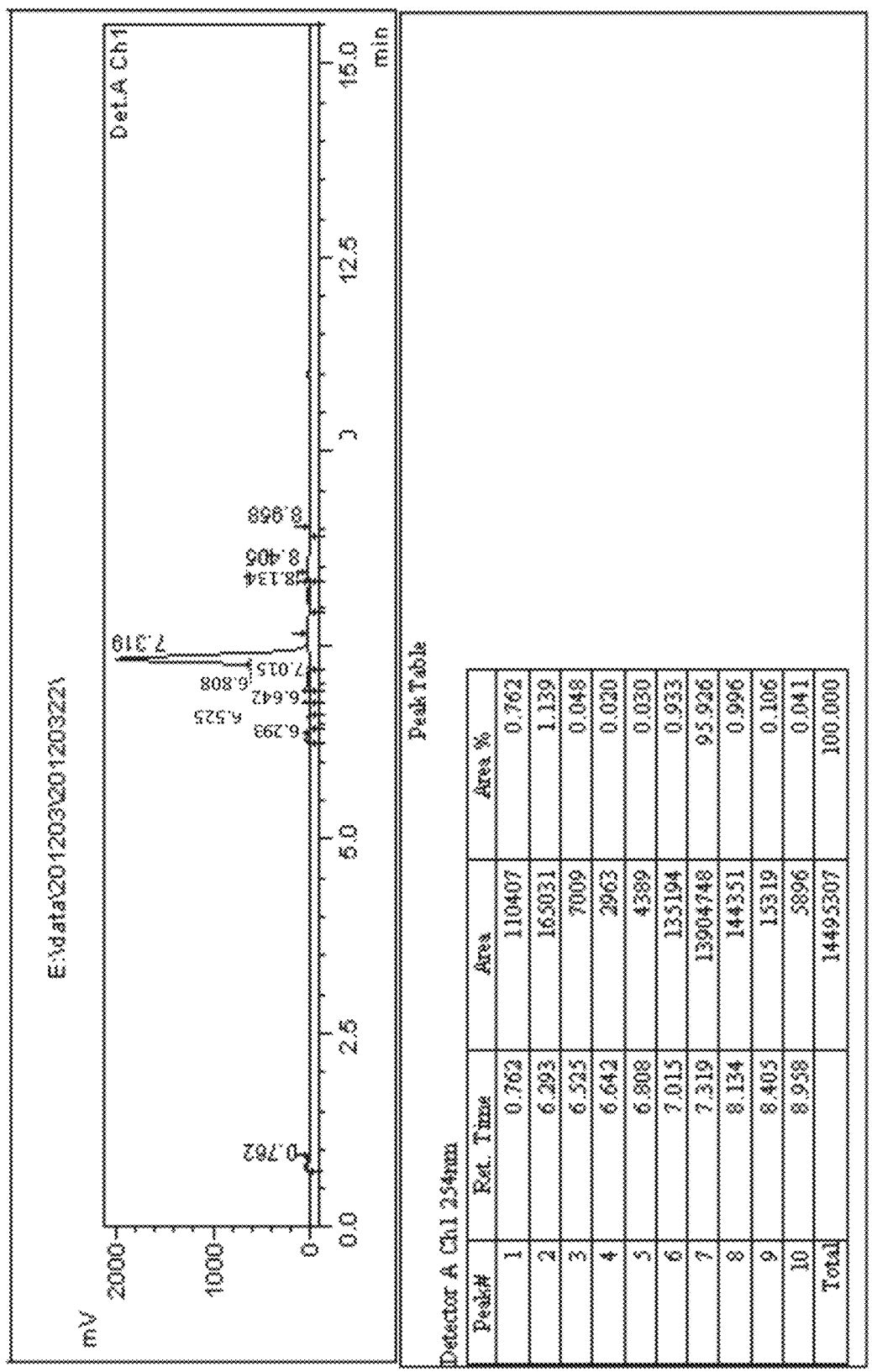
FIG. 23 displays the HPLC data for the final product of step 4 of the synthesis of compound C.
Figure 24:
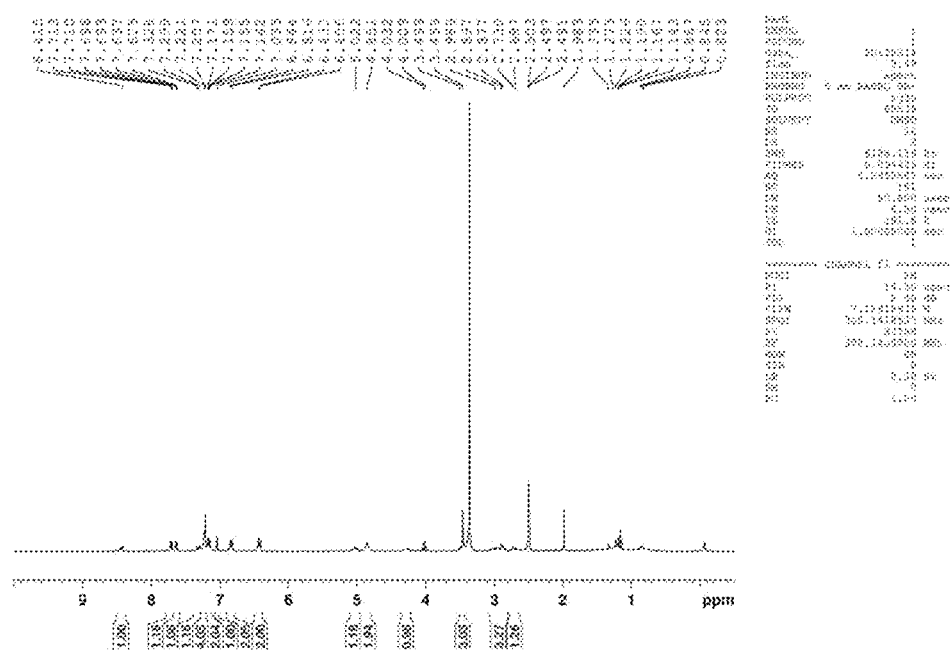
FIG. 24 displays the LCMS data for the final product of step 4 of the synthesis of compound C.
Figure 25:
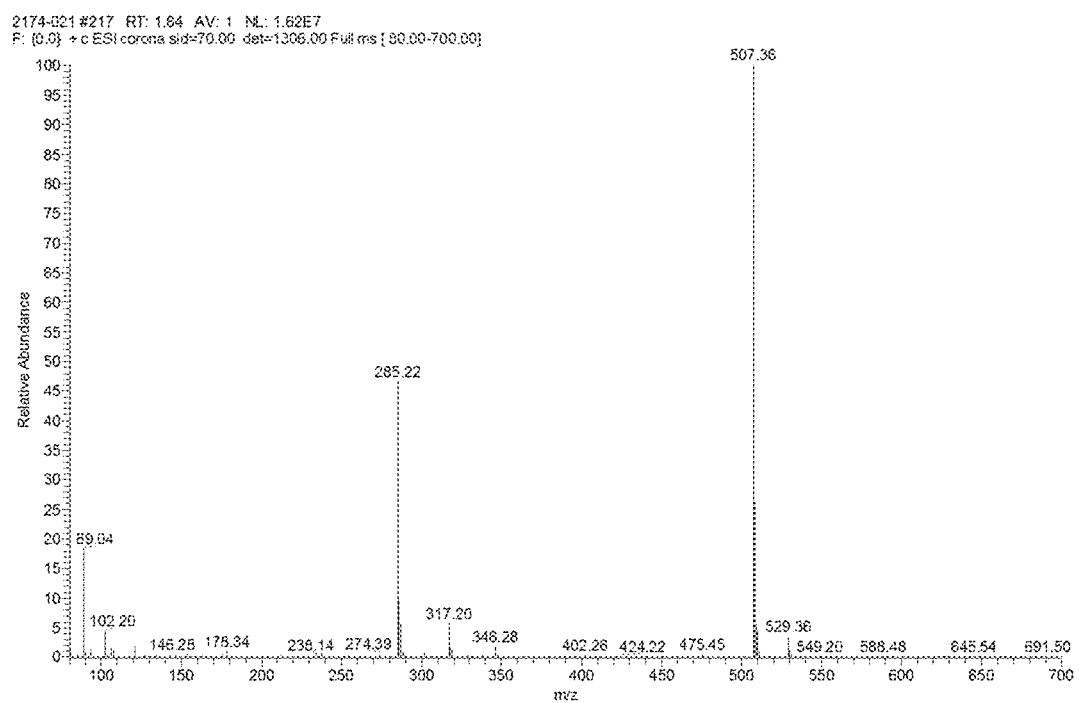
FIG. 25 displays the NMR data for the final product of step 4 of the synthesis of compound C.

The analytical data for compound 4 were as follows: HPLC: 95.9% (FIG. 23); LCMS (ESI+): m/z 507 (M+H) (FIG. 24); $^1$H-NMR (300 MHz, DMSO-d$_6$) δ 8.44 (d, J=8.4 Hz, 1H), 7.70 (d, J=5.0 Hz, 1H), 7.63 (d, J=3.6 Hz, 1H), 7.32 (d, J=8.1 Hz, 1H), 7.26-7.18 (m, 4H), 7.20-7.11 (m, 2H), 7.03 (s, 1H), 6.84 (d, J=8.2 Hz, 2H), 6.43 (d, J=8.2 Hz, 2H), 5.10-4.92 (m, 1H), 4.35-4.21 (m, 1H), 3.45 (s, 3H), 3.08-2.93 (m, 1H), 2.90-2.78 (m, 2H), 2.75-2.64 (m, 1H) (FIG. 25).

Step 5 of the scheme is detailed below. Compound 5 was synthesized using the same procedure for step 5 for the synthesis of compound A.

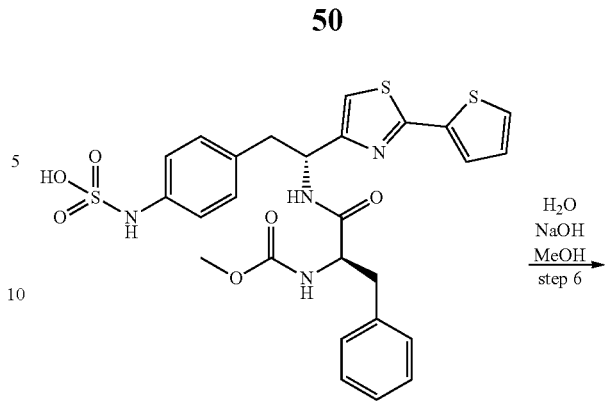

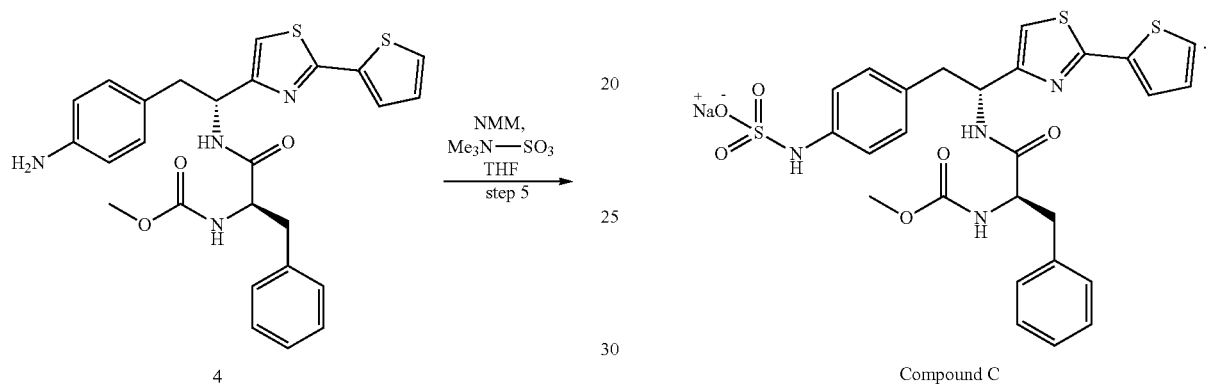

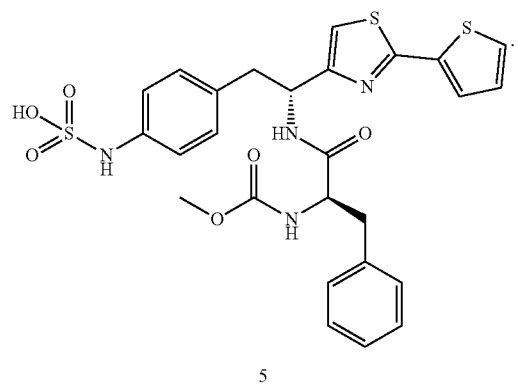

Figure 26:
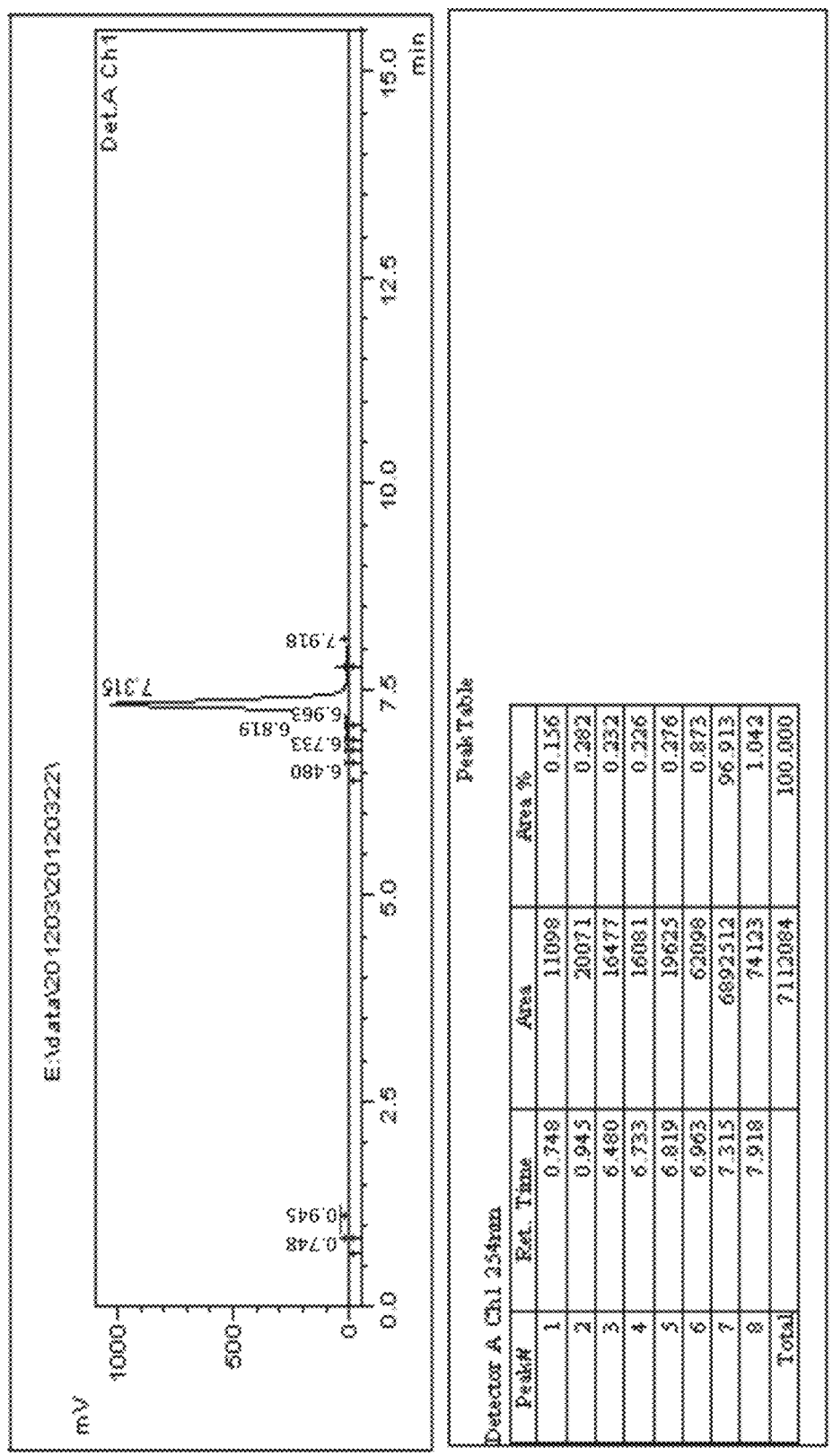
FIG. 26 displays the HPLC data for the final product of step 5 of the synthesis of compound C.
Figure 27:
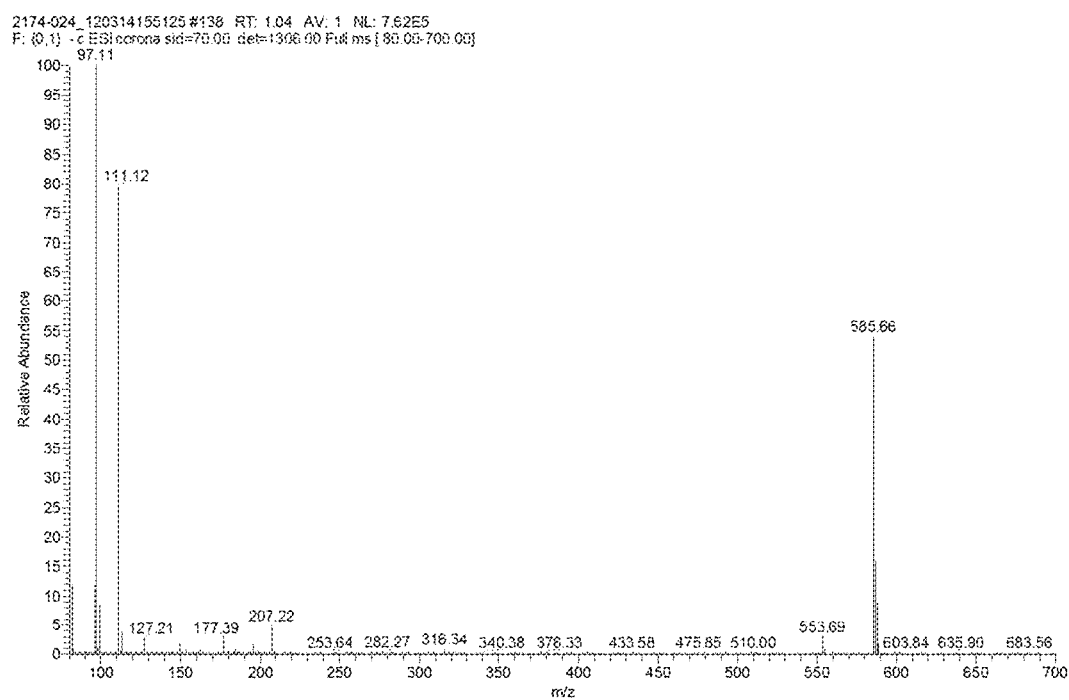
FIG. 27 displays the LCMS data for the final product of step 5 of the synthesis of compound C.
Figure 28:
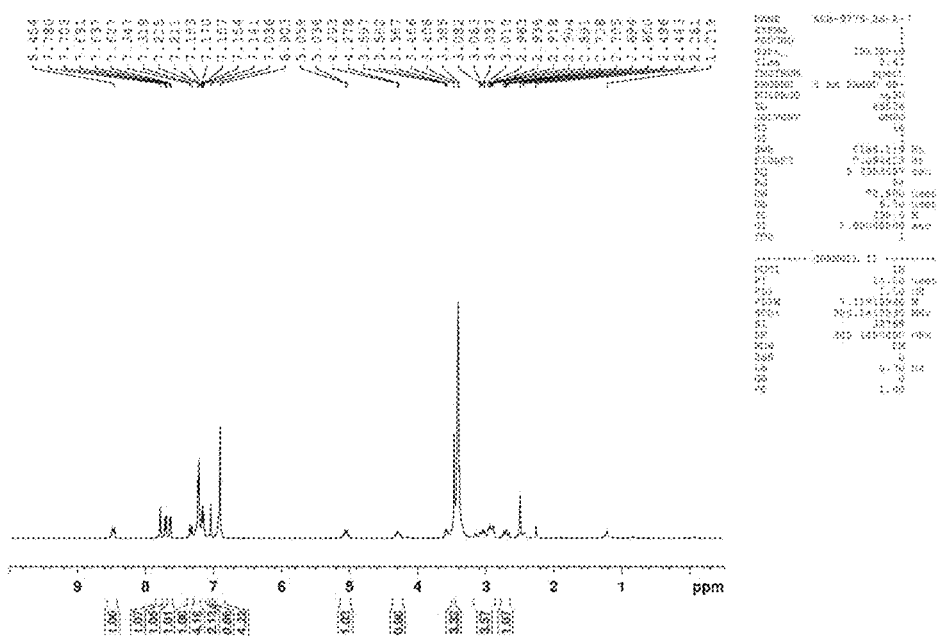
FIG. 28 displays the NMR data for the final product of step 5 of the synthesis of compound C.

The analytical data for compound 5 were as follows: HPLC: 96.9% (FIG. 26); LCMS (ESI-): m/z 585 (M-H) (FIG. 27); $^1$H-NMR (300 MHz, DMSO-d$_6$) δ 8.46 (d, J=8.3 Hz, 1H), 7.78 (s, 1H), 7.70 (d, J=5.0 Hz, 1H), 7.63 (d, J=3.0 Hz, 1H), 7.32 (d, J=8.6 Hz, 1H), 7.28-7.15 (m, 4H), 7.18-7.12 (m, 2H), 7.03 (s, 1H), 6.90 (s, 4H), 5.14-5.02 (m, 1H), 4.35-4.22 (m, 1H), 3.46 (s, 3H), 3.13-3.01 (m, 1H), 2.98-2.88 (m, 2H), 2.75-2.64 (m, 1H) (FIG. 28).

Step 6 of the scheme is detailed below. Compound C was synthesized using the same procedure as described for compound A.

Figure 29:
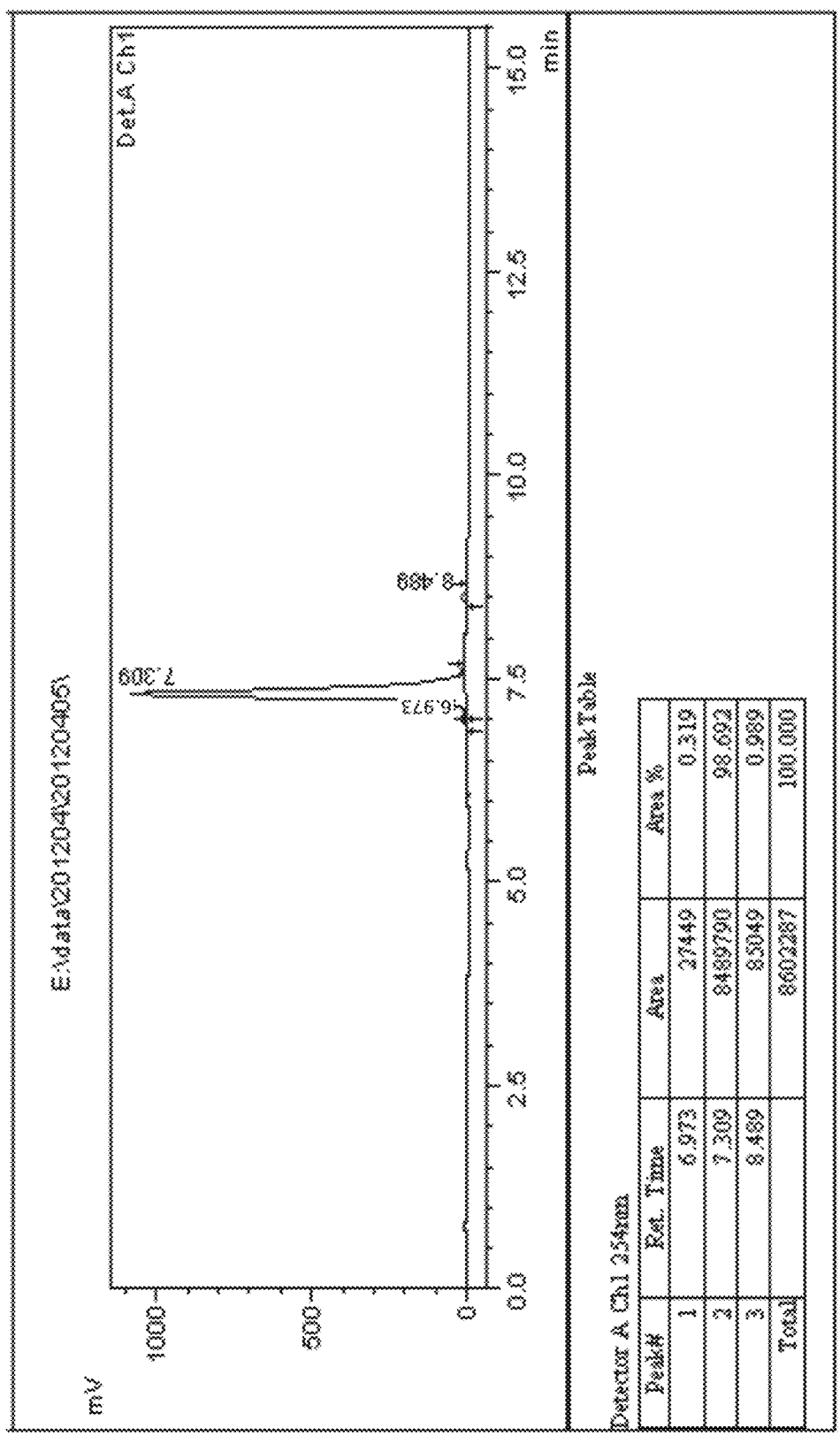
FIG. 29 displays the HPLC data for compound C.
Figure 30:
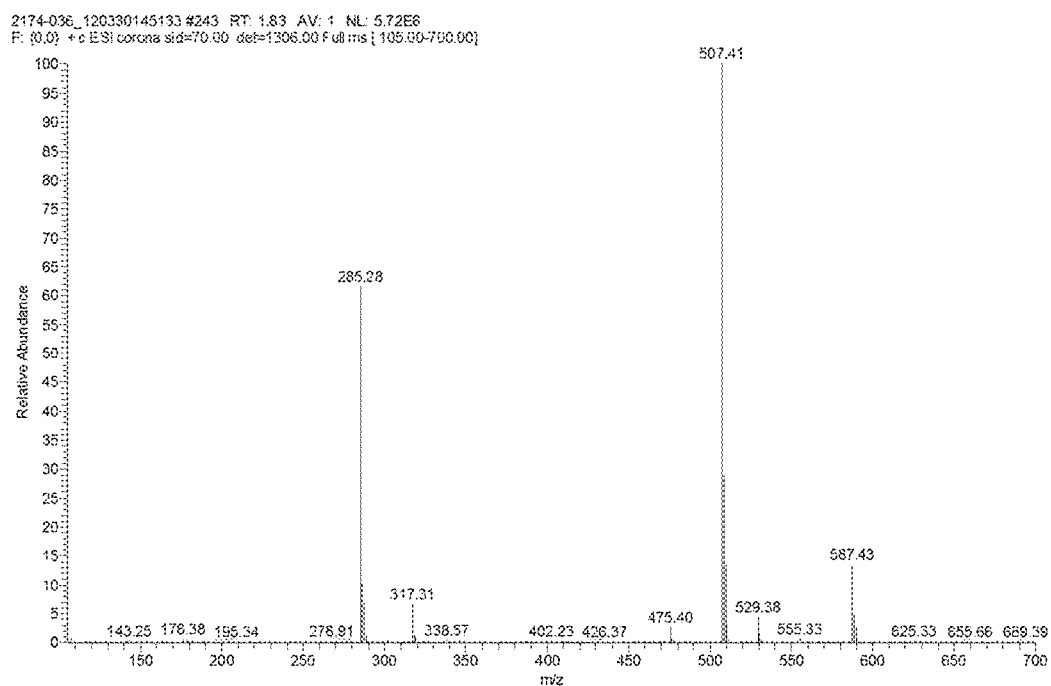
FIG. 30 displays the LCMS data for compound C.
Figure 31:
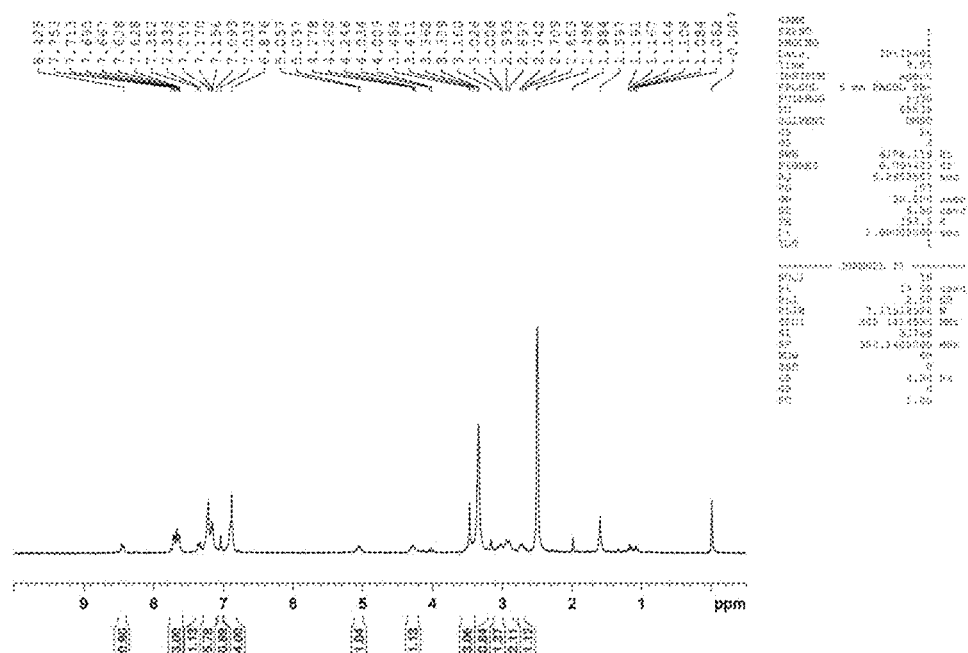
FIG. 31 displays the NMR data for compound C.

The analytical data for compound C were as follows: HPLC: 98.7% (FIG. 29); LCMS (ESI+): m/z 587 (M-Na+ 2H) (FIG. 30); $^1$H-NMR (300 MHz, DMSO-d$_6$) δ 8.46 (d, J=8.0 Hz, 1H), 7.75-7.61 (m, 3H), 7.36 (d, J=8.7 Hz, 1H), 7.28-7.12 (m, 6H), 7.03 (s, 1H), 6.87 (s, 4H), 5.05 (m, 1H), 4.27 (m, 1H), 3.46 (s, 3H), 3.10-3.01 (m, 1H), 3.10-2.85 (m, 2H), 2.82-2.65 (m, 1H) (FIG. 31).

Step 3 of the reaction used to create compound B is detailed in the reaction scheme shown below. Compound 3 was synthesized using the same procedure for step 3 for the synthesis of compound A.

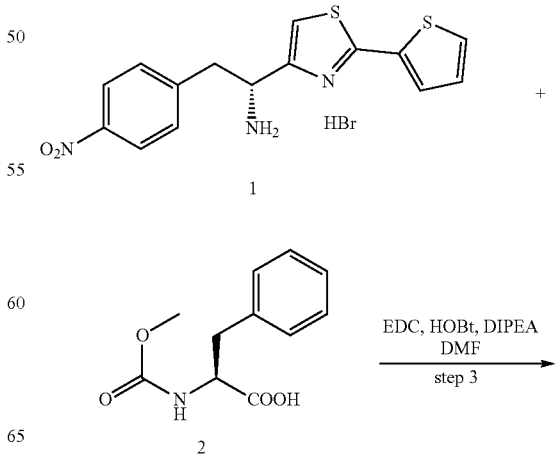

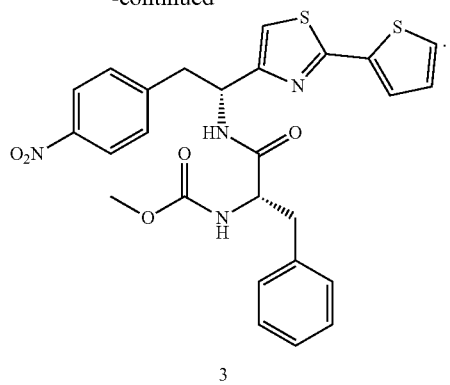

3

Figure 32:
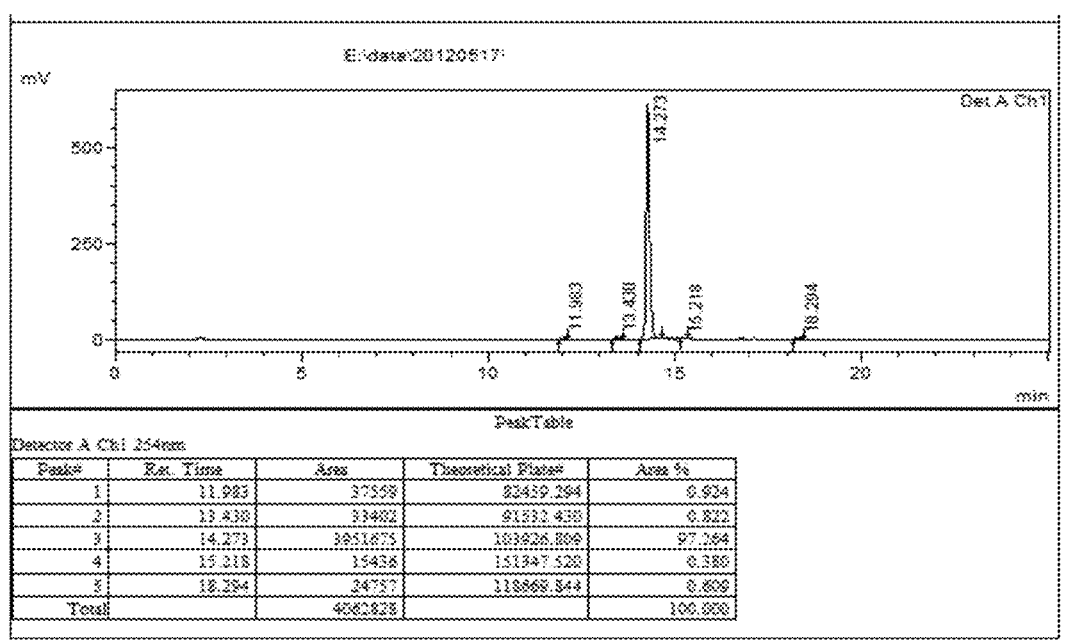
FIG. 32 displays the HPLC data for the final product of step 3 of the synthesis of compound B.
Figure 33:
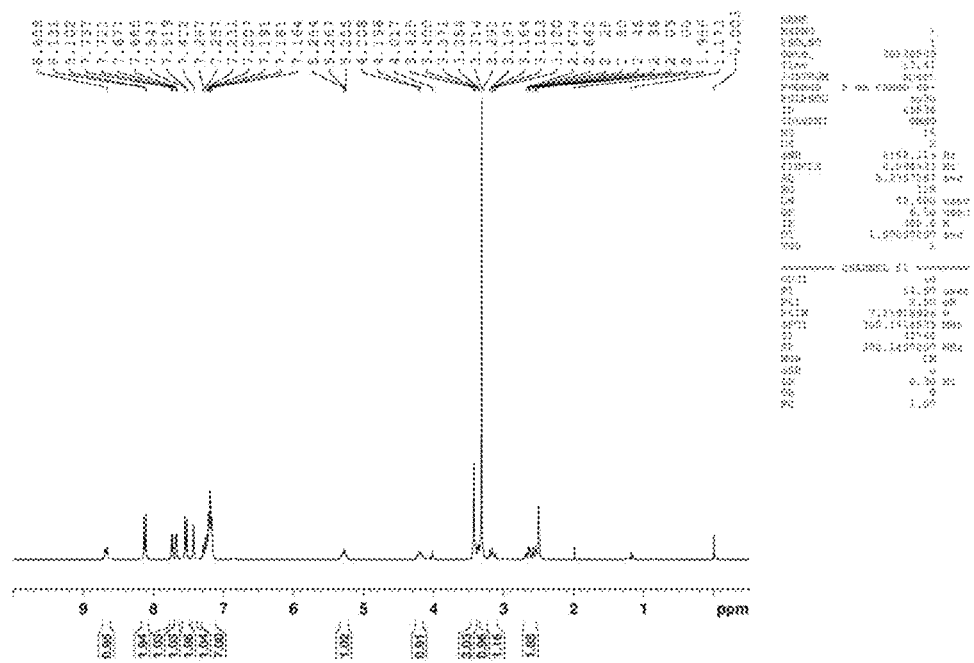
FIG. 33 displays the LCMS data for the final product of step 3 of the synthesis of compound B.
Figure 34:
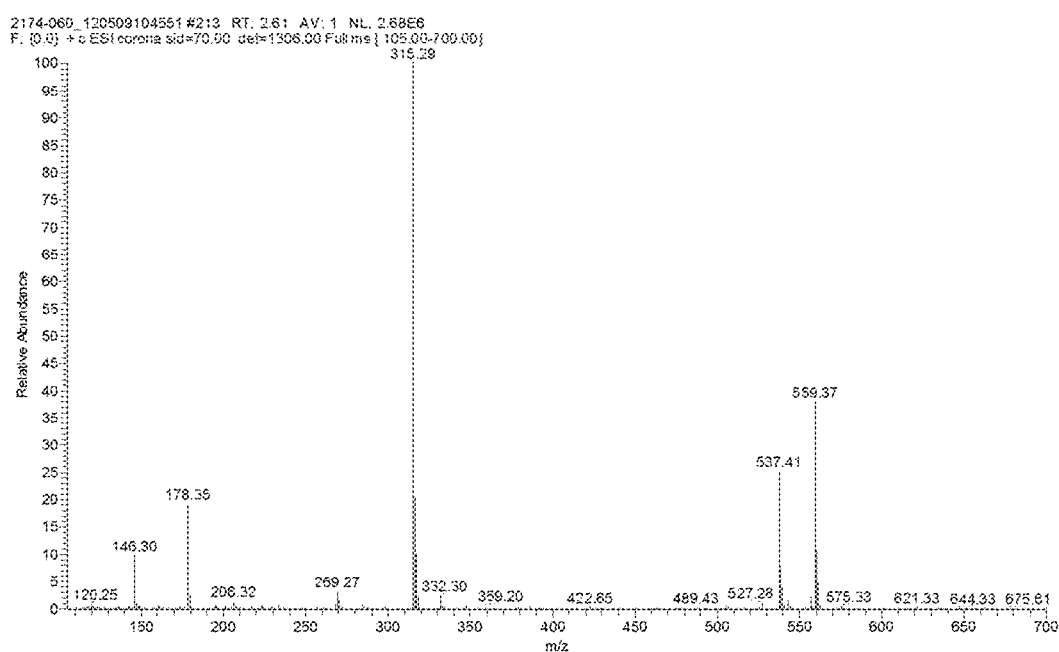
FIG. 34 displays the NMR data for the final product of step 3 of the synthesis of compound B.

The analytical data for Compound 3, as shown above, were as follows: HPLC: 97.3% (FIG. 32); LCMS (ESI+): m/z 537 (M+H) (FIG. 33); $^1$H-NMR (300 MHz, DMSO-d$_6$) δ 8.68 (d, J=8.7 Hz, 1H), 8.13 (d, J=8.6 Hz, 2H), 7.73 (d, J=4.3 Hz, 1H), 7.67 (d, J=3.6 Hz, 1H), 7.52 (d, J=8.6 Hz, 2H), 7.42 (s, 1H), 7.30-7.11 (m, 7H), 5.35-5.18 (m, 1H), 4.28-4.14 (m, 1H), 3.42 (s, 3H), 3.39-3.32 (m, 1H), 3.22-3.08 (m, 1H), 2.71-2.53 (m, 2H) (FIG. 34).

Step 4 of the reaction used to create compound B is detailed in the reaction scheme below. Compound 4 was synthesized using the same procedure for step 4 for the synthesis of compound A.

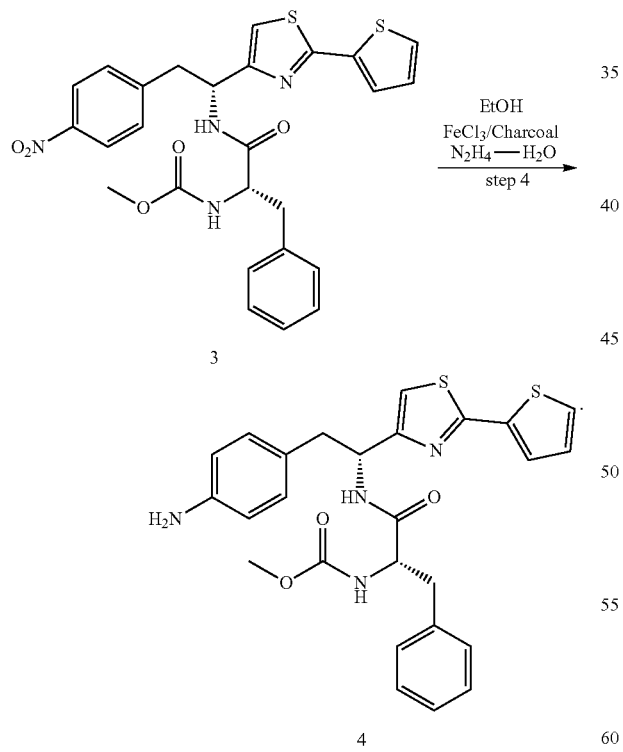

Figure 35:
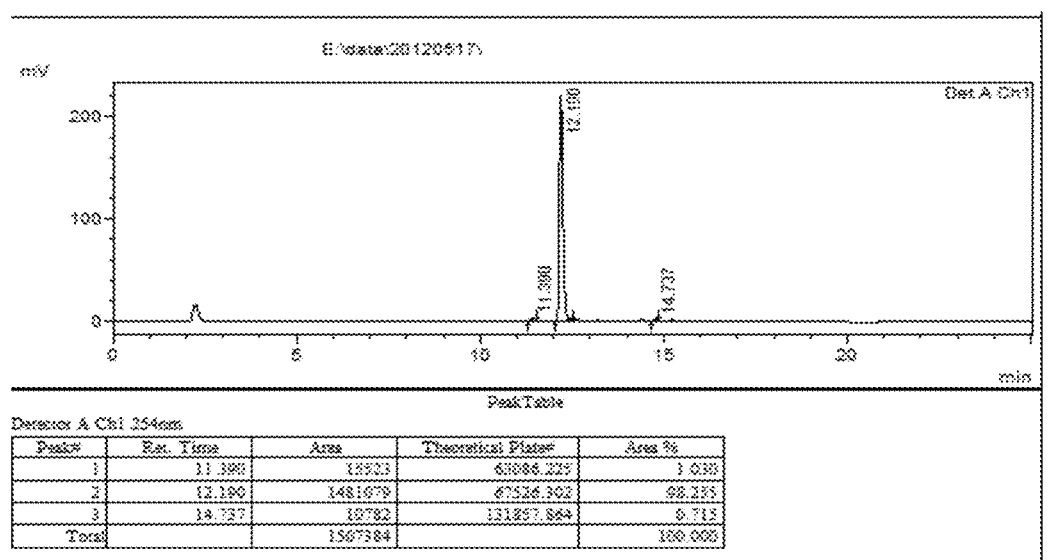
FIG. 35 displays the HPLC data for the final product of step 4 of the synthesis of compound B.
Figure 36:
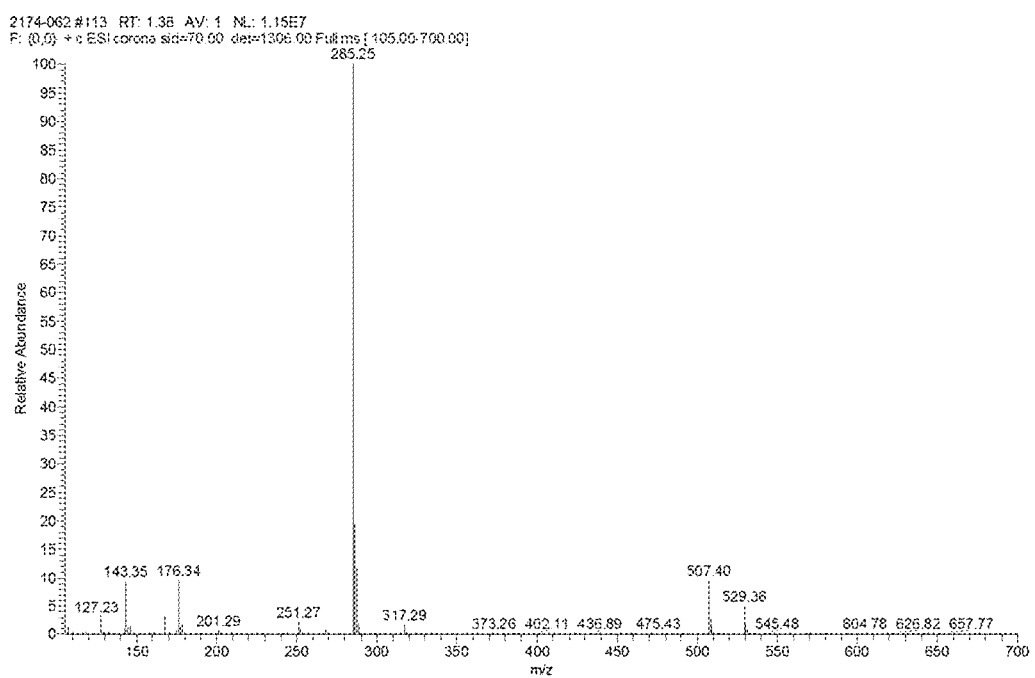
FIG. 36 displays the LCMS data for the final product of step 4 of the synthesis of compound B.
Figure 37:
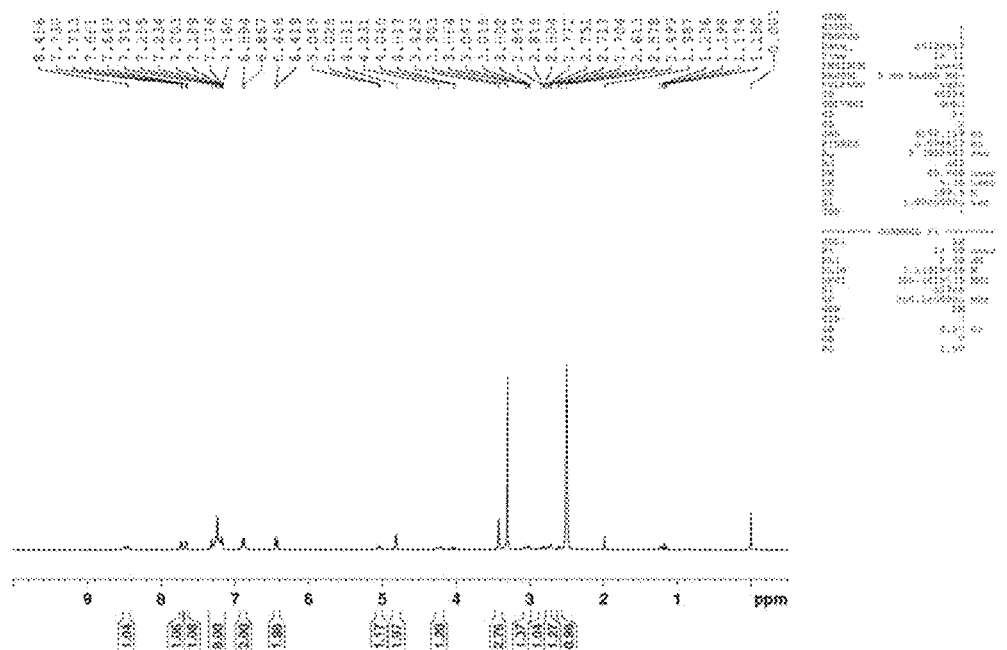
FIG. 37 displays the NMR data for the final product of step 4 of the synthesis of compound B.

The analytical data for compound 4 were as follows: HPLC: 98.3% (FIG. 35); LCMS (ESI+): m/z 507 (M+H) (FIG. 36); $^1$H-NMR (300 MHz, DMSO-d$_6$) δ 8.46 (d, J=8.5 Hz, 1H), 7.72 (d, J=4.1 Hz, 1H), 7.66 (d, J=3.63 Hz, 1H), 7.38-7.15 (m, 8H), 6.89 (d, J=8.3 Hz, 2H), 6.44 (d, J=8.3 Hz, 2H), 5.11-4.98 (m, 1H), 4.28-4.21 (m, 1H), 3.42 (s, 3H), 3.08-2.98 (m, 1H), 2.88-2.72 (m, 2H), 2.66-2.57 (m, 1H) (FIG. 37).

Step 5 of the reaction used to create compound B is detailed in the reaction scheme below. Compound 5 was synthesized using the same procedure for step 5 for the synthesis of compound A.

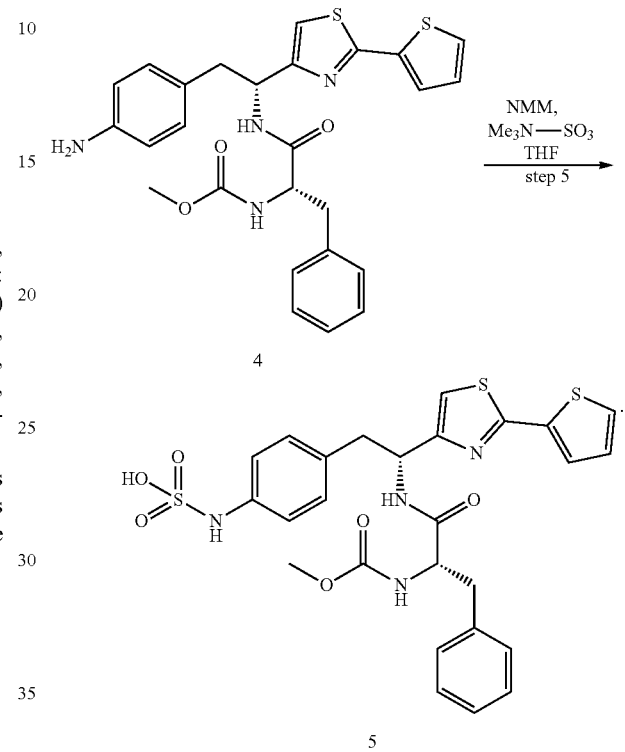

Figure 38:
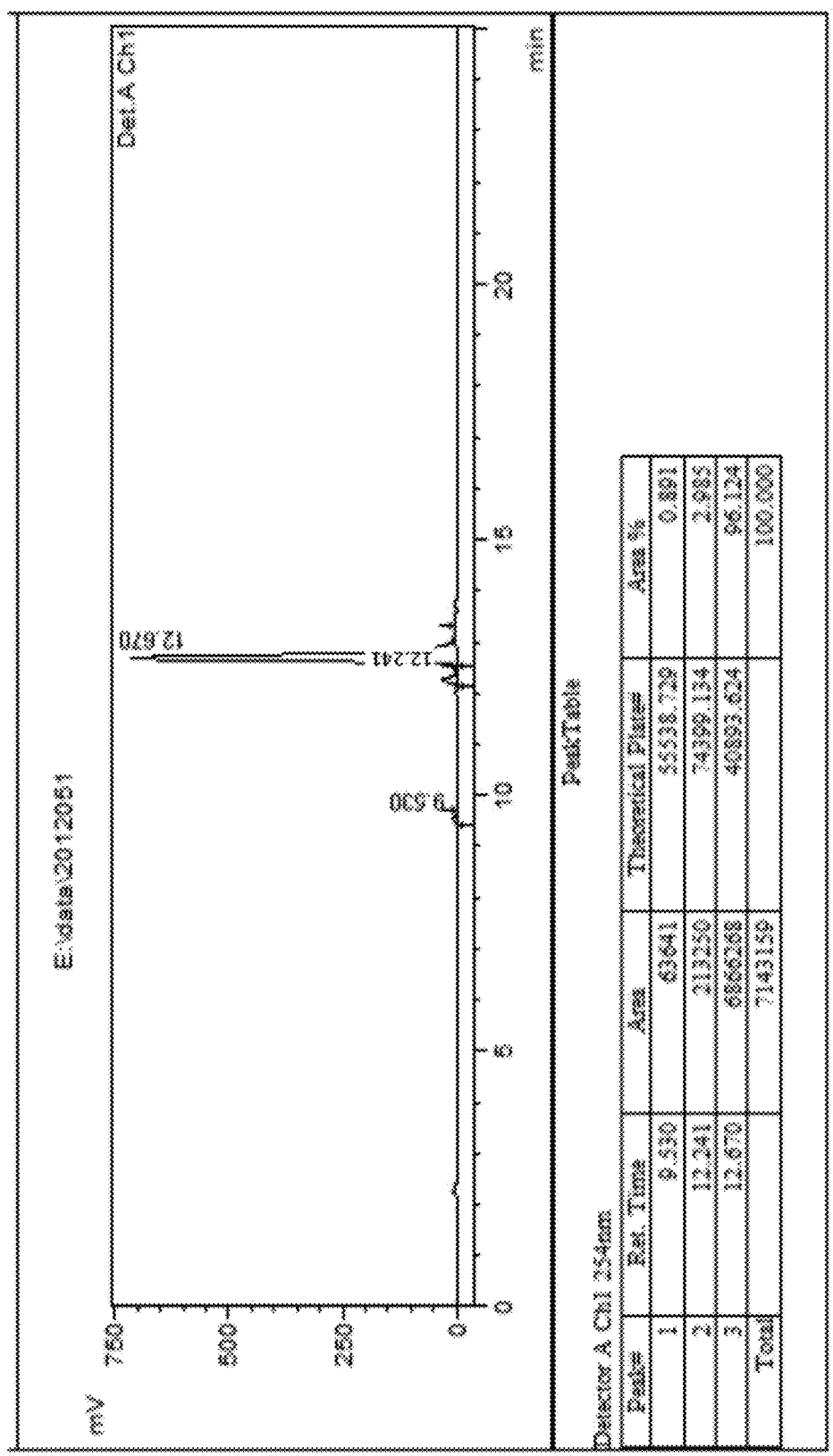
FIG. 38 displays the HPLC data for the final product of step 5 of the synthesis of compound B.
Figure 39:
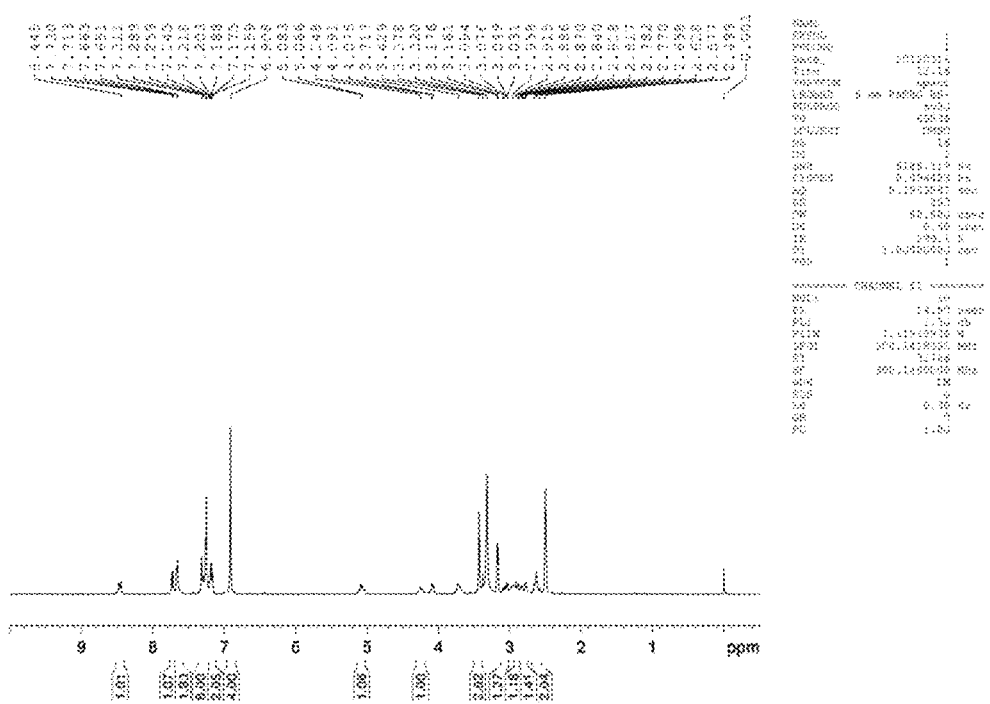
FIG. 39 displays the LCMS data for the final product of step 5 of the synthesis of compound B.
Figure 40:
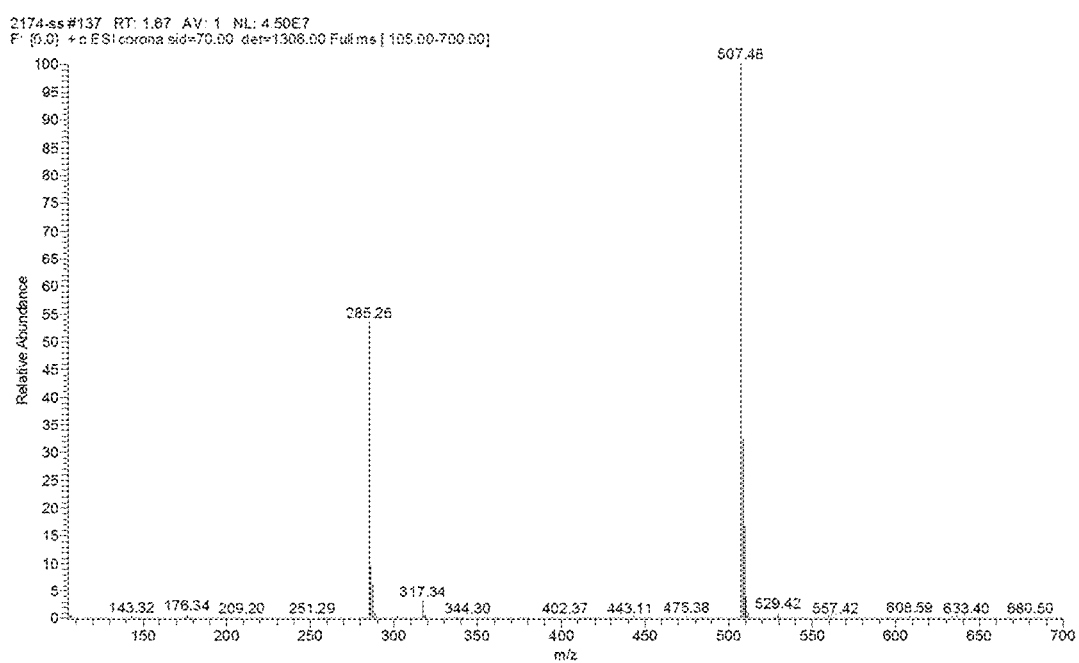
FIG. 40 displays the NMR data for the final product of step 5 of the synthesis of compound B.

The analytical data for compound 5, as shown above, were as follows: HPLC: 96.1% (FIG. 38); LCMS (ESI+): m/z 507 (M-S03+H) (FIG. 39); $^1$H-NMR (300 MHz, DMSO-d$_6$) δ 8.47 (d, J=8.5 Hz, 1H), 7.72 (d, J=4.9 Hz, 1H), 7.66 (d, J=3.5 Hz, 2H), 7.32-7.22 (m, 6H), 7.23-7.12 (m, 2H), 6.96 (s, 4H), 5.15-5.01 (m, 1H), 4.32-4.20 (m, 1H), 3.42 (s, 3H), 3.12-3.03 (m, 1H), 2.93-2.85 (m, 1H), 2.83-2.76 (m, 1H), 2.68-2.56 (m, 1H) (FIG. 40).

Step 6 of the pathway used to synthesize compound B is detailed in the reaction scheme below. Compound B was synthesized using the same procedure as described for compound A.

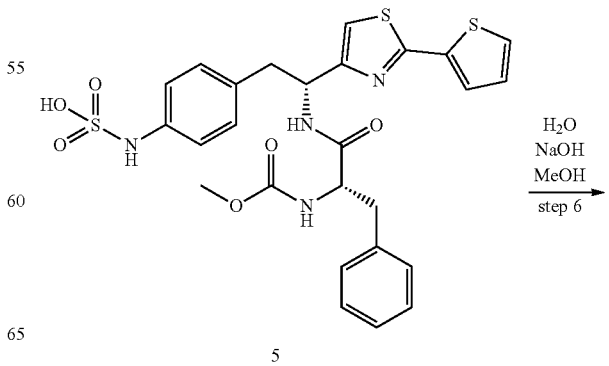

5

Figure 41:
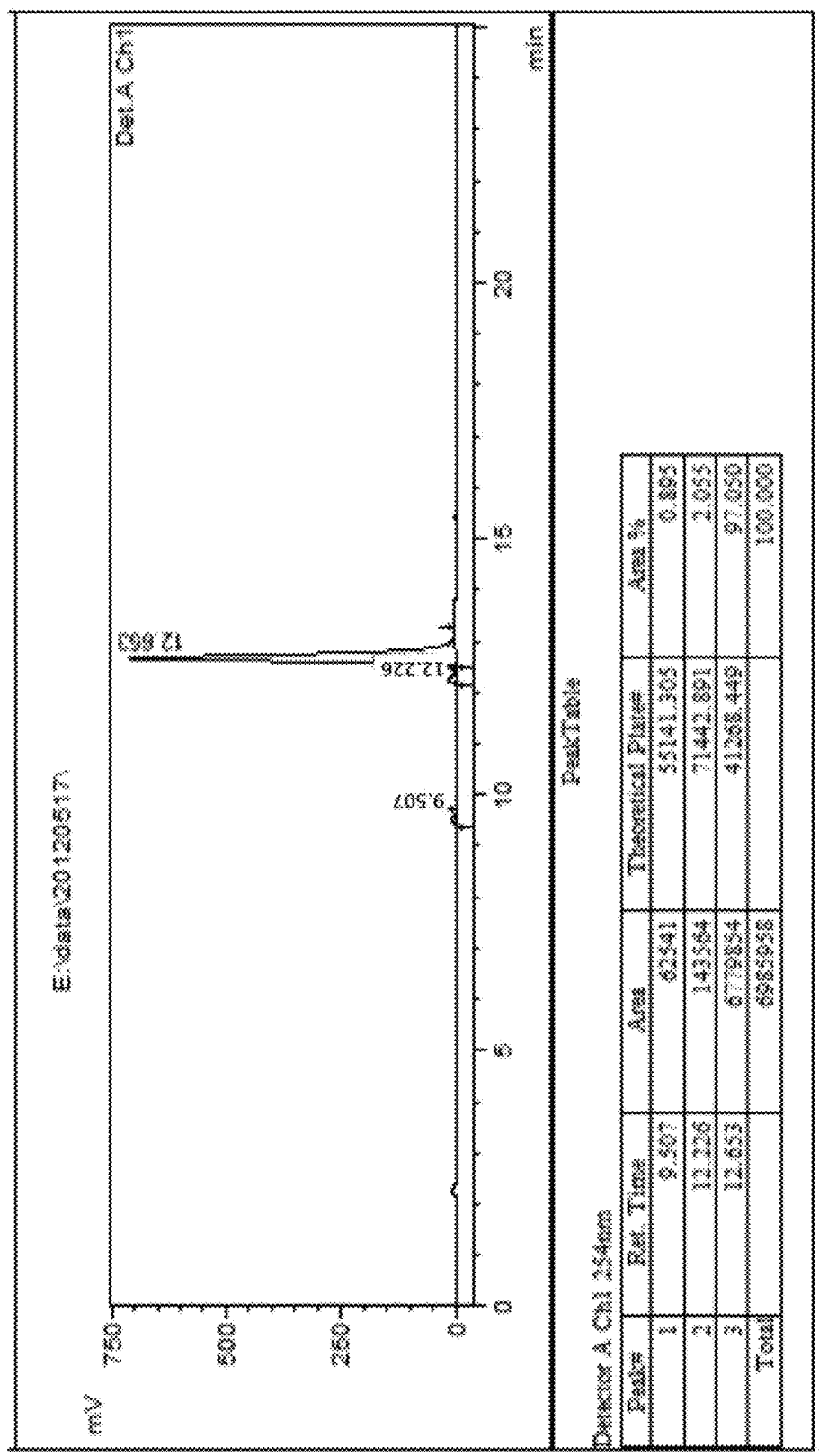
FIG. 41 displays the HPLC data for compound B.
Figure 42:
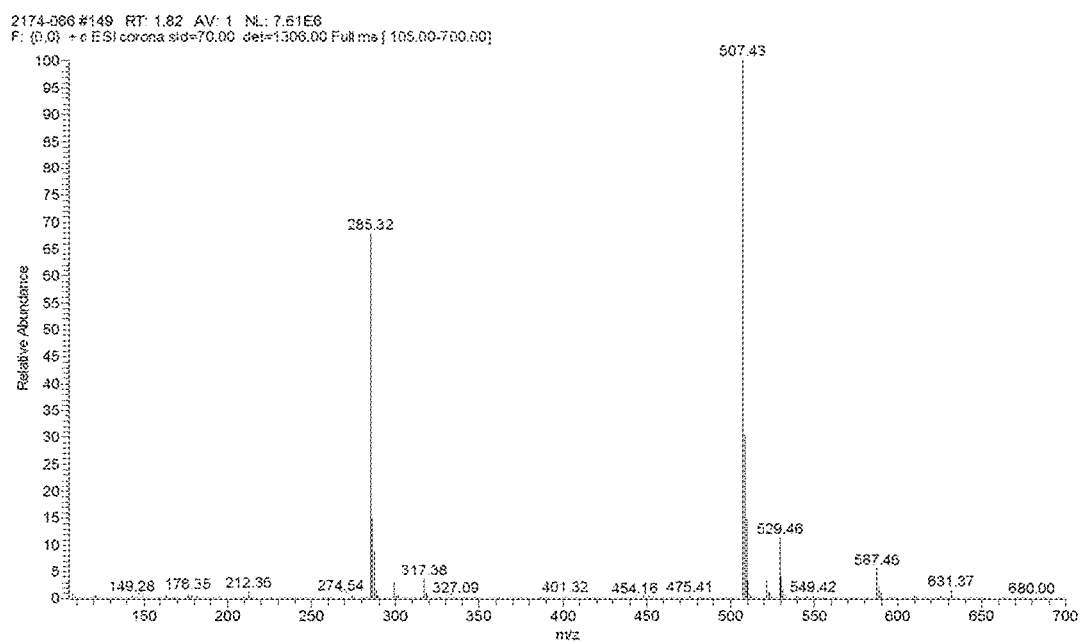
FIG. 42 displays the LCMS data for compound B.
Figure 43:
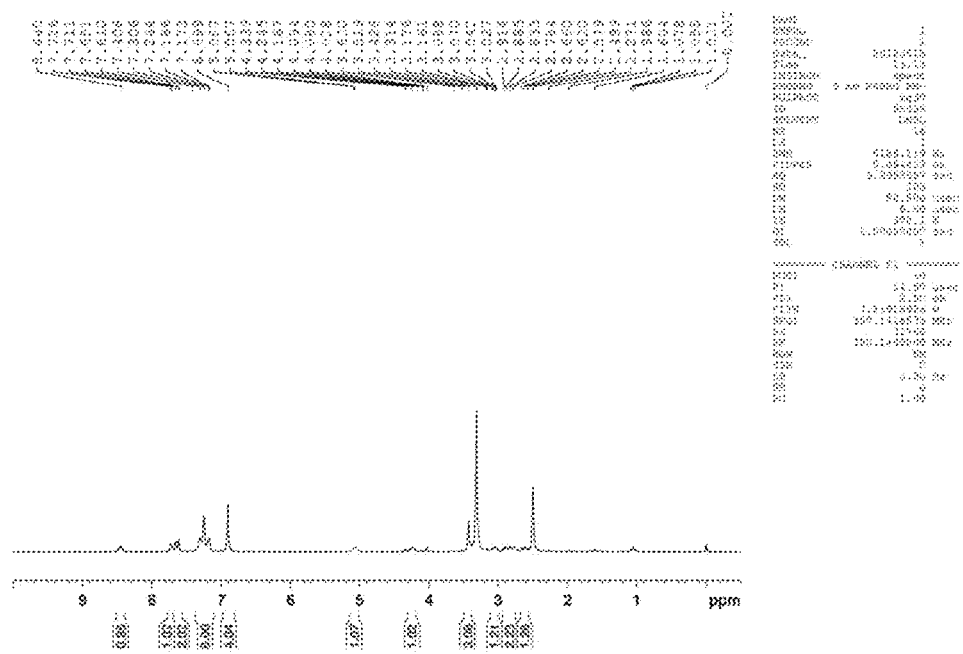
FIG. 43 displays the NMR data for compound B.

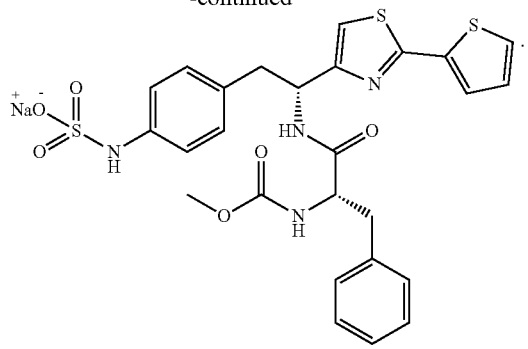
Compound B
The analytical data for compound B were as follows: HPLC: 97% (FIG. 41); LCMS (ESI+): m/z 587 (M-Na+2H) (FIG. 42); $^1$H-NMR (300 MHz, DMSO-$d_6$) δ 8.46 (d, J=8.1 Hz, 1H), 7.72 (d, J=4.4 Hz, 1H), 7.68-759 (m, 2H), 7.38-7.12 (m, 8H), 6.89 (s, 4H), 5.14-5.02 (m, 1H), 4.28-4.18 (m, 1H), 3.42 (s, 3H), 3.11-3.01 (m, 1H), 2.96-2.75 (m, 2H), 2.70-2.55 (m, 1H) (FIG. 43).
The complete reaction scheme for the synthesis of compound B is detailed below:
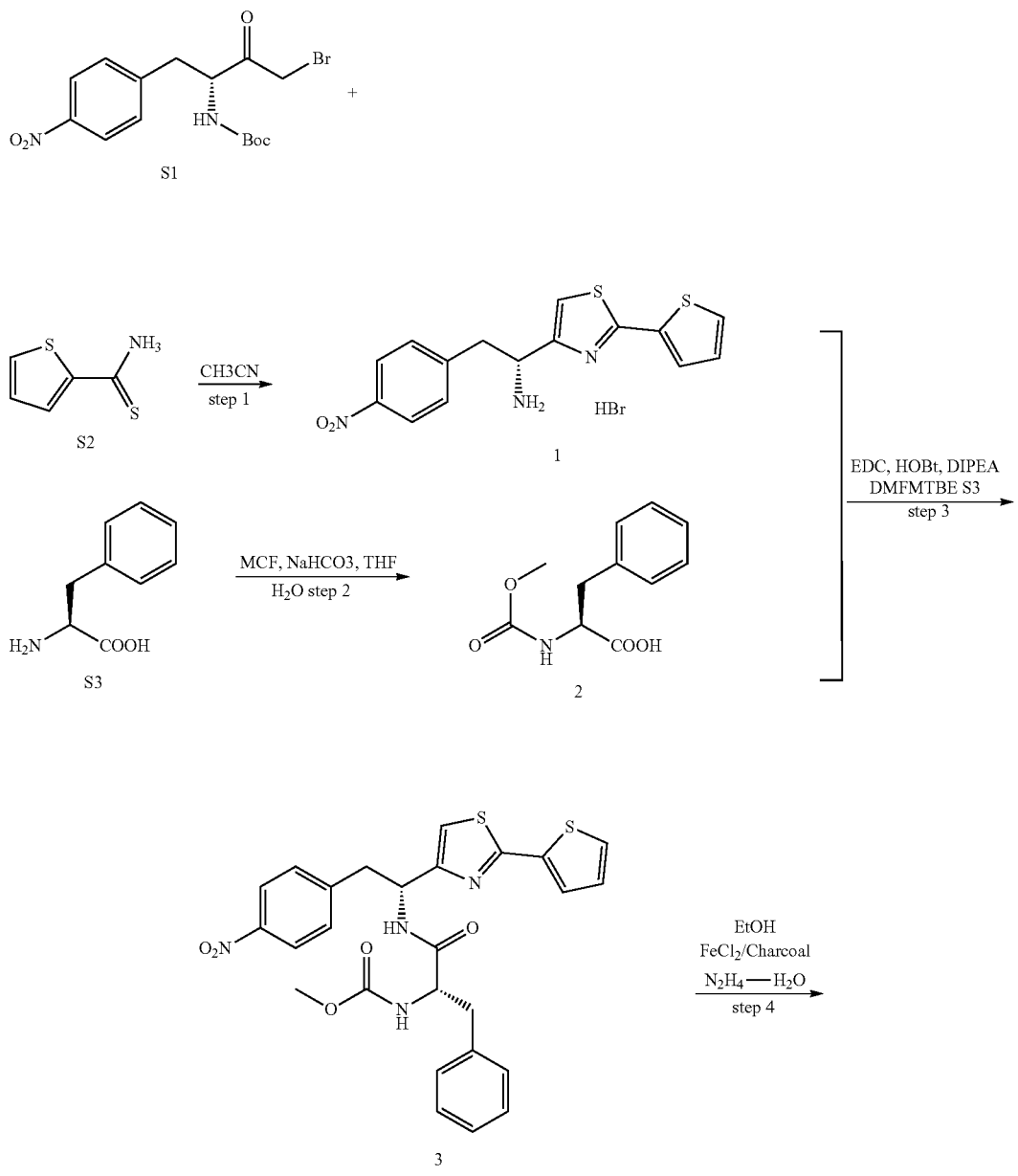

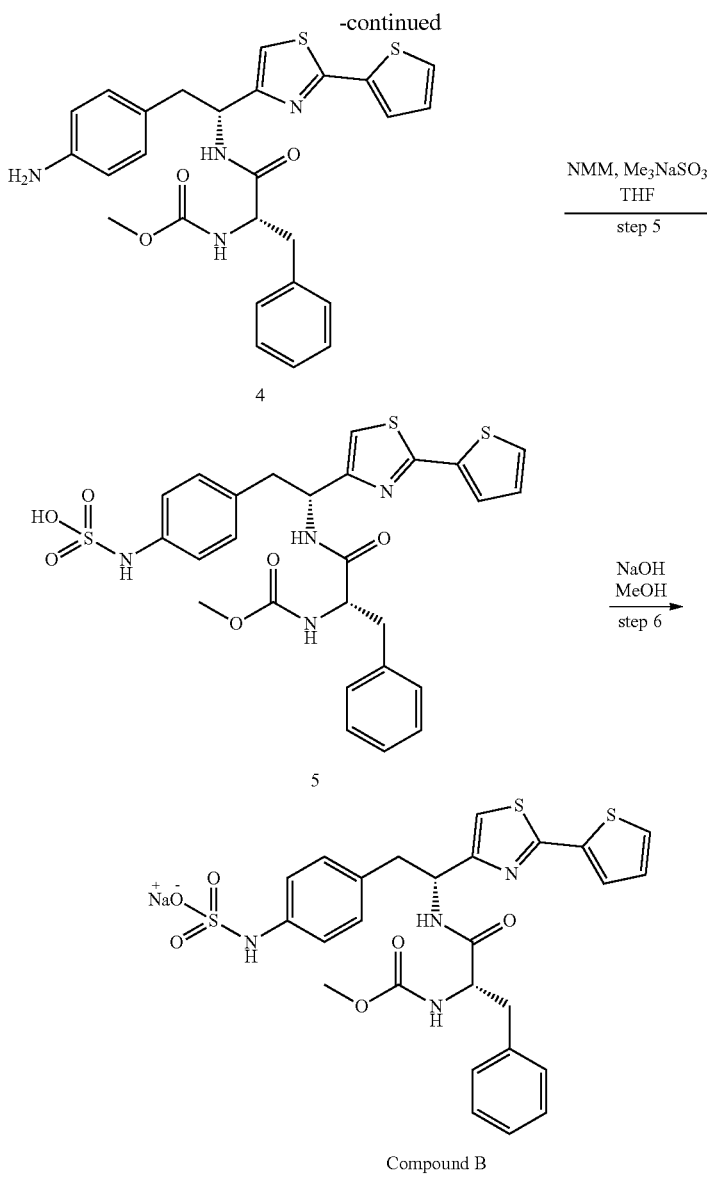

Compound B

Example 2: Tie2 Activation and Downstream Phosphorylation of Akt in Cultured Endothelial Cells A cell-based assay of compounds A-D is described herein.

Human umbilical vein endothelial cells (HUVECs) were isolated freshly from human placenta, grown in endothelial growth medium, and used before passage 6. To evaluate the effects of the compounds on phosphorylation of Tie2 and downstream signaling molecules, cells were serum-starved in endothelial basal medium without added growth factors for 3 hours before stimulation. Cells were treated for 10 minutes with vehicle (DMSO), or compounds A, B, C, or D in DMSO. Cells were lysed in RIPA buffer (150 mM NaCl, 1% IGEPAL CA-630, 0.05% sodium deoxycholate, 0.1% SDS, 20 mM Tris-HCl at pH 7.6, 1 mM EDTA, 1 mM NaF, 1 mM sodium orthovanadate, 5 mM benzamidine) plus complete protease inhibitor cocktail tablets. Tie2 was then immunoprecipitated from cell lysates with a mouse monoclonal antibody (clone 33) and probed sequentially with mouse monoclonal anti-phosphotyrosine (clone 4G10) and anti-Tie2 (clone 33). Whole cell lysates were used to quantify phospho-AKT with the PathScan Phospho-Akt1 (Ser473) Sandwich ELISA Kit according to the manufacturer's instructions. Relative AKT phosphorylation in each experiment was quantified by $OD_{450}$.

Figure 44:
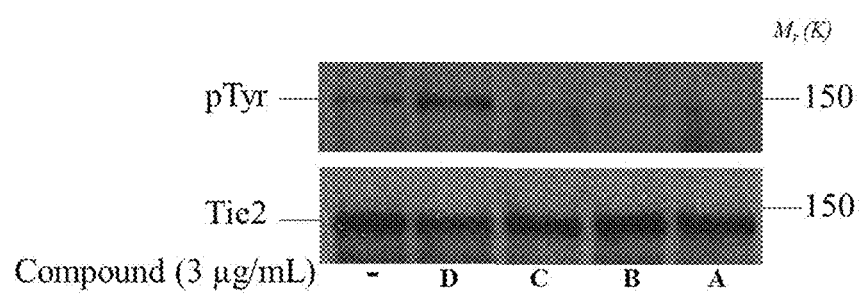
FIG. 44 is a western blot representing Tie2 phosphorylation.

FIG. 44 is a western blot of Tie2 immunoprecipitated from endothelial cells treated with DMSO control or the indicated compounds (D, C, B, or A), and then sequentially probed with an anti-Tie2 antibody to detect total Tie2 (lower blot) and an anti-phosphotyrosine antibody to detect phosphorylated Tie2 (upper blot). The blot shows that Tie2 was immunoprecipitated at relatively equal amounts, whereas Tie2 phosphorylation differed between the treatment conditions. Treatment with compound D resulted in a substantial increase in Tie2 phosphorylation compared to the DMSO control. An increase in Tie2 phosphorylation compared to the DMSO control was not detected for compounds A, B, and C.

Figure 45:
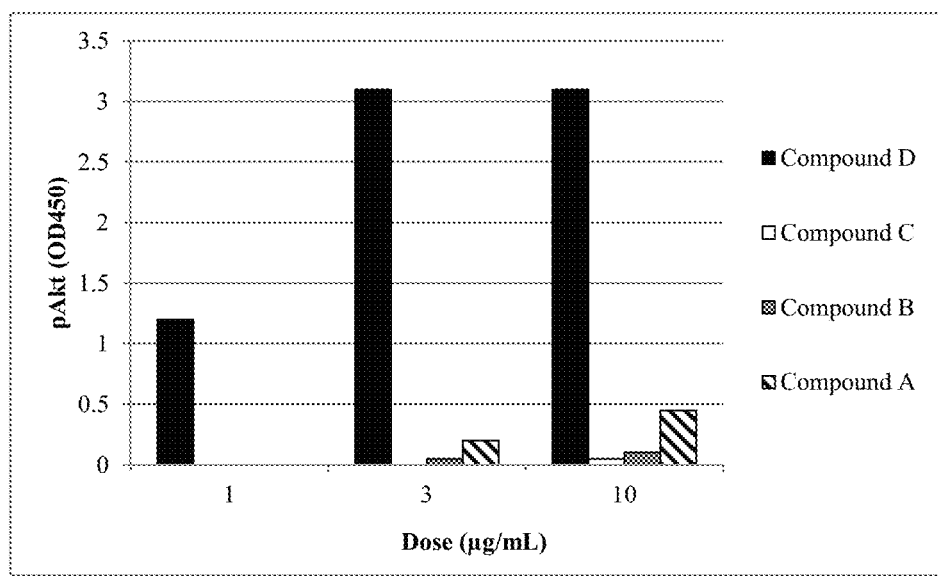
FIG. 45 represents ELISA data for Akt phosphorylation.

FIG. 45 represents data from an ELISA to determine Akt phosphorylation, a measure of Tie2 activation. Consistent with FIG. 44, compound D had the strongest effect on Tie2 activation, as determined by the high levels ($OD_{450}$=1.2) of relative Akt phosphorylation even at the lowest dose of compound D (1 μg/mL). Akt phosphorylation significantly increased ($OD_{450}$=3.1) using compound D at 3 μg/mL reaching a maximum of Akt phosphorylation, which did not increase further at the highest dose of compound D (10 μg/mL). Compound A had a moderate effect on Akt phosphorylation and began to show effects at 3 μg/mL, where Akt phosphorylation slightly increased ($OD_{450}$=0.2). Akt phosphorylation further increased ($OD_{450}$=0.45) when 10 μg/mL of compound A was used. Compounds B and C had similar effects on Akt phosphorylation, moderately increasing Akt phosphorylation ($OD_{450}$ around 0.2) most significantly when used at 10 μg/mL.

Example 3: Formulation of Compound with HPβCD

Compositions of any of compounds A, B, C, and D are prepared by diluting about 100 mg of a sterile powder of a compound in 100 mL water to form a first composition. To the first composition is added 250 mg of hydroxypropyl beta cyclodextrin (HPβCD). Example compositions are shown in TABLE I.

TABLE I

| Compound (mg) | HPβCD (mg) | Water (mL) |
| --- | --- | --- |
| 50 | 250 | 25 |
| 50 | 250 | 50 |
| 50 | 250 | 75 |
| 50 | 250 | 100 |
| 100 | 250 | 25 |
| 100 | 250 | 50 |
| 100 | 250 | 75 |
| 100 | 250 | 100 |
| 50 | 250 | 200 |
| 50 | 250 | 300 |
| 50 | 250 | 400 |
| 50 | 250 | 500 |
| 100 | 250 | 200 |
| 100 | 250 | 300 |
| 100 | 250 | 400 |
| 100 | 250 | 500 |

Example 4: Formulation of Compound with HPβCD

To a 100 mL volumetric flask containing water (85 mL) were charged HPβCD (10 g) and dextrose (1.5 g). The solution was stirred for 1 hour at 20° C., then the volume made up to 100 mL with additional distilled water. The resulting solution was 10% HPβCD and 1.5% dextrose.

In a similar manner, solutions comprising 15% HPβCD/1.5% dextrose and 17.5% HPβCD/1.5% dextrose were prepared. These stock solutions were used for the following experiments.

In a 25 mL volumetric flask was added the stock solution comprising 10% HPβCD/1.5% dextrose followed by the addition of the sodium salt of compound D (550 mg). The total volume was made up to 25 mL by the addition of distilled water. The resulting solution had a nominal concentration of compound D of 20 mg/mL after applying a molecular weight correction factor.

Similarly, to a stock solution comprising 10% HPβCD/1.5% dextrose was added compound D (687 mg). After dilution to 25 mL the resulting solution had a nominal concentration of compound D of 25 mg/mL after applying a molecular weight correction factor.

Compositions comprising 15% HPβCD/1.5% dextrose and 687 mg and 825 mg of compound D were also prepared. Likewise, compositions comprising 17.5% HPβCD/1.5% dextrose and 825 mg and 962.5 mg of the sodium salt of compound D were also prepared.

TABLE II describes the test compositions, each totaling 25 mL.

TABLE II

| | Stock Solution | | | | | |
| --- | --- | --- | --- | --- | --- | --- |
| | 10% HPβCD/1.5% dex. | | 15% HPβCD/1.5% dex. | | 17.5% HPβCD/1.5% dex. | |
| Comp D-Na (mg) | 550 | 687 | 687 | 825 | 825 | 962.5 |
| Comp D mg/mL | 20 | 25 | 25 | 30 | 30 | 35 |

To 3 one-dram vials was transferred approximately 3 mL of each of the 6 solutions above. One vial of each solution was held at 4° C., 20° C. and 40° C. The vials were evaluated weekly for one month then monthly for three months.

After 3 months none of the vials appeared hazy or had any precipitate or flocculent. The above compositions where then further processed and submitted for in vivo testing.

Example 5: Preparation of Compositions for Subcutaneous Delivery Via 0.75 mL Single Use Syringes 200 mL of deionized water is added to 2-hydroxypropyl-β-cyclodextrin (50 g) with stirring. Next, dextrose (96%) (1.3 g) is added, and the solution is stirred until all the solids are dissolved. A formulation containing one of the compounds disclosed herein or a mixture thereof is added, and the solution is stirred until the solids are dissolved. The resulting solution has a pH value of 7.26 and a density of 1.07 g/mL. The final solution is filtered through a 20-0.22 micron PVDF filter. A calibrated peristaltic pump is used to dispense 0.75 mL of the final solution into 0.75 mL syringes having 27 g staked needles and stoppers.

Example 6: Preparation of Compositions for Subcutaneous Delivery Via 0.75 mL Single Use Syringes 200 mL of deionized water is added to 2-hydroxypropyl-β-cyclodextrin (43.75 g) with stirring. Next, dextrose (96%) (2.61 g) is added and the solution is stirred until all the solids are dissolved. A formulation containing one of the compounds disclosed herein or a mixture thereof is added, and the solution is stirred until the solids are dissolved. The resulting solution has a pH value of 7.32, which is adjusted to 7.04 with 1N HCl (0.5 mL). The final solution is filtered through a 20-0.22 micron PVDF filter. A calibrated peristaltic pump is used to dispense 0.75 mL of the final solution into 0.75 mL syringes having 27 g staked needles and stoppers.

Example 7: Preparation of Compositions for Subcutaneous Delivery Via 0.75 mL Single Use Syringes 200 mL of deionized water is added to 2-hydroxypropyl-β-cyclodextrin (56.25 g) with stirring. Next, dextrose (96%) (1.3 g) is added and the solution is stirred until all the solids are dissolved. A formulation containing one of the compounds disclosed herein or a mixture thereof is added, and the solution is stirred until the solids are dissolved. The final solution is filtered through a 20-0.22 micron PVDF filter. A calibrated peristaltic pump is used to dispense 0.75 mL of the final solution into 0.75 mL syringes having 27 g staked needles and stoppers.

Example 8: Step-Wise Manufacturing Process: 20 mg of Compound D Per mL Solution

1. Add approximately 16.0 kg of United States Pharmacopeia (USP) Sterile Water for Injection to an appropriately-sized glass vessel.
2. Add 2812.5 g of 2-hydroxylpropyl-beta-cyclodextrin (HPβCD) (USP) to the glass flask and mix for a minimum of 5 minutes or until dissolved.
3. Add 450 g of compound D, as the sodium salt, factored for purity, minor stereoisomers, volatiles and water, to the glass flask and mix for a minimum of 30 minutes or until all of the solids are dissolved.
4. Add 450 g of D-glucose (Dextrose) Anhydrous (USP) to the glass flask and mix for a minimum of 5 minutes or until all of the solids are dissolved.
5. Transfer the solution to a 36 L glass formulation vessel using a peristaltic pump.
6. QS the formulation to 22.7 kg by adding Sterile Water for Injection, USP and mix for a minimum of 30 minutes or until dissolved.
7. Adjust the pH to obtain a pH of 6.6-7.0.
8. Add sufficient quantities of Sterile Water for Injection, USP to the batch to obtain the final batch weight of 23.7 kg (22.5 L*1.052 g/mL-specific gravity) and mix for a minimum of 10 minutes or until all of the solids are dissolved.
9. Filter through two filters connected in series into a similar 36 L glass fill vessel.
10. Fill into various syringes: i.e., 0.75 mL syringe.

Example 9: Baseline Study for Determining the Effectiveness of the Disclosed Methods for Treating Ocular Diseases Described herein is a study of four human subjects with visual acuity loss due to diabetic macular edema (central retinal thickness [CRT] of more than 325 microns and best corrected visual acuity less than 70 letters) that were treated with subcutaneous injections of 5 mg of 4-{(S)-2-[(S)-2-methoxycarbonyl-amino]-3-phenylpropanamido]-2-[2-(thiophen-2-yl)thiazol-4-yl]ethyl}phenylsulfamic acid twice a day for 28 days. Improvement of visual acuity in these subjects was observed for a period of two months (days 28 through 84). At any time during the course of the study, investigators could administer additional therapy of intravitreal injection of an anti-VEGF agent, for example, ranibizumab, bevacizumab, and/or aflibercept, if considered by the investigator to be medically necessary. Retinal thickness as measured by ocular coherence tomography and best-corrected visual acuity as measured by a standard vision test (ETDRS) were assessed at regular intervals during the 28 day active treatment phase and through the 2 month post-treatment observation phase, (Screening, Day 1 [baseline], Day 7, Day 14, Day 21, Day 28, Day 42, Day 56 and Day 84). The main efficacy outcomes for the study were change in CRT and visual acuity over time with treatment.

Figure 46:
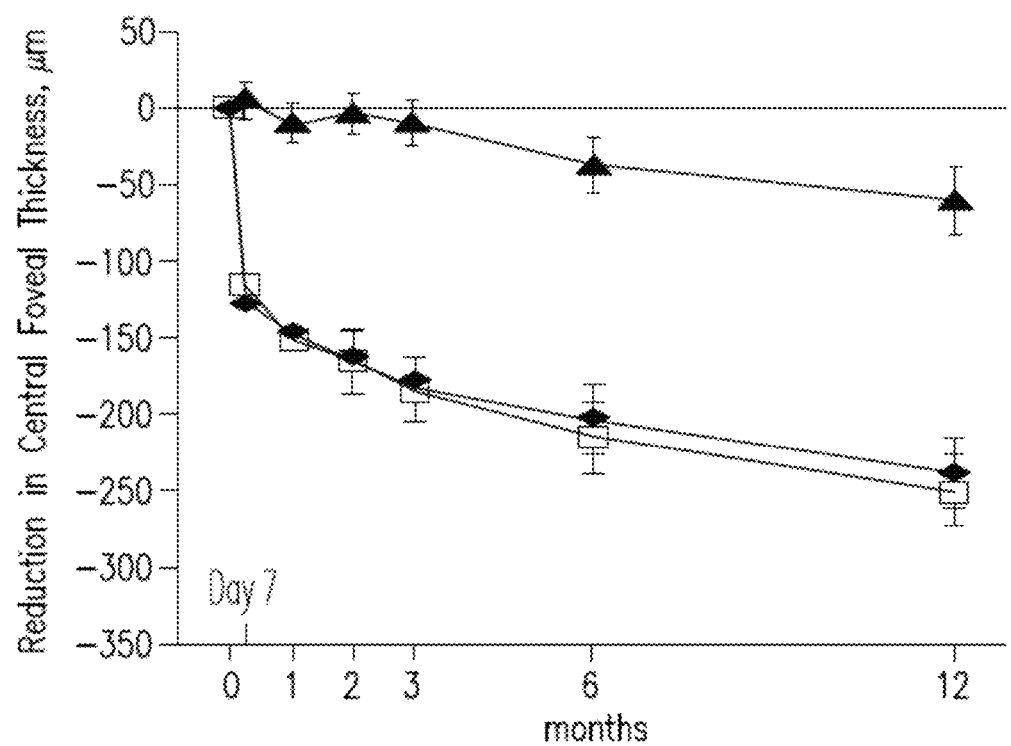
FIG. 46 depicts the results of two Phase III studies to determine the effect of intravitreal injections of ranibizumab in patients with diabetic macular edema.

FIG. 46 depicts the results of two phase three studies to determine the effect of intravitreal injections of ranibizumab in patients with diabetic macular edema. In this study, patients received intravitreal injections with either 0.3 mg (♦) or 0.5 mg (■) ranibizumab monthly, whereas the control group (▲) received placebo. As depicted in FIG. 46 the reduction in Central Foveal Thickness (CFT) for both the 0.3 mg and 0.5 mg cohorts were essentially identical. As shown in FIG. 46, the two groups receiving ranibizumab had a reduction in Central Foveal Thickness of approximately 120 to 160 μm from day 7 to 1 month after the first injection of ranibizumab.

Figure 47:
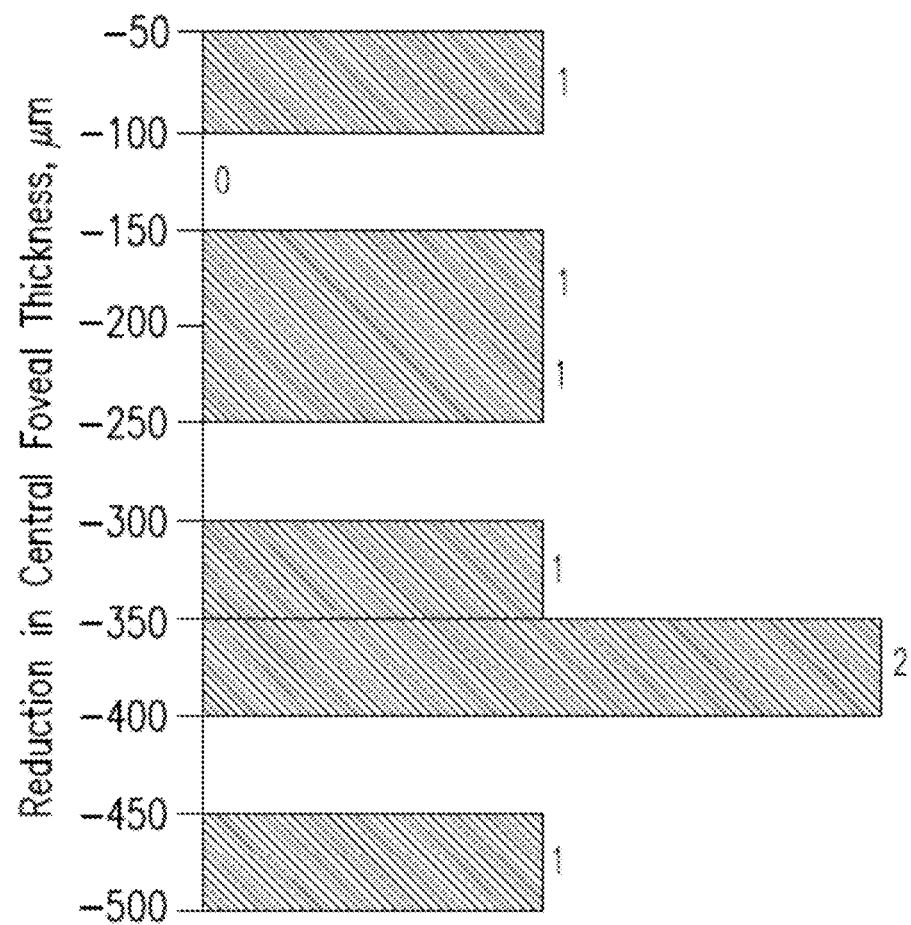
FIG. 47 depicts the results of a study wherein 4 patients received 5 mg of Compound A subcutaneously twice daily for 28 days and subsequently were treated in one or both eyes (7 eyes total) with either ranibizumab (0.3 or 0.5 mg)

FIG. 47 depicts the results of a study wherein 4 patients received 5 mg of 4-{(S)-2-[(S)-2-methoxycarbonylamino]-3-phenylpropanamido]-2-[2-(thiophen-2-yl)thiazol-4-yl]ethyl}phenylsulfamic acid subcutaneously twice daily for 28 days and subsequently were treated in one or both eyes (7 eyes total) with either ranibizumab (0.3 or 0.5 mg) or aflibercept (2 mg) by intravitreal injection at the discretion of the study investigator.

FIG. 47 is read as follows. At 14-28 days post ranibizumab or aflibercept, 1 patient eye had a Central Foveal Reduction of between 50-100 μm. 1 patient eye had a Central Foveal Reduction of between 150-200 μm. 1 patient eye had a Central Foveal Reduction of between 200-250 μm. 1 patient eye had a Central Foveal Reduction of between 300-350 μm. 2 patient eyes had a Central Foveal Reduction of between 350-400 μm. 1 patient eye had a Central Foveal Reduction of between 450-500 μm. The mean change in Central Foveal Thickness was −289 μm, approximately double the reduction seen after ranibizumab injection in the study in FIG. 46.

FIG. 48 depicts the results of two phase three studies performed to determine the effect of intravitreal injections of ranibizumab in patients with diabetic macular edema. Results of these studies were used to determine the effectiveness of the disclosed methods for treating ocular diseases. The control group is represented by (♦). Patients receiving 0.5 mg of ranibizumab monthly via ocular injection are represented by (■). As shown in FIG. 48, the group receiving ranibizumab had an increase in visual acuity of approximately 4 to 6 letters from day 7 to 1 month after the first injection of ranibizumab.

FIG. 49 depicts the increased visual acuity of a study wherein 4 patients received 5 mg of 4-{(S)-2-[(S)-2-methoxycarbonylamino]-3-phenylpropanamido]-2-[2-(thiophen-2-yl)thiazol-4-yl]ethyl}phenylsulfamic acid subcutaneously twice daily for 28 days, and subsequently were treated with either ranibizumab (0.3 or 0.5 mg) or aflibercept (2 mg) by intravitreal injection at the discretion of the study investigator. FIG. 49 is read as follows. At 14-28 days post ranibizumab or aflibercept, 1 patient eye had an increase of from 16 to 18 letters improvement. 2 patient eyes had an increase of from 14 to 16 letters improvement. 1 patient eye had an increase of from 10 to 12 letters improvement. 1 patient eye had an increase of from 6 to 8 letters improvement. 1 patient eye had an increase of from 2 to 4 letters improvement. 1 patient eye had a decrease of from 2 to 4 letters. The mean change in Visual Acuity was 9 letters, approximately 3 to 5 letters more improvement than seen in the benchmark study of ranibizumab alone depicted in FIG. 48.

FIG. 50 represents the results of a single patient. The eye having the greater Central Foveal Thickness (CFT) was chosen as the study eye. From day 1, the patient was given 5 mg of 4-{(S)-2-[(S)-2-methoxycarbonylamino]-3-phenyl-propanamido]-2-[2-(thiophen-2-yl)thiazol-4-yl]ethyl}phenylsulfamic acid subcutaneously twice daily. At week 3 (21 days, indicated by arrow) the fellow eye was treated with 0.5 mg of ranibizumab by injection. At week 6 (42 days, indicated by arrow) the study eye was treated with 0.5 mg of ranibizumab.

The CFT of the fellow eye fell significantly (350 μm) by week 4 (28 days). As a result, a pronounced reduction in CFT was observed in the study eye from day 21 to day 28 (approximately 250 μm). By the next monitoring point, week 6, the effects of the systemically-received ranibizumab were no longer present and the CFT returned to approximately 775 μm. At week 6, the study eye was treated with an intravitreal injection of 0.5 mg of ranibizumab. By week 8, an overall reduction in CFT of approximately 500 μm was observed, and the CFT of the subject eye was approximately 225 μm. Compared to the study depicted in FIG. 46, wherein the average change in CFT at one month after ranibizumab injection was approximately 160 mm, the combination method provided substantially-greater reductions at 2-4 weeks following ranibizumab injection.

FIG. 51 represents the results of a single patient. The eye having the greater CFT was chosen as the Study Eye. The patient from day one was given 5 mg of 4-{(S)-2-[(S)-2-methoxycarbonylamino]-3-phenylpropanamido]-2-[2-(thiophen-2-yl)thiazol-4-yl]ethyl}phenylsulfamic acid subcutaneously twice daily. At week 4 (28 days, indicated by arrow) the fellow eye was rescued with 2 mg of aflibercept. After rescue, the fellow eye had a CFT reduction of approximately 400 μm. At week 6 (42 days, indicated by arrow) the study eye was rescued with 2 mg of aflibercept. After rescue, the study eye had a CFT reduction of approximately 300 μm. Unlike the results depicted for the ranibizumab protocol, no effects of the systemically-delivered aflibercept were observed in the fellow eye. From onset of the study, a reduction was observed of CFT in the study eye and the fellow eye of approximately 300 μm and 280 μm, respectively.

FIG. 52 graphically represents the results of a choroidal neovascularization murine test involving an active control, aflibercept (Eylea™), 4-{(S)-2-[(S)-2-methoxycarbonylamino]-3-phenylpropanamido]-2-[2-(thiophen-2-yl)thiazol-4-yl]ethyl}phenylsulfamic acid, and a combination of aflibercept and 4-{(S)-2-[(S)-2-methoxycarbonylamino]-3-phenylpropanamido]-2-[2-(thiophen-2-yl)thiazol-4-yl]ethyl}phenylsulfamic acid. Rupture of Burch's membrane in three locations of the eye was induced by laser. Control animals were given intraocular injections of phosphate buffered saline (PBS). Animals treated with aflibercept received one intraocular 40 μg dose of the drug on the day of laser treatment. The mice were then treated with either 4-{[(S)-2-[(S)-2-methoxycarbonylamino]-3-phenylpropanamido]-2-[2-(thiophen-2-yl)thiazol-4-yl]ethyl}phenylsulfamic acid at 20 mg/kg by subcutaneous injection twice daily, or PBS injection twice daily. This protocol yielded four groups of mice: a negative control group treated with intraocular and subcutaneous PBS, a monotherapy group treated with intraocular aflibercept and subcutaneous PBS; a monotherapy group treated with intraocular PBS and subcutaneous injections of 4-{(S)-2-[(S)-2-methoxycarbonylamino]-3-phenylpropanamido]-2-[2-(thiophen-2-yl)thiazol-4-yl]ethyl}phenylsulfamic acid; and a combination therapy group receiving one intraocular injection of 40 μg of the drug on the day of laser treatment and 20 mg/kg subcutaneous injections twice daily.

FIGS. 53A-D depict the flat mounts of excised choroidal tissue stained with FITC-labeled *Griffonia simplicifolia* (GSA). The extent of choroidal neovasculature is evident in the control sample, FIG. 53A. FIG. 53B represents the extent of neovascularization in the choroidal tissue of animals treated with aflibercept. FIG. 53C represents animals treated with 4-{(S)-2-[(S)-2-methoxycarbonylamino]-3-phenylpropanamido]-2-[2-(thiophen-2-yl)thiazol-4-yl]ethyl}phenylsulfamic acid. FIG. 53D represents the extent of neovascularization present in animals having a combined therapy of aflibercept and 4-{(S)-2-[(S)-2-methoxycarbonylamino]-3-phenylpropanamido]-2-[2-(thiophen-2-yl)thiazol-4-yl]ethyl}phenylsulfamic acid.

Example 10: Solubility of Compounds of the Disclosure

The room temperature aqueous solubility (mg/mL) of the compound (4-{(S)-2-[(S)-2-methoxycarbonylamino]-3-phenylpropanamido]-2-[2-(thiophen-2-yl)thiazol-4-yl]ethyl}phenylsulfamic acid) in water, HPβCD, Poloxamer 407, and sulfobutylether-β-cyclodextrin, is provided in TABLE III. Solubility in saline for the test compound is reduced presumably due to the common ion effect. All the solubilizing agents tested provided good improvements in aqueous solubility of the test compound.

TABLE III

|  | Solubility |
|---|---|
| % HPβCD |  |
| 0 | 27 |
| 10 | 45 |
| 20 | 57 |
| 30 | 72 |
| % SBE-β-CD |  |
| 15 | 44 |
| % Poloxamer 407 |  |
| 20 | 44 |

The solubility (mg/mL) of the test compound in mixtures of HβCD and PEG400 is illustrated in TABLE IV. Use of either HPβCD or PEG400 individually provided an increase in solubility. However, addition of PEG400 to a mixture of the test compound and HPβCD caused an erosion of solubility, with solubility being inversely proportional to the amount of PEG400.

TABLE IV

| % HPβCD | % PEG400 | Solubility (mg/mL) |
|---|---|---|
| 0 | 15 | 30 |
| 0 | 30 | 68 |
| 15 | 0 | 59 |
| 15 | 5 | 57 |
| 15 | 10 | 34 |
| 15 | 15 | 6 |

TABLE V contains aqueous solution formulations of the test compound above with the denoted solvents that have been prepared and shown to be chemically stable through 1 month at 50° C., and physically stable at 5° C., at ambient temperature at 50° C. The formulations are more stable at pH values above pH 4. The target pH range for the formulations is pH 7+/−0.5 pH units.

TABLE V

| Formulation | Concentration of test compound |
|---|---|
| 10% HPβCD | 15 mg/mL |
| 25% HPβCD | 50 mg/mL |

TABLE V-continued

| Formulation | Concentration of test compound |
|---|---|
| 30% HPβCD | 50 mg/mL |
| 15% HPβCD/0.25% saline | 40 mg/mL[a] |
| 4.5% mannitol | 5 mg/mL[b] |

[a]Evaluated for short-term physical stability at 5° C. and ambient temperature.
[b]Physically and chemically stable through one week at room temperature and one week at 50° C.

EMBODIMENTS

The following are illustrative embodiments.

Embodiment 1

A compound of formula:

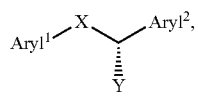

wherein: Aryl¹ is an aryl group which is substituted or unsubstituted; Aryl² is an aryl group which is substituted or unsubstituted; X is alkylene, alkenylene, alkynylene, an ether linkage, an amine linkage, an amide linkage, an ester linkage, a thioether linkage, a carbamate linkage, a carbonate linkage, a ureido linkage, a sulfone linkage, any of which is substituted or unsubstituted, or a chemical bond; and Y is H, aryl, heteroaryl, NH(aryl), NH(heteroaryl), NHSO₂R$^g$, or NHCOR$^g$, any of which is substituted or unsubstituted, or

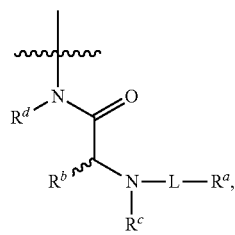

wherein: L is alkylene, alkenylene, or alkynylene, any of which is substituted or unsubstituted, or together with the nitrogen atom to which L is bound forms an amide linkage, a carbamate linkage, a ureido linkage, or a sulfonamide linkage, or a chemical bond, or together with any of R$^a$, R$^b$, R$^c$, and R$^d$ forms a ring that is substituted or unsubstituted; R$^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, R$^b$, R$^c$, and R$^d$ forms a ring that is substituted or unsubstituted; R$^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, R$^a$, R$^c$, and R$^d$ forms a ring that is substituted or unsubstituted; R$^c$ is H or alkyl which is substituted or unsubstituted, or together with any of L, R$^a$, R$^b$, and R$^d$ forms a ring that is substituted or unsubstituted; R$^d$ is H or alkyl which is substituted or unsubstituted, or together with any of L, R$^a$, R$^b$, and R$^c$ forms a ring that is substituted or unsubstituted; and R$^g$ is H, alkyl, alkenyl, alkynyl, aryl, arylalkyl, heterocyclyl, heterocyclylalkyl, heteroaryl, or heteroarylalkyl, any of which is substituted or unsubstituted, or a pharmaceutically-acceptable salt, tautomer, or zwitterion thereof.

Embodiment 2

The compound of embodiment 1, wherein: Aryl¹ is substituted or unsubstituted phenyl; Aryl² is substituted or unsubstituted heteroaryl; and X is alkylene.

Embodiment 3

The compound of any one of embodiments 1 and 2, wherein: Aryl¹ is substituted phenyl; Aryl² is substituted heteroaryl; and X is methylene.

Embodiment 4

The compound of any one of embodiments 1-3, wherein the compound is of the formula:

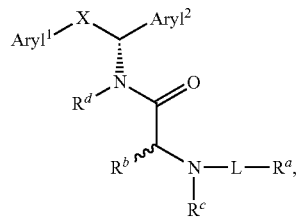

wherein Aryl¹ is para-substituted phenyl; Aryl² is substituted heteroaryl; X is methylene; L is alkylene, alkenylene, or alkynylene, any of which is substituted or unsubstituted, or together with the nitrogen atom to which L is bound forms an amide linkage, a carbamate linkage, a ureido linkage, or a sulfonamide linkage, or a chemical bond; R$^a$ is H, alkyl, alkenyl, alkynyl, aryl, arylalkyl, heterocyclyl, heterocyclylalkyl, heteroaryl, or heteroarylalkyl, any of which is substituted or unsubstituted; R$^b$ is H, alkyl, alkenyl, alkynyl, aryl, arylalkyl, heterocyclyl, heterocyclylalkyl, heteroaryl, or heteroarylalkyl, any of which is substituted or unsubstituted; R$^c$ is H or alkyl which is substituted or unsubstituted; and R$^d$ is H or alkyl which is substituted or unsubstituted.

Embodiment 5

The compound of any one of embodiments 1-4, wherein the compound is of the formula:

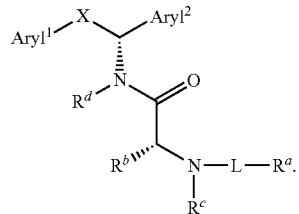

Embodiment 6

The compound of any one of embodiments 1-4, wherein the compound is of the formula:

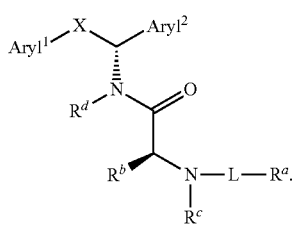

Embodiment 7

The compound of embodiment 4, wherein: Aryl$^1$ is para-substituted phenyl; Aryl$^2$ is a substituted thiazole moiety; X is methylene; L together with the nitrogen atom to which L is bound forms a carbamate linkage; R$^a$ is alkyl, which is substituted or unsubstituted; R$^b$ is arylalkyl, which is substituted or unsubstituted; R$^c$ is H; and R$^d$ is H.

Embodiment 8

The compound of any one of embodiments 1-7, wherein Aryl$^2$ is:

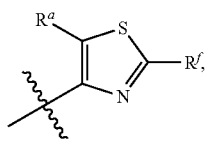

wherein:
R$^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a ureido group, a thioether group, a thioester group, a thioacid group, aryl, arylalkyl, heterocyclyl, heterocyclylalkyl, heteroaryl, or heteroarylalkyl, any of which is substituted or unsubstituted; and R$^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a ureido group, a thioether group, a thioester group, a thioacid group, aryl, arylalkyl, heterocyclyl, heterocyclylalkyl, heteroaryl, or heteroarylalkyl, any of which is substituted or unsubstituted.

Embodiment 9

The compound of embodiment 8, wherein: R$^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and R$^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted.

Embodiment 10

The compound of any one of embodiments 8-9, wherein: R$^e$ is H, OH, F, Cl, Br, I, alkyl, or an alkoxy group, any of which is substituted or unsubstituted; and R$^f$ is alkyl, aryl, heterocyclyl, or heteroaryl, any of which is substituted or unsubstituted.

Embodiment 11

The compound of any one of embodiments 8-10, wherein: Aryl$^1$ is 4-phenylsulfamic acid; R$^a$ is alkyl, which is substituted or unsubstituted; R$^b$ is arylalkyl, which is substituted or unsubstituted; R$^e$ is H; and R$^f$ is heteroaryl.

Embodiment 12

The compound of any one of embodiments 1-5, and 7-11, wherein the compound is:

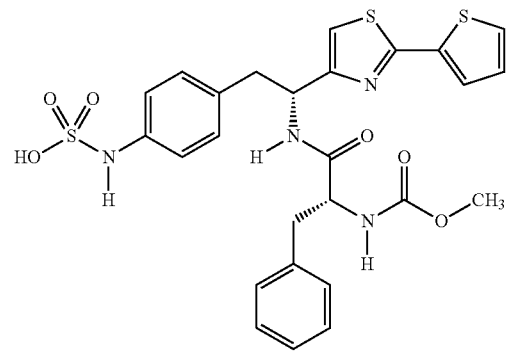

Embodiment 13

The compound of any one of embodiments 1-4, and 6-11, wherein the compound is:

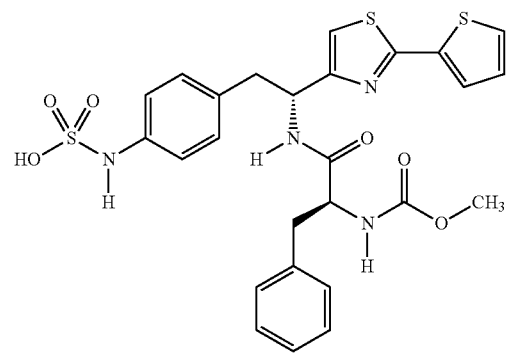

Embodiment 14

A compound of formula:

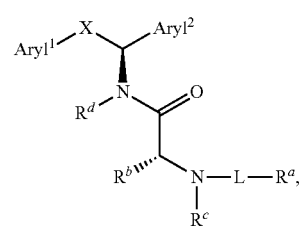

wherein:
Aryl$^1$ is an aryl group which is substituted or unsubstituted;
Aryl$^2$ is an aryl group which is substituted or unsubstituted;

X is alkylene, alkenylene, alkynylene, an ether linkage, an amine linkage, an amide linkage, an ester linkage, a thioether linkage, a carbamate linkage, a carbonate linkage, a ureido linkage, a sulfone linkage, any of which is substituted or unsubstituted, or a chemical bond; L is alkylene, alkenylene, or alkynylene, any of which is substituted or unsubstituted, or together with the nitrogen atom to which L is bound forms an amide linkage, a carbamate linkage, a ureido linkage, or a sulfonamide linkage, or a chemical bond, or together with any of $R^a$, $R^b$, $R^c$, and $R^d$ forms a ring that is substituted or unsubstituted; $R^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, $R^b$, $R^c$, and $R^d$ forms a ring that is substituted or unsubstituted; $R^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, $R^a$, $R^c$, and $R^d$ forms a ring that is substituted or unsubstituted; $R^c$ is H or alkyl which is substituted or unsubstituted, or together with any of L, $R^a$, $R^b$, and $R^d$ forms a ring that is substituted or unsubstituted; $R^d$ is H or alkyl which is substituted or unsubstituted, or together with any of L, $R^a$, $R^b$, and $R^c$ forms a ring that is substituted or unsubstituted; and $R^g$ is H, alkyl, alkenyl, alkynyl, aryl, arylalkyl, heterocyclyl, heterocyclylalkyl, heteroaryl, or heteroarylalkyl, any of which is substituted or unsubstituted, or a pharmaceutically-acceptable salt, tautomer, or zwitterion thereof.

Embodiment 15

The compound of embodiment 14, wherein: $Aryl^1$ is substituted or unsubstituted phenyl; $Aryl^2$ is substituted or unsubstituted heteroaryl; and X is alkylene.

Embodiment 16

The compound of any one of embodiments 14-15, wherein: $Aryl^1$ is substituted phenyl; $Aryl^2$ is substituted heteroaryl; and X is methylene.

Embodiment 17

The compound of any one of embodiments 14-16, wherein: $Aryl^1$ is para-substituted phenyl; $Aryl^2$ is substituted heteroaryl; X is methylene; L is alkylene, alkenylene, or alkynylene, any of which is substituted or unsubstituted, or together with the nitrogen atom to which L is bound forms an amide linkage, a carbamate linkage, a ureido linkage, or a sulfonamide linkage, or a chemical bond; $R^a$ is H, alkyl, alkenyl, alkynyl, aryl, arylalkyl, heterocyclyl, heterocyclylalkyl, heteroaryl, or heteroarylalkyl, any of which is substituted or unsubstituted; $R^b$ is H, alkyl, alkenyl, alkynyl, aryl, arylalkyl, heterocyclyl, heterocyclylalkyl, heteroaryl, or heteroarylalkyl, any of which is substituted or unsubstituted; $R^c$ is H or alkyl which is substituted or unsubstituted; and $R^d$ is H or alkyl which is substituted or unsubstituted.

Embodiment 18

The compound of any one of embodiments 14-17, wherein: $Aryl^1$ is para-substituted phenyl; $Aryl^2$ is a substituted thiazole moiety; X is methylene; L together with the nitrogen atom to which L is bound forms a carbamate linkage; $R^a$ is alkyl, which is substituted or unsubstituted; $R^b$ is arylalkyl, which is substituted or unsubstituted; $R^c$ is H; and $R^d$ is H.

Embodiment 19

The compound of any one of embodiments 14-18, wherein $Aryl^2$ is:

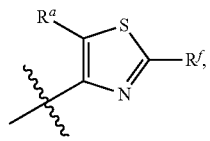

wherein:

$R^e$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a ureido group, a thioether group, a thioester group, a thioacid group, aryl, arylalkyl, heterocyclyl, heterocyclylalkyl, heteroaryl, or heteroarylalkyl, any of which is substituted or unsubstituted; and $R^f$ is H, OH, F, Cl, Br, I, CN, alkyl, alkenyl, alkynyl, an alkoxy group, an ether group, a carboxylic acid group, a carboxaldehyde group, an ester group, an amine group, an amide group, a carbonate group, a carbamate group, a ureido group, a thioether group, a thioester group, a thioacid group, aryl, arylalkyl, heterocyclyl, heterocyclylalkyl, heteroaryl, or heteroarylalkyl, any of which is substituted or unsubstituted.

Embodiment 20

The compound of embodiment 19, wherein: $R^e$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted; and $R^f$ is H, OH, F, Cl, Br, I, alkyl, an alkoxy group, aryl, arylalkyl, heterocyclyl, heterocyclylalkyl, heteroaryl, or heteroarylalkyl, any of which is substituted or unsubstituted.

Embodiment 21

The compound of any one of embodiments 19-20, wherein: $R^e$ is H, OH, F, Cl, Br, I, alkyl, or an alkoxy group, any of which is substituted or unsubstituted; and $R^f$ is alkyl, aryl, heterocyclyl, or heteroaryl, any of which is substituted or unsubstituted.

Embodiment 22

The compound of any one of embodiments 19-21, wherein: $Aryl^1$ is 4-phenylsulfamic acid; $R^a$ is alkyl, which is substituted or unsubstituted; $R^b$ is arylalkyl, which is substituted or unsubstituted; $R^e$ is H; and $R^f$ is heteroaryl.

Embodiment 23

The compound of any one of embodiments 14-21, wherein the compound is:

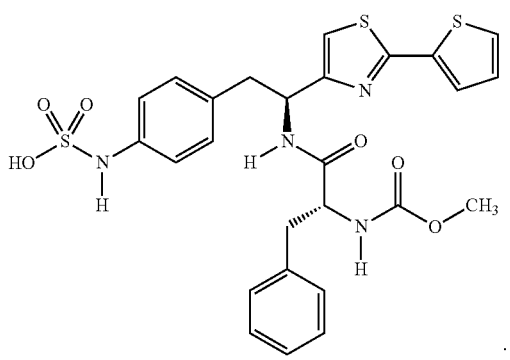 [SMILES: COC(=O)N[C@H](Cc1ccccc1)C(=O)N[C@@H](Cc1ccc(NS(=O)(=O)O)cc1)c1csc(-c2cccs2)n1]

Embodiment 24

A pharmaceutical composition comprising two Tie-2 activators, wherein the two Tie-2 activators are stereoisomers of one another, wherein the pharmaceutical composition is in a unit dosage form.

Embodiment 25

The pharmaceutical composition of embodiment 24, wherein the stereoisomers are enantiomers of one another.

Embodiment 26

The pharmaceutical composition of embodiment 24, wherein the stereoisomers are diastereomers of one another.

Embodiment 27

The pharmaceutical composition of any one of embodiments 24-26, wherein the two Tie-2 activators bind HPTP-beta.

Embodiment 28

The pharmaceutical composition of any one of embodiments 24-27, wherein the two Tie-2 activators inhibit HPTP-beta.

Embodiment 29

The pharmaceutical composition of any one of embodiments 24-28, wherein one of the Tie-2 activators is present in an amount that is no greater than 1% of the amount of the other Tie-2 activator.

Embodiment 30

The pharmaceutical composition of any one of embodiments 24-29, wherein the two Tie-2 activators are small organic molecules.

Embodiment 31

A pharmaceutical composition comprising a Tie-2 activator and a stereoisomer of the Tie-2 activator, wherein the stereoisomer activates Tie-2 with a potency that is from about 0.001% to about 100% the potency of the Tie-2 activator.

Embodiment 32

The pharmaceutical composition of embodiment 31, wherein the stereoisomer of the Tie-2 activator is an enantiomer of the Tie-2 activator.

Embodiment 33

The pharmaceutical composition of embodiment 31, wherein the stereoisomer of the Tie-2 activator is a diastereomer of the Tie-2 activator.

Embodiment 34

The pharmaceutical composition of any one of embodiments 31-33, wherein the stereoisomer activates Tie-2 with a potency that is from about 0.01% to about 10% the potency of the Tie-2 activator.

Embodiment 35

The pharmaceutical composition of any one of embodiments 31-34, wherein the stereoisomer activates Tie-2 with a potency that is from about 0.01% to about 1% the potency of the Tie-2 activator.

Embodiment 36

The pharmaceutical composition of any one of embodiments 31-35, wherein the stereoisomer activates Tie-2 with a potency that is from about 0.01% to about 0.5% the potency of the Tie-2 activator.

Embodiment 37

The pharmaceutical composition of any one of embodiments 31-36, wherein the stereoisomer binds HPTP-beta.

Embodiment 38

The pharmaceutical composition of any one of embodiments 31-37, wherein the stereoisomer inhibits HPTP-beta.

Embodiment 39

The pharmaceutical composition of any one of embodiments 31-38, wherein the stereoisomer is a small organic molecule.

Embodiment 40

A method comprising contacting with a reaction mixture a compound of formula:

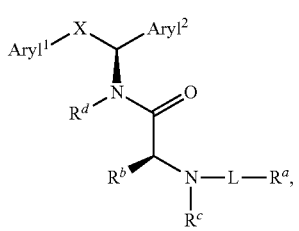

wherein:
Aryl¹ is an aryl group which is substituted or unsubstituted;
Aryl² is an aryl group which is substituted or unsubstituted; X is alkylene, alkenylene, alkynylene, an ether linkage, an amine linkage, an amide linkage, an ester linkage, a thioether linkage, a carbamate linkage, a carbonate linkage, a ureido linkage, a sulfone linkage, any of which is substituted or unsubstituted, or a chemical bond; L is alkylene, alkenylene, or alkynylene, any of which is substituted or unsubstituted, or together with the nitrogen atom to which L is bound forms an amide linkage, a carbamate linkage, a ureido linkage, or a sulfonamide linkage, or a chemical bond, or together with any of $R^a$, $R^b$, $R^c$, and $R^d$ forms a ring that is substituted or unsubstituted; $R^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, $R^b$, $R^c$, and $R^d$ forms a ring that is substituted or unsubstituted; $R^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, $R^a$, $R^c$, and $R^d$ forms a ring that is substituted or unsubstituted; $R^c$ is H or alkyl which is substituted or unsubstituted, or together with any of L, $R^a$, $R^b$, and $R^d$ forms a ring that is substituted or unsubstituted; $R^d$ is H or alkyl which is substituted or unsubstituted, or together with any of L, $R^a$, $R^b$, and $R^c$ forms a ring that is substituted or unsubstituted; and $R^g$ is H, alkyl, alkenyl, alkynyl, aryl, arylalkyl, heterocyclyl, heterocyclylalkyl, heteroaryl, or heteroarylalkyl, any of which is substituted or unsubstituted, or a salt, tautomer, or zwitterion thereof, wherein a stereocenter of the compound or salt thereof inverts, thereby providing a stereoisomer of the compound or a salt, tautomer, or zwitterion of the stereoisomer.

Embodiment 41

The method of embodiment 40, wherein the reaction mixture comprises a base.

Embodiment 42

The method of any one of embodiments 40-41, wherein the compound is:

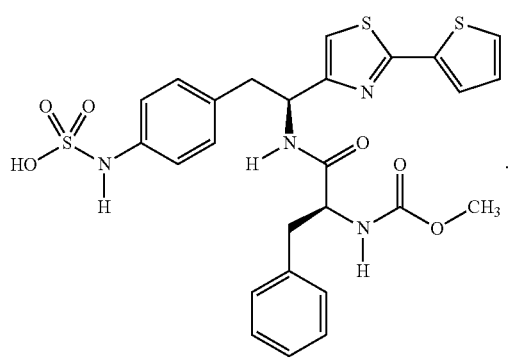 [SMILES: COC(=O)N[C@@H](Cc1ccccc1)C(=O)N[C@@H](Cc1ccc(NS(=O)(=O)O)cc1)c1csc(-c2cccs2)n1]

Embodiment 43

The method of any one of embodiments 40-42, wherein the stereoisomer is:

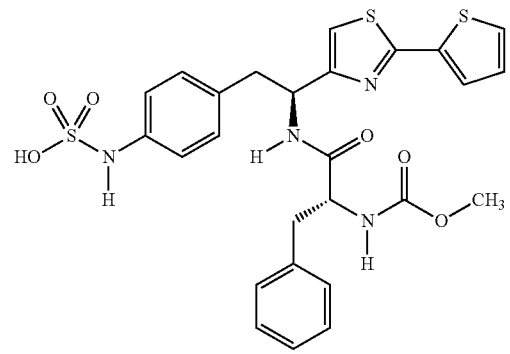

Embodiment 44

A method comprising mixing with a reaction mixture a compound of formula:

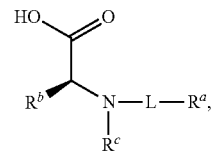

or a salt thereof, and a starting material to provide a product of formula:

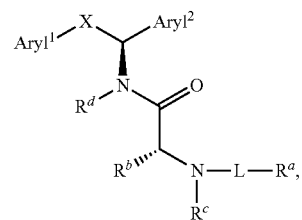

or a salt, tautomer, or zwitterion thereof, wherein: Aryl¹ is an aryl group which is substituted or unsubstituted; Aryl² is an aryl group which is substituted or unsubstituted; X is alkylene, alkenylene, alkynylene, an ether linkage, an amine linkage, an amide linkage, an ester linkage, a thioether linkage, a carbamate linkage, a carbonate linkage, a ureido linkage, a sulfone linkage, any of which is substituted or unsubstituted, or a chemical bond; L is alkylene, alkenylene, or alkynylene, any of which is substituted or unsubstituted, or together with the nitrogen atom to which L is bound forms an amide linkage, a carbamate linkage, a ureido linkage, or a sulfonamide linkage, or a chemical bond, or together with any of $R^a$, $R^b$, $R^c$, and $R^d$ forms a ring that is substituted or unsubstituted; $R^a$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, $R^b$, $R^c$, and $R^d$ forms a ring that is substituted or unsubstituted; $R^b$ is H, alkyl, alkenyl, alkynyl, aryl, arylalkyl, heterocyclyl, heterocyclylalkyl, heteroaryl, or heteroarylalkyl, any of which is substituted or unsubstituted, or together with any of L, $R^a$, $R^c$, and $R^d$ forms a ring that is substituted or unsubstituted; $R^c$ is H or alkyl which is substituted or unsubstituted, or together with any of L, $R^a$, $R^b$, and $R^d$ forms a ring that is substituted or unsubstituted;

$R^d$ is H or alkyl which is substituted or unsubstituted, or together with any of L, $R^a$, $R^b$, and $R^c$ forms a ring that is substituted or unsubstituted; and $R^g$ is H, alkyl, alkenyl, alkynyl, aryl, arylalkyl, heterocyclyl, heterocyclylalkyl, heteroaryl, or heteroarylalkyl, any of which is substituted or unsubstituted.

Embodiment 45

The method of embodiment 44, wherein the compound is:

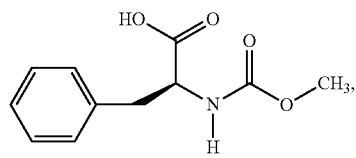 [SMILES: COC(=O)N[C@@H](Cc1ccccc1)C(=O)O]

or a salt thereof.

Embodiment 46

The method of any one of embodiments 44-45, wherein the starting material is:

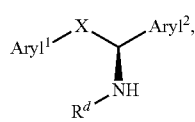

or a salt, tautomer, or zwitterion thereof.

Embodiment 47

The method of any one of embodiments 44-46, wherein the starting material is:

or a salt thereof, wherein Ngroup is a functional group that contains a nitrogen atom.

Embodiment 48

The method of any one of embodiments 44-47, wherein the starting material is:

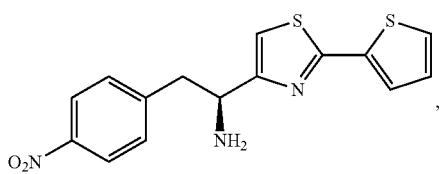 [SMILES: N[C@@H](Cc1ccc([N+](=O)[O-])cc1)c1csc(-c2cccs2)n1]

or a salt thereof.

Embodiment 49

The method of any one of embodiments 44-48, wherein the product is:

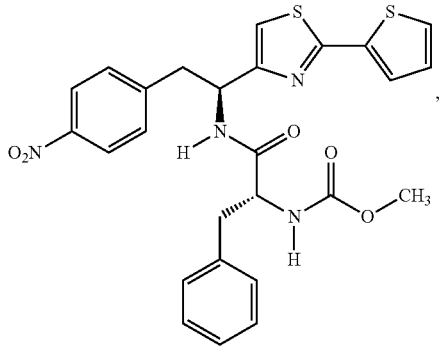 [SMILES: COC(=O)N[C@H](Cc1ccccc1)C(=O)N[C@@H](Cc1ccc([N+](=O)[O-])cc1)c1csc(-c2cccs2)n1]

or a salt thereof.

---

What is claimed is:

1. A compound of formula:

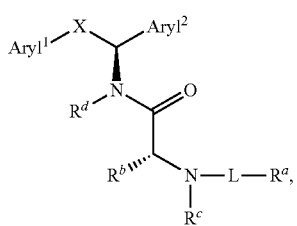

wherein:
Aryl$^1$ is 4-phenylsulfamic acid;
Aryl$^2$ is

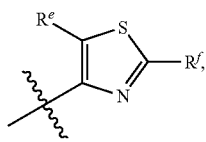

wherein:
R$^e$ is H;
R$^f$ heteroaryl that is substituted or unsubstituted;
X is methylene;
L is alkylene, alkenylene, or alkynylene, any of which is substituted or unsubstituted, or together with the nitrogen atom to which L is bound forms an amide linkage, a carbamate linkage, a ureido linkage, or a sulfonamide linkage, or a chemical bond;
R$^a$ is alkyl, alkenyl, alkynyl, aryl, arylalkyl, heterocyclyl, heterocyclylalkyl, heteroaryl, or heteroarylalkyl, any of which is substituted or unsubstituted, or H;
R$^b$ is alkyl, alkenyl, alkynyl, aryl, arylalkyl, heterocyclyl, heterocyclylalkyl, heteroaryl, or heteroarylalkyl, any of which is substituted or unsubstituted, or H;
R$^c$ is alkyl which is substituted or unsubstituted, or H; and
R$^d$ is alkyl which is substituted or unsubstituted, or H, or a pharmaceutically-acceptable salt, tautomer, or zwitterion thereof.

2. The compound of claim 1, wherein:
L together with the nitrogen atom to which L is bound forms a carbamate linkage;
R$^a$ is alkyl, which is substituted or unsubstituted;
R$^b$ is arylalkyl, which is substituted or unsubstituted;
R$^c$ is H; and
R$^d$ is H.

3. The compound of claim 1, wherein the compound is:

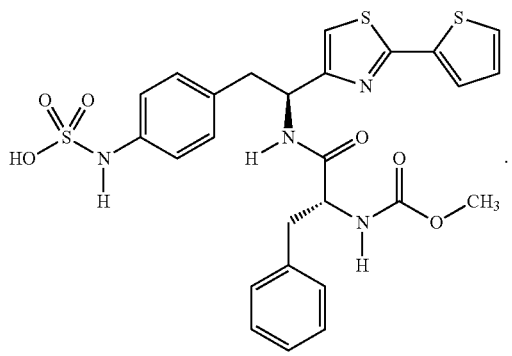 [SMILES: COC(=O)N[C@H](Cc1ccccc1)C(=O)N[C@@H](Cc1ccc(NS(=O)(=O)O)cc1)c1csc(-c2cccs2)n1]

* * * * *